US012735728B2

(12) United States Patent
Evans, IV et al.

(10) Patent No.: US 12,735,728 B2
(45) Date of Patent: Sep. 15, 2026

(54) YEAST STRAIN DEVELOPMENT FOR ETHANOL PRODUCTION

(71) Applicants: AB MAURI, St. Louis, MO (US); VIB VZW, Ghent (BE); KATHOLIEKE UNIVERSITEIT LEUVEN, Leuven (BE)

(72) Inventors: John H. Evans, IV, Denver, CO (US); Aaron J. McKerracher, Belleville, IL (US); Jan Steensels, Lommel (BE); Kevin J. Verstrepen, Leuven (BE)

(73) Assignees: AB MAURI, St. Louis, MO (US); VIB VZW, Ghent (BE); KATHOLIEKE UNIVERSITEIT LEUVEN, Leuven (BE)

( * ) Notice: Subject to any disclaimer, the term of this patent is extended or adjusted under 35 U.S.C. 154(b) by 268 days.

(21) Appl. No.: 18/552,328

(22) PCT Filed: Apr. 4, 2022

(86) PCT No.: PCT/US2022/023343
§ 371 (c)(1),
(2) Date: Sep. 25, 2023

(87) PCT Pub. No.: WO2022/216622
PCT Pub. Date: Oct. 13, 2022

(65) Prior Publication Data

US 2024/0182930 A1 Jun. 6, 2024

Related U.S. Application Data

(60) Provisional application No. 63/170,884, filed on Apr. 5, 2021.

(51) Int. Cl.

| | |
|---|---|
| ***C12P 7/06*** | (2006.01) |
| ***C12N 1/185*** | (2026.01) |
| ***C12P 7/10*** | (2006.01) |
| *C12R 1/865* | (2006.01) |

(52) U.S. Cl.
CPC ................ *C12P 7/10* (2013.01); *C12N 1/185* (2021.05); *C12R 2001/865* (2021.05)

(58) Field of Classification Search
CPC ...... C12P 7/10; C12N 1/185; C12R 2001/865
See application file for complete search history.

(56) References Cited

U.S. PATENT DOCUMENTS

| | | | |
|---|---|---|---|
| 10,036,043 | B2 | 7/2018 | Shihadeh et al. |
| 10,106,823 | B2 | 10/2018 | Bavouzet et al. |
| 10,308,963 | B2 | 6/2019 | Headman et al. |
| 10,364,444 | B2 | 7/2019 | Headman et al. |
| 2007/0014905 | A1 | 1/2007 | Chen et al. |
| 2010/0304490 | A1 | 12/2010 | Ubersax |
| 2010/0311065 | A1 | 12/2010 | Ubersax et al. |
| 2012/0196770 | A1 | 8/2012 | Agresti |
| 2013/0149760 | A1 | 6/2013 | Forrester et al. |
| 2015/0132817 | A1 | 5/2015 | Maekawa et al. |
| 2016/0326484 | A1 | 11/2016 | Jewell et al. |
| 2017/0002383 | A1 | 1/2017 | Kawai Shikishima |
| 2017/0166934 | A1 | 6/2017 | Shihadeh et al. |
| 2018/0312878 | A1 | 11/2018 | Verstrepen et al. |
| 2019/0316111 | A1 | 10/2019 | Thevelein et al. |
| 2019/0338319 | A1 | 11/2019 | Yazdi et al. |

FOREIGN PATENT DOCUMENTS

| | | | |
|---|---|---|---|
| CN | 111205948 | A | 5/2020 |
| EP | 1724336 | B1 | 12/2008 |
| JP | 2008092819 | A | 4/2008 |
| JP | 2011055756 | A | 3/2011 |
| JP | 2013198407 | A | 10/2013 |
| JP | 2014018107 | A | 2/2014 |
| WO | 2006113683 | A2 | 10/2006 |
| WO | 2010141438 | A1 | 6/2010 |
| WO | 2011010923 | A1 | 1/2011 |
| WO | 2012103516 | A1 | 8/2012 |
| WO | 2012158466 | A1 | 11/2012 |
| WO | 2015099727 | A1 | 7/2015 |
| WO | 2017037241 | A1 | 3/2017 |
| WO | 2018115251 | A1 | 6/2018 |
| WO | 2019161227 | A1 | 8/2019 |
| WO | 2022216622 | A1 | 10/2022 |
| WO | 2024097243 | A1 | 5/2024 |

OTHER PUBLICATIONS

International Search Report and Written Opinion for Application No. PCT/US2024/036792 dated Dec. 10, 2024 (13 pages).

International Search Report and Written Opinion for Application No. PCT/US2025/020048 dated May 2, 2025 (11 pages).

European Patent Office. Extended European Search Report for Application No. 22785241.5, dated Mar. 27, 2025 (12 pages).

Favaro, L. et al. "Exploring industrial and natural *Saccharomyces cerevisiae* strains for the bio-based economy from biomass: the case of bioethanol." Critical reviews in biotechnology 39.6 (2019): 800-816.

Vautard, G. et al. "The glucose repressor CRE1 from Sclerotinia sclerotiorum is functionally related to CREA from Aspergillus nidulans but not to the Mig proteins from *Saccharomyces cerevisiae*." FEBS letters 453.1-2 (1999): 54-58.

Becker, D. M., et al. "Introduction of DNA into yeast cells." Current protocols in molecular biology 27.1 (1994): 13-7.1-13.7.10.

(Continued)

*Primary Examiner* — Maryam Monshipouri
(74) *Attorney, Agent, or Firm* — Michael Best & Friedrich LLP

(57) ABSTRACT

Disclosed herein are yeast strains and derivatives thereof, as well as compositions comprising the yeast strains for use in ethanol manufacture. The disclosure also relates to processes for producing ethanol from biomass using the yeast strains and compositions. In particular, the yeast strains produce lower glycerol and higher ethanol, and have a higher temperature tolerance and higher fermentation rate than strains and products currently used in ethanol production processes.

17 Claims, 10 Drawing Sheets

(56) References Cited

OTHER PUBLICATIONS

Huxley, C. et al. "Rapid assessment of S. cerevisiae mating type by PCR." Trends in genetics: TIG 6.8 (1990): 236.
International Preliminary Report on Patentability for Application No. PCT/US2022/023343 dated Oct. 10, 2023 (7 pages).
International Search Report and Written Opinion for Application No. PCT/US2022/023343 dated Aug. 19, 2022 (21 pages).
International Search Report and Written Opinion for Application No. PCT/US2023/036514 dated Feb. 13, 2024 (15 pages).
Olbrich, H. (2006). The molasses. Biotechnologie-Kempe GmbH, 128.
Thomas, K. C., et al. "Effect of lactobacilli on yeast growth, viability and batch and semi-continuous alcoholic fermentation of corn mash." Journal of Applied Microbiology 90.5 (2001): 819-828.
Yang, Z. et al. "Genome editing systems across yeast species." Current opinion in biotechnology 66 (2020): 255-266.
Examination Report No. 1 issued by the Australian Government for Application No. 2022254037 dated Oct. 17, 2025 (3 pages).
Yamasaki, R., et al. "Development of sake yeast haploid set with diverse brewing properties using sake yeast strain Hiroshima No. 6 exhibiting sexual reproduction." Journal of bioscience and bioengineering 129.6 (2020): 706-714.
Japanese Patent Office. Notice of Reasons for Refusal for Application No. 2023-561734, dated Apr. 2, 2026, 14 pages with translation.

Parentals
First yeast strain
Second yeast strain
sporulation
spores
Screening
Derivatives
Screening
Derivative with defining characteristics Parentals
First yeast strain
Second yeast strain
Third yeast strain
sporulation
spores
Derivatives
Derivative with defining characteristics

YEAST STRAIN DEVELOPMENT FOR ETHANOL PRODUCTION

CROSS REFERENCE TO RELATED APPLICATIONS

This patent application claims priority to U.S. Provisional Application No. 63/170,884, filed Apr. 5, 2021, the contents of which are incorporated herein by reference in its entirety.

FIELD

This disclosure relates to yeast strains and derivatives thereof, as well as compositions comprising the yeast strains for use in ethanol manufacture. The disclosure also relates to processes for producing ethanol from biomass using the yeast strains and compositions. In particular, the yeast strains produce lower glycerol and higher ethanol, and have higher temperature and organic acid tolerances and higher fermentation rate than strains and products currently used in ethanol production processes.

INTRODUCTION

Ethanol can be produced from biological organisms using different biochemical pathways inherent to the organism. Ethanol produced from biological organisms is termed bio-ethanol and is thereby distinguished from ethanol produced by purely chemical methods. Bioethanol is manufactured commercially and can be used as a liquid fuel in internal combustion engines (fuel ethanol), as an ingredient in industrial products (industrial ethanol), or as a component in alcoholic beverages (potable ethanol).

Biological organisms such as yeasts produce bioethanol. Selected yeasts are advantageous for ethanol production so that the production processes and profitability can be optimized. Yeast which are used for commercial production of ethanol require several characteristics including adequate ethanol metabolic yield, adequate ethanol tolerance, acceptable by-product yield, adequate fermentation kinetics, and some degree of thermotolerance during fermentation. Yeast of the genus *Saccharomyces* exhibit many of these characteristics required for commercial production of ethanol. Commercial yeast products that comprise *Saccharomyces* include: Ethanol Red® (Fermentis®), Thermosacc® (Lallemand®), Angel Super Alcohol® (Angel®) and Fali (AB Mauri®). Although commercial yeast strains and products have advantageous characteristics for production of ethanol, there is an increasing need for improvements in the efficiency of ethanol production to reduce cost of manufacture.

Therefore, there is a need for new and improved strains of *Saccharomyces* from which to produce new and improved yeast products. The improved yeast strains and products need to be capable of improving the efficiency of commercial ethanol production by providing a higher conversion of sugar to ethanol, higher temperature tolerance, higher tolerance to fermentation inhibitors, and more rapid fermentation kinetics than yeast strains and products currently in commercial use.

SUMMARY

In an aspect, the disclosure relates to a *Saccharomyces* yeast strain selected from: (a) *Saccharomyces* strain Y1912, a representative sample of the strain having been deposited under NRRL Patent Deposit Designation No. Y-68003; (b) *Saccharomyces* strain Y1913, a representative sample of the strain having been deposited under NRRL Patent Deposit Designation No. Y-68004; (c) *Saccharomyces* strain Y1914, a representative sample of the strain having been deposited under NRRL Patent Deposit Designation No. Y-68005; (d) *Saccharomyces* strain Y1919, a representative sample of the strain having been deposited under NRRL Patent Deposit Designation No. Y-68006; (e) *Saccharomyces* strain Y1923, a representative sample of the strain having been deposited under NRRL Patent Deposit Designation No. Y-68007; (f) *Saccharomyces* strain Y1927, a representative sample of the strain having been deposited under NRRL Patent Deposit Designation No. Y-68008; and, (g) *Saccharomyces* strain Y1929, a representative sample of the strain having been deposited under NRRL Patent Deposit Designation No. Y-68009.

In a further aspect, the disclosure relates to a derivative of a *Saccharomyces* yeast strain selected from: (a) *Saccharomyces* strain Y1912, a representative sample of the strain having been deposited under NRRL Patent Deposit Designation No. Y-68003; (b) *Saccharomyces* strain Y1913, a representative sample of the strain having been deposited under NRRL Patent Deposit Designation No. Y-68004; (c) *Saccharomyces* strain Y1914, a representative sample of the strain having been deposited under NRRL Patent Deposit Designation No. Y-68005; (d) *Saccharomyces* strain Y1919, a representative sample of the strain having been deposited under NRRL Patent Deposit Designation No. Y-68006; (e) *Saccharomyces* strain Y1923, a representative sample of the strain having been deposited under NRRL Patent Deposit Designation No. Y-68007; (f) *Saccharomyces* strain Y1927, a representative sample of the strain having been deposited under NRRL Patent Deposit Designation No. Y-68008; and, (g) *Saccharomyces* strain Y1929, a representative sample of the strain having been deposited under NRRL Patent Deposit Designation No. Y-68009. In one embodiment, the yeast strain or the derivative comprise one or more defining characteristics selected from: (a) a higher ethanol yield than *Saccharomyces* strain Y1609 under same fermentation conditions; (b) an increased temperature tolerance compared to *Saccharomyces* strain Y1609 at a temperature from 32° C. to 36° C.; (c) a lower glycerol yield than *Saccharomyces* strain Y1609 under same fermentation conditions; (d) an increased organic acid tolerance compared to *Saccharomyces* strain Y1609 at a pH from about 4.0 to about 5.2 in the presence of organic acids; and (e) an increased fermentation rate compared to *Saccharomyces* strain Y1609 under the same fermentation conditions. In another embodiment, the yeast strain or the derivative produces at least about 0.5% more ethanol after 50 hours of fermentation relative to *Saccharomyces cerevisiae* strain Y1609. In another embodiment, the yeast strain or the derivative produces at least about 2% less glycerol after 50 hours of fermentation relative to *Saccharomyces cerevisiae* strain Y1609. In another embodiment, the yeast strain or the derivative has a fermentation rate that is at least about 2% higher than *Saccharomyces cerevisiae* strain Y1609 after 24 hours of fermentation. In another embodiment, the temperature is 32° C. In another embodiment, the yeast strain or the derivative produces at least about 5% more ethanol after 50 hours of fermentation relative to *Saccharomyces cerevisiae* strain Y1609. In another embodiment, the yeast strain or the derivative produces at least about 3% less glycerol after 50 hours of fermentation relative to *Saccharomyces cerevisiae* strain Y1609. In another embodiment, the yeast strain or the derivative has a fermentation rate that is at least about 10% higher than *Saccharomyces cerevisiae* strain Y1609 after 24 hours of fermentation. In another embodiment, the temperature is 36° C. In another embodiment, the organic acids comprise lactic acid, acetic acid, succinic acid, citric acid, malic acid, fumaric acid, or a combination thereof.

Another aspect of the disclosure provides a method of producing the derivative of a *Saccharomyces* yeast strain as described herein comprising: (a) providing: (i) a first yeast strain, wherein the first yeast strain is selected from *Saccharomyces strains* Y1912, Y1913, Y1914, Y1919, Y1923, Y1927, Y1929, and derivatives thereof; and (ii) a second yeast strain, wherein the second yeast strain is in the *Saccharomyces* sensu stricto clade; (b) inducing sporulation of the first yeast strain and the second yeast strain; (c) screening and selecting spores from the first yeast strain and spores from the second yeast strain; (d) hybridizing the selected spores of the first yeast strain with the selected spores of the second yeast strain; and (e) screening or selecting for a derivative strain. In one embodiment, step (c) comprises screening or selecting spores which exhibit one or more defining characteristics of *Saccharomyces* strains Y1912, Y1913, Y1914, Y1919, Y1923, Y1927, Y1929, or a derivative thereof. In another embodiment, step (e) comprises screening or selecting a hybrid which exhibits one or more defining characteristics of *Saccharomyces* strains Y1912, Y1913, Y1914, Y1919, Y1923, Y1927, Y1929, or a derivative thereof.

Another aspect of the disclosure provides a method of producing the derivative of a *Saccharomyces* yeast strain as described herein comprising: (a) providing: (i) a first yeast strain, wherein the first yeast strain is selected from *Saccharomyces* strains Y1912, Y1913, Y1914, Y1919, Y1923, Y1927, Y1929, and derivatives thereof; and (ii) one or more additional yeast strains that are in the *Saccharomyces* sensu stricto clade; (b) inducing sporulation of the first yeast strain and the one or more additional yeast strains to produce spores; (c) mixing all of the spores of step (b) to allow for hybridization of the spores; and (d) screening or selecting for a derivative strain. In one embodiment, step (d) comprises screening or selecting a hybrid which exhibits one or more defining characteristics of *Saccharomyces* strains Y1912, Y1913, Y1914, Y1919, Y1923, Y1927, or Y1929.

Another aspect of the disclosure provides a mutant yeast of a yeast strain as described herein or a derivative as described herein.

Another aspect of the disclosure provides a method of producing the mutant yeast as described herein, wherein the mutant yeast is mutated by contacting the yeast strain with a mutagen. In one embodiment, the mutagen is ethyl methanesulfonate (EMS), ultraviolet light (UV), X-rays, methylmethane sulphonate (MMS), nitrous acid, nitrosoguanidine (NNG), acridine mustard, 2-methoxy-6-chloro-9[3-(ethyl-2-chloroethyl)aminopropylamino]acridine•2 (ICR-170), or nitrogen mustard.

Another aspect of the disclosure provides a method of producing the mutant yeast as described herein, wherein the mutant yeast is mutated by contacting the derivative with a mutagen. In one embodiment, the mutagen is ethyl methanesulfonate (EMS), ultraviolet light (UV), X-rays, methylmethane sulphonate (MMS), nitrous acid, nitrosoguanidine (NNG), acridine mustard, 2-methoxy-6-chloro-9[3-(ethyl-2-chloroethyl)aminopropylamino]acridine•2 (ICR-170), or nitrogen mustard.

Another aspect of the disclosure provides an evolved yeast of a yeast strain as described herein or a derivative as described herein.

Another aspect of the disclosure provides a method of producing the evolved yeast as described herein, wherein evolution is induced by applying selection pressure to the yeast strain.

Another aspect of the disclosure provides a method of producing the evolved yeast as described herein, wherein evolution is induced by applying selection pressure to the derivative.

Another aspect of the disclosure provides a genetically modified yeast of a yeast strain as described herein or a derivative as described herein. In one embodiment, a nucleic acid sequence of the genetically modified yeast is changed using gene editing.

Another aspect of the disclosure provides a recombinant yeast of a yeast strain as described herein or a derivative as described herein. In one embodiment, the recombinant yeast comprises a modification to suppress expression of a gene, enhance expression of a gene, introduce a gene, or delete a gene.

Another aspect of the disclosure provides a process for producing ethanol from a substrate by contacting the substrate with a fermenting organism, wherein the fermenting organism is selected from: (a) *Saccharomyces* strain Y1912, a representative sample of the strain having been deposited under NRRL Patent Deposit Designation No. Y-68003, or a derivative thereof; (b) *Saccharomyces* strain Y1913, a representative sample of the strain having been deposited under NRRL Patent Deposit Designation No. Y-68004, or a derivative thereof; (c) *Saccharomyces* strain Y1914, a representative sample of the strain having been deposited under NRRL Patent Deposit Designation No. Y-68005, or a derivative thereof; (d) *Saccharomyces* strain Y1919, a representative sample of the strain having been deposited under NRRL Patent Deposit Designation No. Y-68006, or a derivative thereof; (e) *Saccharomyces* strain Y1923, a representative sample of the strain having been deposited under NRRL Patent Deposit Designation No. Y-68007, or a derivative thereof; (f) *Saccharomyces* strain Y1927, a representative sample of the strain having been deposited under NRRL Patent Deposit Designation No. Y-68008, or a derivative thereof; and, (g) *Saccharomyces* strain Y1929, a representative sample of the strain having been deposited under NRRL Patent Deposit Designation No. Y-68009, or a derivative thereof. In one embodiment, the substrate comprises or originates from sugar cane, sugar beet, sweet sorghum, agave, corn, wheat, rice, barley, rye, sorghum, triticale, potato, sweet potato, cassava, or a combination thereof. In another embodiment, the yeast strain comprises one or more defining characteristics selected from: (a) a higher ethanol yield than *Saccharomyces* strain Y1609 under same fermentation conditions; (b) an increased temperature tolerance compared to *Saccharomyces* strain Y1609 at a temperature from 32° C. to 36° C.; (c) a lower glycerol yield than *Saccharomyces* strain Y1609 under same fermentation conditions; (d) an increased organic acid tolerance compared to *Saccharomyces* strain Y1609 at a pH from about 4.0 to about 5.2 in the presence of organic acids; and (e) an increased fermentation rate compared to *Saccharomyces* strain Y1609 under the same fermentation conditions. In another embodiment, the ethanol is used for fuel ethanol, industrial ethanol, potable ethanol, or a combination thereof. In another embodiment, the ethanol is produced using a starch. In another embodiment, simultaneous saccharification and fermentation (SSF) or continuous fermentation is used to produce the ethanol. In another embodiment, the ethanol is produced using a sugar. In another embodiment, batch fermentation or continuous fermentation is used to produce the ethanol. In another embodiment, the ethanol is produced using a lignocellulosic sugar. In another embodiment, simultaneous saccharification and fermentation (SSF) or Separate Hydrolysis and Fermentation (SHF) is used to produce the ethanol.

Another aspect of the disclosure provides a composition comprising the yeast strain as described herein or the derivative as described herein and one or more components selected from surfactants, emulsifiers, gums, swelling agents, protectants, and antioxidants. In one embodiment, the composition comprises one or more defining characteristics selected from: (a) a higher ethanol yield than Fali under same fermentation conditions; (b) an increased temperature tolerance compared to Fali at a temperature from 32° C. to 36° C.; (c) a lower glycerol yield than Fali under same fermentation conditions; (d) an increased organic acid tolerance compared to Fali at a pH from about 4.0 to about 5.2 in the presence of organic acids; and (e) an increased fermentation rate compared to Fali under the same fermentation conditions.

Another aspect of the disclosure provides a process for producing ethanol from a biomass by contacting the biomass with the composition as described herein. In one embodiment, the ethanol is used for fuel ethanol, industrial ethanol, potable ethanol, or a combination thereof. In another embodiment, the ethanol is produced using a starch. In another embodiment, simultaneous saccharification and fermentation (SSF) or continuous fermentation is used to produce the ethanol. In another embodiment, the ethanol is produced using a sugar. In another embodiment, batch fermentation or continuous fermentation is used to produce the ethanol. In another embodiment, the ethanol is produced using a lignocellulosic sugar. In another embodiment, simultaneous saccharification and fermentation (SSF) or Separate Hydrolysis and Fermentation (SHF) is used to produce the ethanol.

Another aspect of the present disclosure provides a method of producing a fermentation product from a substrate by contacting the substrate with a fermenting organism, wherein the fermenting organism is selected from: (a) *Saccharomyces* strain Y1912, a representative sample of the strain having been deposited under NRRL Patent Deposit Designation No. Y-68003, or a derivative thereof; (b) *Saccharomyces* strain Y1913, a representative sample of the strain having been deposited under NRRL Patent Deposit Designation No. Y-68004, or a derivative thereof; (c) *Saccharomyces* strain Y1914, a representative sample of the strain having been deposited under NRRL Patent Deposit Designation No. Y-68005, or a derivative thereof; (d) *Saccharomyces* strain Y1919, a representative sample of the strain having been deposited under NRRL Patent Deposit Designation No. Y-68006, or a derivative thereof; (e) *Saccharomyces* strain Y1923, a representative sample of the strain having been deposited under NRRL Patent Deposit Designation No. Y-68007, or a derivative thereof; (f) *Saccharomyces* strain Y1927, a representative sample of the strain having been deposited under NRRL Patent Deposit Designation No. Y-68008, or a derivative thereof; and, (g) *Saccharomyces* strain Y1929, a representative sample of the strain having been deposited under NRRL Patent Deposit Designation No. Y-68009, or a derivative thereof. In one embodiment, the substrate comprises or originates from sugar cane, sugar beet, sweet sorghum, agave, corn, wheat, rice, barley, rye, sorghum, triticale, potato, sweet potato, cassava, or a combination thereof. In another embodiment, the fermentation product is ethanol. In another embodiment, the ethanol is used for fuel ethanol, industrial ethanol, potable ethanol, or a combination thereof. In another embodiment, batch fermentation, continuous fermentation, simultaneous saccharification and fermentation (SSF), or Separate Hydrolysis and Fermentation (SHF) is used to produce the fermentation product.

The disclosure provides for other aspects and embodiments that will be apparent in light of the following detailed description and accompanying figures.

BRIEF DESCRIPTION OF THE DRAWINGS

FIG. 1 shows processes for making new yeast strains.

DETAILED DESCRIPTION

Figures 1A, 1B:
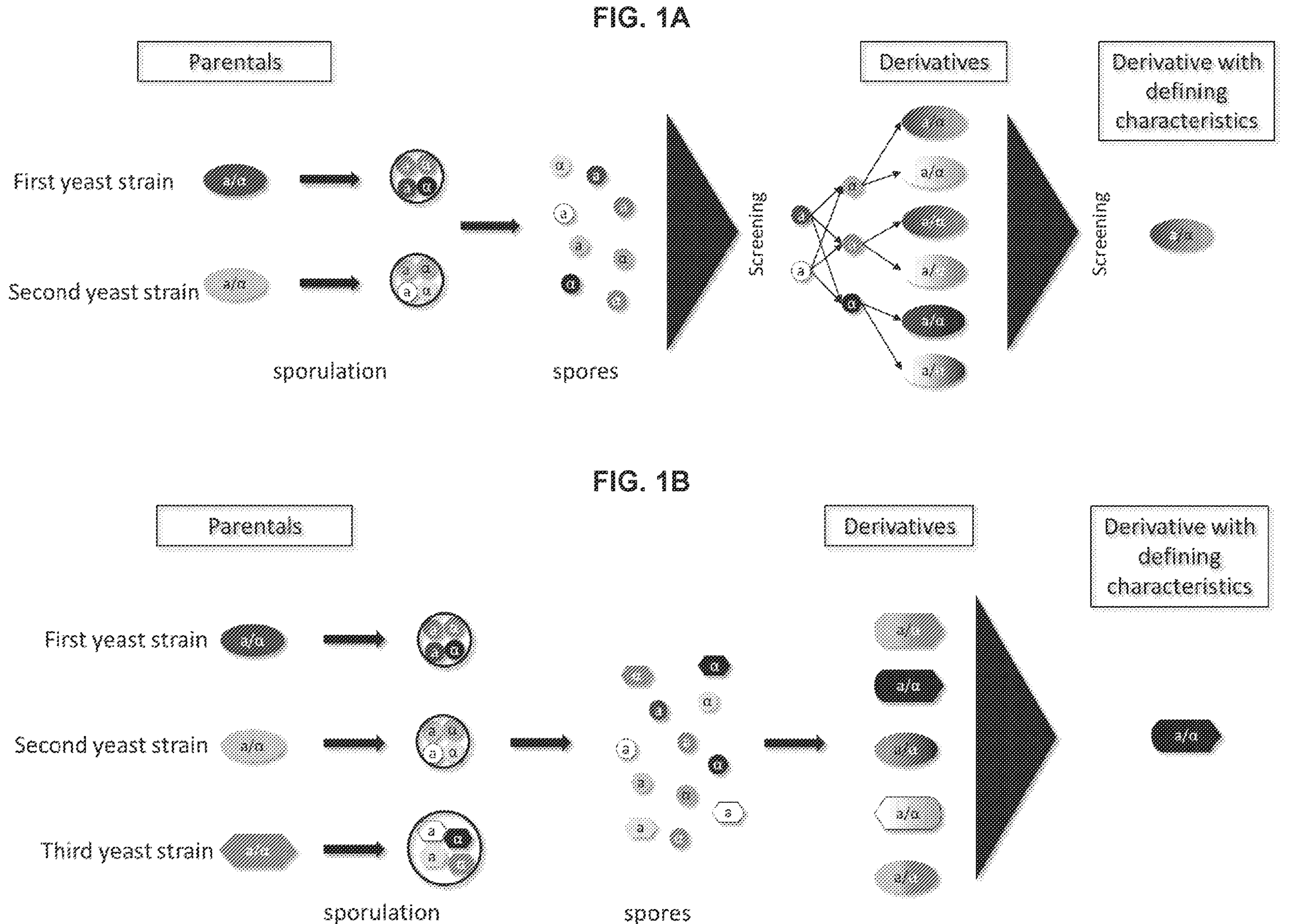
FIG. 1A shows directed mating.
FIG. 1B shows mass mating.

Described herein are fermenting organisms that comprise defining characteristics that include a higher ethanol yield, lower glycerol yield, higher temperature and inhibitor tolerance, and higher fermentation rate relative to current industry standard yeasts used in yeast products such as Fali, under the same fermentation conditions. Also described herein are *Saccharomyces* yeast strains that have improved properties compared to the yeast strain used in Fali. The present disclosure relates to processes for manufacturing yeast products from yeast strains. The present disclosure also relates to improved processes of producing ethanol from different fermentable biomass materials using the fermenting organisms described herein.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents, and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9; for the range 6.0-7.0, the number 6.0, 6.1, 6.2, 6.3, 6.4, 6.5, 6.6, 6.7, 6.8, 6.9, and 7.0 are explicitly contemplated; and for the range from 1 to 5, the numbers 2, 3, and 4 are contemplated in addition to 1 and 5.

The term "about" or "approximately" as used herein as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, preferably within 5-fold, and more preferably within 2-fold, of a value.

As used herein the term "biomass" refers to any organic matter of plant origin that can become a carbohydrate source after conversion. Preferably, the biomass may be derived from agricultural or food-processing products and/or coproducts. In particular, the biomass may be rich in sucrose or in starch, and is chosen from, or is derived from, for example, sorghum, sugar cane, sugar beet, sweet sorghum, agave, corn, wheat, rice, barley, rye, sorghum, triticale, potato, sweet potato, cassava, or a mixture thereof.

As used herein, "combining of DNA" between yeast strains refers to combining of all or a part of the genome of the yeast strains. Combining of DNA between yeast strains may be by any method suitable for combining DNA of at least two yeast cells, and may include, for example, mating methods which comprise sporulation of the yeast strains to produce haploid cells and subsequent hybridizing or mating of compatible haploid cells; cytoduction; or cell fusion such as protoplast fusion.

As used herein, a "derivative" is a yeast strain derived from a yeast strain disclosed herein (e.g., *Saccharomyces* or in the *Saccharomyces* sensu stricto clade), including through hybridization, mutagenesis, recombinant DNA technology, mating, cell fusion, or cytoduction between yeast strains. The derivative strain may be a direct progeny (i.e., the product of a mating between a strain of the invention and another strain or itself).

As used herein, "ethanol yield from glucose" is the yield of ethanol that would be achieved from glucose. In one embodiment, the ethanol yield from glucose is represented by the statement: one molecule of glucose yields two molecules of ethanol and two molecules of carbon dioxide. In another embodiment, the ethanol yield from glucose is represented by the chemical formula: $C_6H_{12}O_6 \rightarrow 2C_2H_5OH+2CO_2$, where $C_6H_{12}O_6$ is the chemical formula for glucose, $C_2H_5OH$ is the chemical formula for ethanol, and $CO_2$ is the chemical formula for carbon dioxide. In another embodiment, the ethanol yield from glucose is represented on a mass basis, where 1.0 gram glucose yields 0.511 gram ethanol and 0.489 gram carbon dioxide. The highest ethanol yield from glucose is two molecules of ethanol from one molecule of glucose. The highest ethanol yield on a mass basis is 0.511 gram ethanol from one gram glucose.

The term "the control" is used interchangeably with "Y1609" when discussing yeast strains and "Fali" when discussing yeast products. Strain Y1609 is used to manufacture the yeast product Fali. Fali can be manufactured as an active dried yeast product, as a crumble yeast product, and as a liquid yeast product for use in fermentation of substrates to fuel ethanol, industrial ethanol and to potable ethanol. Fali is particularly well-suited for use in fermentation of sucrose, glucose, and fructose liberated from biomass containing those sugars and in fermentation of sugar liberated from starch-containing biomass following liberation of sugars by the action of enzymatic or chemical processes. Fali can be used in batch fermentation, continuous fermentation, and simultaneous saccharification fermentations (SSF) of starch substrates. It has a high tolerance to liberated glucose, a high cell count (>$20\times10^9$ cells/g), a moderate ethanol and temperature tolerance, and moderate organic acid tolerance. It rehydrates well in direct pitch applications and can be used in conjunction with glucoamylase and alpha amylase enzyme systems. Fali has an optimal performance within a pH range of 4.0 to 5.0 but can ferment well in a pH range of 3.5 to 6.0. Optimal fermentation temperature of Fali is dependent on stresses present (e.g., organic acid, ethanol, and pH) but generally ferments well in a temperature range of about 32° C. Fali is commercially available from AB Mauri®.

The term "fermentation medium" refers to the environment in which fermentation, using a fermenting organism, is carried out and which includes the fermentable substrate, that is, a carbohydrate source (e.g., glucose) that can be metabolized by the fermenting organism into a desired fermentation product, such as ethanol. The fermentation medium may comprise fermentation nutrients for the fermenting organism. Fermentation nutrients are widely used in the art of fermentation and include nitrogen sources, such as ammonia urea, vitamins, minerals, or combinations thereof. "Feed" is a fermentation medium, however, the feed may have a different composition than the fermentation medium.

"High-yield ethanol production," as used herein, means an ethanol production by fermentation wherein the ethanol yield is near the ethanol yield from glucose. High-yield ethanol production requires limited byproducts, such as glycerol, and yeast growth during fermentation.

The terms "improved," "increased," "enhanced," or "greater" as used herein refer to the heightening or bettering of a particular characteristic or trait as compared to other similar organisms, a control, or a wild-type organism. Typically, this is a fermentation-related advantageous trait.

The term "inoculum" is intended to mean an amount of the microorganism that is added to the main fermenter in order to start the fermentation process. In case of a fermentation process using seed fermenter the inoculum is typically an amount of the preculture corresponding to 5 to 20% of the volume of the main fermenter.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in yeast; multiple copies of a gene encoding the substance; and use of a stronger promoter than the promoter naturally associated with the gene encoding the substance). An isolated substance may be present in a fermentation broth sample; for example, a yeast may be genetically modified to express a particular polypeptide. The fermentation broth from that yeast will comprise the isolated polypeptide.

The term "low pH" as used herein refers to a pH from about 2.5 to about 4.5. A low pH is preferably less than about 4.5. The term "normal pH" as used herein refers to a pH from about 4.0 to about 6.0. A normal pH is preferably about 5.0.

The term "main fermenter" as used herein is used for the final fermenter used in a fermentation process for producing a fermentation product, wherein the intended fermentation product is produced.

The terms "parental" or "parent" strain refers to a yeast strain from which a derivative strain is derived. In some embodiments, a derivative may also be a parent.

The term "preculture" is understood as a liquid actively growing culture of the microorganism (i.e. yeast) used for inoculating the main fermenter. Actively growing is intended to mean that the culture is in a stage where the microorganism is increasing the number of cells. The preculture is in general used as inoculation material in order to avoid or reduce the lag phase in the main fermenter. In fermentation to manufacture ethanol, cells in a pre-fermenter are typically conditioned. The idea is not to produce yeast biomass, as the carbon in the biomass reduces the carbon going to ethanol. There is fermentative growth, but it is not desirable to promote aerobic growth (e.g., using a seed fermenter). Alternatively, yeast may be added directly to the main fermenter by "direct pitch."

As used herein, the terms "properties" and "defining characteristics" of the *Saccharomyces cerevisiae* strains as detailed herein include at least increased ethanol yield compared to the control (i.e. Fali or Y1609) under the same process conditions. Other "properties" and "defining characteristics" include, inter alia, increased temperature tolerance, increased fermentation rate, increased organic acid tolerance, increased ethanol production, and decreased glycerol production. A fermenting organism described herein, for example, used in a process described herein may have one or more the above mentioned "properties" and "defining characteristics."

The term "pre-fermenter" is intended to mean a fermenter wherein the preculture is formed by fermenting the microorganism until the yeast are activated and conditioned for inoculation into the main fermenter. When a pre-fermenter is not used, "direct pitch" is used.

As used herein, a "substrate" is a molecule that can be directly or indirectly metabolized to ethanol by fermentation by *Saccharomyces* or any of the yeast or yeast products described herein.

The term "wild-type" as used herein refers to the typical form of an organism or its genetic material, as it normally occurs, as distinguished from a selected organism.

The term "yeast product" and "composition" are used interchangeably herein and as used herein refers to a composition that includes, among other things, dry yeast, starches and emulsifiers. A yeast product may also be a liquid composition that includes, among other things, cream yeast, glycerol, and xanthan gum.

Unless otherwise defined herein, scientific and technical terms used in connection with the present disclosure shall have the meanings that are commonly understood by those of ordinary skill in the art. For example, any nomenclatures used in connection with, and techniques of, cell biology, molecular biology, microbiology, genetics, and protein and nucleic acid chemistry described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. YEAST STRAINS AND YEAST STRAIN DERIVATIVES

Yeast strains and yeast strain derivatives, as used herein, can be any yeast useful for ethanol production, including, but not limited to, *Saccharomyces, ZygoSaccharomyces, Brettanomyces*, and *Kluyveromyces*. Preferably, the yeast may be a *Saccharomyces* sp., even more preferably it may be a *Saccharomyces cerevisiae.*

In addition, the *Saccharomyces* yeast strains and the derivatives thereof described herein can be readily distinguished from: (a) naturally occurring strains of *Saccharomyces*; (b) contaminating strains of *Saccharomyces*; and (c) other strains used in the ethanol industry that do not have the ethanol producing capabilities and defining characteristics of the strains described herein.

In some embodiments, the yeast strains and the derivatives thereof as described herein have a statistically significantly higher ethanol yield than typical yeast strains used for fermentation (e.g., *Saccharomyces* strain Y1609). In some embodiments, the yeast strains and the derivatives thereof as described herein have a statistically significantly higher ethanol yield than typical yeast strains used for fermentation (e.g., *Saccharomyces* strain Y1609) at a temperature from 20° C. to 40° C., preferably from 32° C. to 36° C. In a particular embodiment, the yeast strains and the derivatives thereof as described herein have a statistically significantly higher ethanol yield than typical yeast strains used for fermentation (e.g., *Saccharomyces* strain Y1609) at a temperature of 32° C. In another particular embodiment, the yeast strains and the derivatives thereof as described herein have a statistically significantly higher ethanol yield than typical yeast strains used for fermentation (e.g., *Saccharomyces* strain Y1609) at a temperature of 36° C. The inventors have surprisingly found that the yeast strains described herein result in a statistically significantly higher ethanol yield compared to Y1609 under the same fermentation conditions. The inventors have also surprisingly found that the derivatives described herein generally result in a statistically significantly higher ethanol yield compared to Y1609 under the same conditions (e.g., Y1919 in FIGS. 2-5).

In some embodiments, the yeast strains and the derivatives thereof as described herein produce at least about 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast strains used for fermentation (e.g., *Saccharomyces* strain Y1609). In some embodiments, the yeast strains and the derivatives thereof as described herein produce at most about 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast strains used for fermentation (e.g., *Saccharomyces* strain Y1609). In some embodiments, the yeast strains and the derivatives thereof as described herein produce about 0.1%-21% (i.e. from about 0.1% to about 21%), 0.2%-21%, 0.3%-21%, 0.4%-21%, 0.5%-21%, 0.6%-21%, 0.7%-21%, 0.8%-21%, 0.9%-21%, 1%-21%, 2%-21%, 3%-21%, 4%-21%, 5%-21%, 6%-21%, 7%-21%, 8%-21%, 9%-21%, 10%-21%, 0.2%-20%, 0.3%-20%, 0.4%-20%, 0.5%-20%, 0.6%-20%, 0.7%-20%, 0.8%-20%, 0.9%-20%, 1%-20%, 2%-20%, 3%-20%, 4%-20%, 5%-20%, 6%-20%, 7%-20%, 8%-20%, 9%-20%, 10%-20%, 0.2%-19%, 0.3%-19%, 0.4%-19%, 0.5%-19%, 0.6%-19%, 0.7%-19%, 0.8%-19%, 0.9%-19%, 1%-19%, 2%-19%, 3%-19%, 4%-19%, 5%-19%, 6%-19%, 7%-19%, 8%-19%, 9%-19%, 10%-19%, 0.2%-18%, 0.3%-18%, 0.4%-18%, 0.5%-18%, 0.6%-18%, 0.7%-18%, 0.8%-18%, 0.9%-18%, 1%-18%, 2%-18%, 3%-18%, 4%-18%, 5%-18%, 6%-18%, 7%-18%, 8%-18%, 9%-18%, 10%-18%, 0.2%-17%, 0.3%-17%, 0.4%-17%, 0.5%-17%, 0.6%-17%, 0.7%-17%, 0.8%-17%, 0.9%-17%, 1%-17%, 2%-17%, 3%-17%, 4%-17%, 5%-17%, 6%-17%, 7%-17%, 8%-17%, 9%-17%, 10%-17%, 0.2%-16%, 0.3%-16%, 0.4%-16%, 0.5%-16%, 0.6%-16%, 0.7%-16%, 0.8%-16%, 0.9%-16%, 1%-16%, 2%-16%, 3%-16%, 4%-16%, 5%-16%, 6%-16%, 7%-16%, 8%-16%, 9%-16%, 10%-16%, 0.2%-15%, 0.3%-15%, 0.4%-15%, 0.5%-15%, 0.6%-15%, 0.7%-15%, 0.8%-15%, 0.9%-15%, 1%-15%, 2%-15%, 3%-15%, 4%-15%, 5%-15%, 6%-15%, 7%-15%, 8%-15%, 9%-15%, 10%-15%, 0.1%-14%, 0.2%-14%, 0.3%-14%, 0.4%-14%, 0.5%-14%, 0.6%-14%, 0.7%-14%, 0.8%-14%, 0.9%-14%, 1%-14%, 2%-14%, 3%-14%, 4%-14%, 5%-14%, 6%-14%, 7%-14%, 8%-14%, 9%-14%, 10%-14%, 0.1%-13%, 0.2%-13%, 0.3%-13%, 0.4%-13%, 0.5%-13%, 0.6%-13%, 0.7%-13%, 0.8%-13%, 0.9%-13%, 1%-13%, 2%-13%, 3%-13%, 4%-13%, 5%-13%, 6%-13%, 7%-13%, 8%-13%, 9%-13%, 10%-13%, 0.1%-12%, 0.2%-12%, 0.3%-12%, 0.4%-12%, 0.5%-12%, 0.6%-12%, 0.7%-12%, 0.8%-12%, 0.9%-12%, 1%-12%, 2%-12%, 3%-12%, 4%-12%, 5%-12%, 6%-12%, 7%-12%, 8%-12%, 9%-12%, 10%-12%, 0.1%-11%, 0.2%-11%, 0.3%-11%, 0.4%-11%, 0.5%-11%, 0.6%-11%, 0.7%-11%, 0.8%-11%, 0.9%-11%, 1%-11%, 2%-11%, 3%-11%, 4%-11%, 5%-11%, 6%-11%, 7%-11%, 8%-11%, 9%-11%, 10%-11%, 0.1%-0.2%, 0.1%-0.3%, 0.1%-0.4%, 0.1%-0.5%, 0.1%-0.6%, 0.1%-0.7%, 0.1%-0.8%, 0.1%-0.9%, 0.1%-1%, 0.1%-2%, 0.1%-3%, 0.1%-4%, 0.1%-5%, 0.1%-6%, 0.1%-7%, 0.1%-8%, or 0.1%-9% more ethanol after 50 hours of fermentation relative to typical yeast strains used for fermentation (e.g., *Saccharomyces* strain Y1609).

In some embodiments, the yeast strains and the derivatives thereof as described herein have a statistically significantly lower glycerol yield than typical yeast strains used for fermentation (e.g., *Saccharomyces* strain Y1609). In some embodiments, the yeast strains and the derivatives thereof as described herein have a statistically significantly lower glycerol yield than typical yeast strains used for fermentation (e.g., *Saccharomyces* strain Y1609) at a temperature from 20° C. to 40° C., preferably from 32° C. to 36° C. In a particular embodiment, the yeast strains and the derivatives thereof as described herein have a statistically significantly lower glycerol yield than typical yeast strains used for fermentation (e.g., *Saccharomyces* strain Y1609) at a temperature of 32° C. In another particular embodiment, the yeast strains and the derivatives thereof as described herein have a statistically significantly lower glycerol yield than typical yeast strains used for fermentation (e.g., *Saccharomyces* strain Y1609) at a temperature of 36° C. The inventors have surprisingly found that the yeast strains described herein result in a statistically significantly lower glycerol production compared to Y1609 under the same fermentation conditions. The inventors have also surprisingly found that the derivatives described herein result in a statistically significantly lower glycerol production compared to Y1609 under the same conditions (e.g., Y1919 in FIGS. 2-5).

In some embodiments, the yeast strains and the derivatives thereof as described herein produce at least about 1%, 2%, 3%, 4%, 5%, 6%, 7%, 8%, 9%, 10%, 11%, 12%, 13%, 14%, 15%, 16%, 17%, 18%, 19%, 20%, 21%, or 22% less glycerol after 50 hours of fermentation relative to typical yeast strains used for fermentation (e.g., *Saccharomyces* strain Y1609). In some embodiments, the yeast strains and the derivatives thereof as described herein produce at most about 10%, 11%, 12%, 13%, 14%, 15%, 16%, 17%, 18%, 19%, 20%, 21%, 22%, 23%, 24%, 25%, 26%, 27%, 28%, 29% or 30% less glycerol after 50 hours of fermentation relative to typical yeast strains used for fermentation (e.g., *Saccharomyces* strain Y1609). In some embodiments, the yeast strains and the derivatives thereof as described herein produce about 1%-30% (i.e. from about 1% to about 30%), 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%, 9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% less glycerol after 50 hours of fermentation relative to typical yeast strains used for fermentation (e.g., *Saccharomyces* strain Y1609).

In some embodiments, the yeast strains and the derivatives thereof as described herein have a higher fermentation rate than typical yeast strains used for fermentation (e.g., *Saccharomyces* strain Y1609). In some embodiments, the yeast strains and the derivatives thereof as described herein have a statistically significantly higher fermentation rate than typical yeast strains used for fermentation (e.g., *Saccharomyces* strain Y1609) at a temperature from 20° C. to 40° C., preferably from 32° C. to 36° C. In a particular embodiment, the yeast strains and the derivatives thereof as described herein have a statistically significantly higher fermentation rate than typical yeast strains used for fermentation (e.g., *Saccharomyces* strain Y1609) at a temperature of 32° C. In another particular embodiment, the yeast strains and the derivatives thereof as described herein have a statistically significantly higher fermentation rate than typical yeast strains used for fermentation (e.g., *Saccharomyces* strain Y1609) at a temperature of 36° C. The inventors have surprisingly found that the yeast strains described herein result in a statistically significantly higher fermentation rate compared to Y1609 under the same fermentation conditions. The inventors have surprisingly found that the derivatives described herein result in a statistically significantly higher fermentation rate compared to Y1609 under the same conditions (e.g., Y1919 in FIGS. 2-5).

In some embodiments, the yeast strains and the derivatives thereof as described herein have a fermentation rate at least about 1%, 2%, 3%, 4%, 5%, 6%, 7%, 8%, 9%, 10%, 11%, 12%, 13%, 14%, 15%, 16%, 17%, 18%, 19%, or 20% higher than typical yeast strains used for fermentation (e.g., *Saccharomyces* strain Y1609) after 24 hours of fermentation. In some embodiments, the yeast strains and the derivatives thereof as described herein have a fermentation rate at most about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% higher than typical yeast strains used for fermentation (e.g., *Saccharomyces* strain Y1609) after 24 hours of fermentation. In some embodiments, the yeast strains and the derivatives thereof as described herein have a fermentation rate about 1%-50% (i.e. from about 1% to about 50%), 2%-50%, 3%-50%, 4%-50%, 5%-50%, 6%-50%, 7%-50%, 8%-50%, 9%-50%, 10%-50%, 11%-50%, 12%-50%, 13%-50%, 14%-50%, 15%-50%, 16%-50%, 17%-50%, 18%-50%, 19%-50%, 20%-50%, 21%-50%, 22%-50%, 23%-50%, 24%-50%, 25%-50%, 26%-50%, 27%-50%, 28%-50%, 2%-49%, 3%-49%, 4%-49%, 5%-49%, 6%-49%, 7%-49%, 8%-49%, 9%-49%, 10%-49%, 11%-49%, 12%-49%, 13%-49%, 14%-49%, 15%-49%, 16%-49%, 17%-49%, 18%-49%, 19%-49%, 20%-49%, 21%-49%, 22%-49%, 23%-49%, 24%-49%, 25%-49%, 26%-49%, 27%-49%, 28%-49%, 2%-48%, 3%-48%, 4%-48%, 5%-48%, 6%-48%, 7%-48%, 8%-48%, 9%-48%, 10%-48%, 11%-48%, 12%-48%, 13%-48%, 14%-48%, 15%-48%, 16%-48%, 17%-48%, 18%-48%, 19%-48%, 20%-48%, 21%-48%, 22%-48%, 23%-48%, 24%-48%, 25%-48%, 26%-48%, 27%-48%, 28%-48%, 2%-47%, 3%-47%, 4%-47%, 5%-47%, 6%-47%, 7%-47%, 8%-47%, 9%-47%, 10%-47%, 11%-47%, 12%-47%, 13%-47%, 14%-47%, 15%-47%, 16%-47%, 17%-47%, 18%-47%, 19%-47%, 20%-47%, 21%-47%, 22%-47%, 23%-47%, 24%-47%, 25%-47%, 26%-47%, 27%-47%, 28%-47%, 2%-46%, 3%-46%, 4%-46%, 5%-46%, 6%-46%, 7%-46%, 8%-46%, 9%-46%, 10%-46%, 11%-46%, 12%-46%, 13%-46%, 14%-46%, 15%-46%, 16%-46%, 17%-46%, 18%-46%, 19%-46%, 20%-46%, 21%-46%, 22%-46%, 23%-46%, 24%-46%, 25%-46%, 26%-46%, 27%-46%, 28%-46%, 2%-45%, 3%-45%, 4%-45%, 5%-45%, 6%-45%, 7%-45%, 8%-45%, 9%-45%, 10%-45%, 11%-45%, 12%-45%, 13%-45%, 14%-45%, 15%-45%, 16%-45%, 17%-45%, 18%-45%, 19%-45%, 20%-45%, 21%-45%, 22%-45%, 23%-45%, 24%-45%, 25%-45%, 26%-45%, 27%-45%, 28%-45%, 2%-44%, 3%-44%, 4%-44%, 5%-44%, 6%-44%, 7%-44%, 8%-44%, 9%-44%, 10%-44%, 11%-44%, 12%-44%, 13%-44%, 14%-44%, 15%-44%, 16%-44%, 17%-44%, 18%-44%, 19%-

44%, 20%-44%, 21%-44%, 22%-44%, 23%-44%, 24%-44%, 25%-44%, 26%-44%, 27%-44%, 28%-44%, 2%-43%, 3%-43%, 4%-43%, 5%-43%, 6%-43%, 7%-43%, 8%-43%, 9%-43%, 10%-43%, 11%-43%, 12%-43%, 13%-43%, 14%-43%, 15%-43%, 16%-43%, 17%-43%, 18%-43%, 19%-43%, 20%-43%, 21%-43%, 22%-43%, 23%-43%, 24%-43%, 25%-43%, 26%-43%, 27%-43%, 28%-43%, 2%-42%, 3%-42%, 4%-42%, 5%-42%, 6%-42%, 7%-42%, 8%-42%, 9%-42%, 10%-42%, 11%-42%, 12%-42%, 13%-42%, 14%-42%, 15%-42%, 16%-42%, 17%-42%, 18%-42%, 19%-42%, 20%-42%, 21%-42%, 22%-42%, 23%-42%, 24%-42%, 25%-42%, 26%-42%, 27%-42%, 28%-42%, 2%-41%, 3%-41%, 4%-41%, 5%-41%, 6%-41%, 7%-41%, 8%-41%, 9%-41%, 10%-41%, 11%-41%, 12%-41%, 13%-41%, 14%-41%, 15%-41%, 16%-41%, 17%-41%, 18%-41%, 19%-41%, 20%-41%, 21%-41%, 22%-41%, 23%-41%, 24%-41%, 25%-41%, 26%-41%, 27%-41%, 28%-41%, 2%-40%, 3%-40%, 4%-40%, 5%-40%, 6%-40%, 7%-40%, 8%-40%, 9%-40%, 10%-40%, 11%-40%, 12%-40%, 13%-40%, 14%-40%, 15%-40%, 16%-40%, 17%-40%, 18%-40%, 19%-40%, 20%-40%, 21%-40%, 22%-40%, 23%-40%, 24%-40%, 25%-40%, 26%-40%, 27%-40%, 28%-40%, 2%-39%, 3%-39%, 4%-39%, 5%-39%, 6%-39%, 7%-39%, 8%-39%, 9%-39%, 10%-39%, 11%-39%, 12%-39%, 13%-39%, 14%-39%, 15%-39%, 16%-39%, 17%-39%, 18%-39%, 19%-39%, 20%-39%, 21%-39%, 22%-39%, 23%-39%, 24%-39%, 25%-39%, 26%-39%, 27%-39%, 28%-39%, 2%-38%, 3%-38%, 4%-38%, 5%-38%, 6%-38%, 7%-38%, 8%-38%, 9%-38%, 10%-38%, 11%-38%, 12%-38%, 13%-38%, 14%-38%, 15%-38%, 16%-38%, 17%-38%, 18%-38%, 19%-38%, 20%-38%, 21%-38%, 22%-38%, 23%-38%, 24%-38%, 25%-38%, 26%-38%, 27%-38%, 28%-38%, 2%-37%, 3%-37%, 4%-37%, 5%-37%, 6%-37%, 7%-37%, 8%-37%, 9%-37%, 10%-37%, 11%-37%, 12%-37%, 13%-37%, 14%-37%, 15%-37%, 16%-37%, 17%-37%, 18%-37%, 19%-37%, 20%-37%, 21%-37%, 22%-37%, 23%-37%, 24%-37%, 25%-37%, 26%-37%, 27%-37%, 28%-37%, 2%-36%, 3%-36%, 4%-36%, 5%-36%, 6%-36%, 7%-36%, 8%-36%, 9%-36%, 10%-36%, 11%-36%, 12%-36%, 13%-36%, 14%-36%, 15%-36%, 16%-36%, 17%-36%, 18%-36%, 19%-36%, 20%-36%, 21%-36%, 22%-36%, 23%-36%, 24%-36%, 25%-36%, 26%-36%, 27%-36%, 28%-36%, 2%-35%, 3%-35%, 4%-35%, 5%-35%, 6%-35%, 7%-35%, 8%-35%, 9%-35%, 10%-35%, 11%-35%, 12%-35%, 13%-35%, 14%-35%, 15%-35%, 16%-35%, 17%-35%, 18%-35%, 19%-35%, 20%-35%, 21%-35%, 22%-35%, 23%-35%, 24%-35%, 25%-35%, 26%-35%, 27%-35%, 28%-35%, 2%-34%, 3%-34%, 4%-34%, 5%-34%, 6%-34%, 7%-34%, 8%-34%, 9%-34%, 10%-34%, 11%-34%, 12%-34%, 13%-34%, 14%-34%, 15%-34%, 16%-34%, 17%-34%, 18%-34%, 19%-34%, 20%-34%, 21%-34%, 22%-34%, 23%-34%, 24%-34%, 25%-34%, 26%-34%, 27%-34%, 28%-34%, 2%-33%, 3%-33%, 4%-33%, 5%-33%, 6%-33%, 7%-33%, 8%-33%, 9%-33%, 10%-33%, 11%-33%, 12%-33%, 13%-33%, 14%-33%, 15%-33%, 16%-33%, 17%-33%, 18%-33%, 19%-33%, 20%-33%, 21%-33%, 22%-33%, 23%-33%, 24%-33%, 25%-33%, 26%-33%, 27%-33%, 28%-33%, 2%-32%, 3%-32%, 4%-32%, 5%-32%, 6%-32%, 7%-32%, 8%-32%, 9%-32%, 10%-32%, 11%-32%, 12%-32%, 13%-32%, 14%-32%, 15%-32%, 16%-32%, 17%-32%, 18%-32%, 19%-32%, 20%-32%, 21%-32%, 22%-32%, 23%-32%, 24%-32%, 25%-32%, 26%-32%, 27%-32%, 28%-32%, 2%-31%, 3%-31%, 4%-31%, 5%-31%, 6%-31%, 7%-31%, 8%-31%, 9%-31%, 10%-31%, 11%-31%, 12%-31%, 13%-31%, 14%-31%, 15%-31%, 16%-31%, 17%-31%, 18%-31%, 19%-31%, 20%-31%, 21%-31%, 22%-31%, 23%-31%, 24%-31%, 25%-31%, 26%-31%, 27%-31%, 28%-31%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%,

9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% higher than typical yeast strains used for fermentation (e.g., *Saccharomyces* strain Y1609) after 24 hours of fermentation.

In some embodiments, the yeast strains and the derivatives thereof as described herein have a statistically significantly higher temperature tolerance than typical yeast strains used for fermentation (e.g., *Saccharomyces* strain Y1609). Temperature tolerance may be exhibited by the increased ethanol production, the decreased glycerol production, and increased fermentation rate. In a particular embodiment, the yeast strains and the derivatives thereof as described herein can tolerate a temperature of about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., and/or about 40° C. The inventors have surprisingly found that the yeast strains and the derivatives thereof described herein have a statistically significantly higher temperature tolerance as compared to Y1609 under the same fermentation conditions.

In some embodiments, the yeast strains and the derivatives thereof as described herein have a statistically significantly higher organic acid tolerance at low pH than typical yeast strains used for fermentation (e.g., *Saccharomyces* strain Y1609). In some embodiments, the yeast strains and the derivatives thereof as described herein have a statistically significantly higher organic acid tolerance than typical yeast strains used for fermentation (e.g., *Saccharomyces* strain Y1609) at a temperature from 20° C. to 40° C., preferably from 32° C. to 36° C. In a particular embodiment, the yeast strains and the derivatives thereof as described herein have a statistically significantly higher organic acid tolerance than typical yeast strains used for fermentation (e.g., *Saccharomyces* strain Y1609) at a temperature of 32° C. In another particular embodiment, the yeast strains and the derivatives thereof as described herein have a statistically significantly higher organic acid tolerance than typical yeast strains used for fermentation (e.g., *Saccharomyces* strain Y1609) at a temperature of 36° C. The inventors have surprisingly found that the yeast strains and the derivatives thereof described herein have a statistically significantly higher organic acid tolerance as compared to Y1609 under the same fermentation conditions. Examples of organic acids include, but are not limited to, lactic acid, acetic acid, succinic acid, citric acid, malic acid, fumaric acid, other carboxylic acids, or combinations thereof.

In some embodiments, the yeast strains and the derivatives thereof as described herein have a statistically significantly higher ethanol yield than typical yeast strains used for fermentation (e.g., *Saccharomyces* strain Y1609) at a temperature from 20° C. to 40° C., preferably from 32° C. to 36° C., and at a low pH with an organic acid. In a particular embodiment, the yeast strains and the derivatives thereof as described herein have a statistically significantly higher ethanol yield than typical yeast strains used for fermentation (e.g., *Saccharomyces* strain Y1609) at a temperature of 32° C. and at a low pH with an organic acid. In another particular embodiment, the yeast strains and the derivatives thereof as described herein have a statistically significantly higher ethanol yield than typical yeast strains used for fermentation (e.g., *Saccharomyces* strain Y1609) at a temperature of 36° C. and at a low pH with an organic acid. The inventors have surprisingly found that the yeast strains described herein result in a statistically significantly higher ethanol yield at a low pH with an organic acid compared to Y1609 under the same fermentation conditions. The inventors have also surprisingly found that the derivatives described herein generally result in a statistically significantly higher ethanol yield at a low pH with an organic acid compared to Y1609 under the same conditions (e.g., Y1919 in FIGS. 2-5).

In some embodiments, the yeast strains and the derivatives thereof as described herein produce at least about 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast strains used for fermentation (e.g., *Saccharomyces* strain Y1609) at a temperature from 20° C. to 40° C., preferably from 32° C. to 36° C., and at a low pH with an organic acid. In some embodiments, the yeast strains and the derivatives thereof as described herein produce at most about 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast strains used for fermentation (e.g., *Saccharomyces* strain Y1609) at a temperature from 20° C. to 40° C., preferably from 32° C. to 36° C., and at a low pH with an organic acid. In some embodiments, the yeast strains and the derivatives thereof as described herein produce about 0.1%-21% (i.e. from about 0.1% to about 21%), 0.2%-21%, 0.3%-21%, 0.4%-21%, 0.5%-21%, 0.6%-21%, 0.7%-21%, 0.8%-21%, 0.9%-21%, 1%-21%, 2%-21%, 3%-21%, 4%-21%, 5%-21%, 6%-21%, 7%-21%, 8%-21%, 9%-21%, 10%-21%, 0.2%-20%, 0.3%-20%, 0.4%-20%, 0.5%-20%, 0.6%-20%, 0.7%-20%, 0.8%-20%, 0.9%-20%, 1%-20%, 2%-20%, 3%-20%, 4%-20%, 5%-20%, 6%-20%, 7%-20%, 8%-20%, 9%-20%, 10%-20%, 0.2%-19%, 0.3%-19%, 0.4%-19%, 0.5%-19%, 0.6%-19%, 0.7%-19%, 0.8%-19%, 0.9%-19%, 1%-19%, 2%-19%, 3%-19%, 4%-19%, 5%-19%, 6%-19%, 7%-19%, 8%-19%, 9%-19%, 10%-19%, 0.2%-18%, 0.3%-18%, 0.4%-18%, 0.5%-18%, 0.6%-18%, 0.7%-18%, 0.8%-18%, 0.9%-18%, 1%-18%, 2%-18%, 3%-18%, 4%-18%, 5%-18%, 6%-18%, 7%-18%, 8%-18%, 9%-18%, 10%-18%, 0.2%-17%, 0.3%-17%, 0.4%-17%, 0.5%-17%, 0.6%-17%, 0.7%-17%, 0.8%-17%, 0.9%-17%, 1%-17%, 2%-17%, 3%-17%, 4%-17%, 5%-17%, 6%-17%, 7%-17%, 8%-17%, 9%-17%, 10%-17%, 0.2%-16%, 0.3%-16%, 0.4%-16%, 0.5%-16%, 0.6%-16%, 0.7%-16%, 0.8%-16%, 0.9%-16%, 1%-16%, 2%-16%, 3%-16%, 4%-16%, 5%-16%, 6%-16%, 7%-16%, 8%-16%, 9%-16%, 10%-16%, 0.2%-15%, 0.3%-15%, 0.4%-15%, 0.5%-15%, 0.6%-15%, 0.7%-15%, 0.8%-15%, 0.9%-15%, 1%-15%, 2%-15%, 3%-15%, 4%-15%, 5%-15%, 6%-15%, 7%-15%, 8%-15%, 9%-15%, 10%-15%, 0.1%-14%, 0.2%-14%, 0.3%-14%, 0.4%-14%, 0.5%-14%, 0.6%-14%, 0.7%-14%, 0.8%-14%, 0.9%-14%, 1%-14%, 2%-14%, 3%-14%, 4%-14%, 5%-14%, 6%-14%, 7%-14%, 8%-14%, 9%-14%, 10%-14%, 0.1%-13%, 0.2%-13%, 0.3%-13%, 0.4%-13%, 0.5%-13%, 0.6%-13%, 0.7%-13%, 0.8%-13%, 0.9%-13%, 1%-13%, 2%-13%, 3%-13%, 4%-13%, 5%-13%, 6%-13%, 7%-13%, 8%-13%, 9%-13%, 10%-13%, 0.1%-12%, 0.2%-

12%, 0.3%-12%, 0.4%-12%, 0.5%-12%, 0.6%-12%, 0.7%-12%, 0.8%-12%, 0.9%-12%, 1%-12%, 2%-12%, 3%-12%, 4%-12%, 5%-12%, 6%-12%, 7%-12%, 8%-12%, 9%-12%, 10%-12%, 0.1%-11%, 0.2%-11%, 0.3%-11%, 0.4%-11%, 0.5%-11%, 0.6%-11%, 0.7%-11%, 0.8%-11%, 0.9%-11%, 1%-11%, 2%-11%, 3%-11%, 4%-11%, 5%-11%, 6%-11%, 7%-11%, 8%-11%, 9%-11%, 10%-11%, 0.1%-0.2%, 0.1%-0.3%, 0.1%-0.4%, 0.1%-0.5%, 0.1%-0.6%, 0.1%-0.7%, 0.1%-0.8%, 0.1%-0.9%, 0.1%-1%, 0.1%-2%, 0.1%-3%, 0.1%-4%, 0.1%-5%, 0.1%-6%, 0.1%-7%, 0.1%-8%, or 0.1%-9% more ethanol after 50 hours of fermentation relative to typical yeast strains used for fermentation (e.g., *Saccharomyces* strain Y1609) at a temperature from 20° C. to 40° C., preferably from 32° C. to 36° C., and at a low pH with an organic acid.

In some embodiments, the yeast strains and the derivatives thereof as described herein have a statistically significantly lower glycerol yield than typical yeast strains used for fermentation (e.g., *Saccharomyces* strain Y1609) at a temperature from 20° C. to 40° C., preferably from 32° C. to 36° C., and at a low pH with an organic acid. In a particular embodiment, the yeast strains and the derivatives thereof as described herein have a statistically significantly lower glycerol yield than typical yeast strains used for fermentation (e.g., *Saccharomyces* strain Y1609) at a temperature of 32° C. and at a low pH with an organic acid. In another particular embodiment, the yeast strains and the derivatives thereof as described herein have a statistically significantly lower glycerol yield than typical yeast strains used for fermentation (e.g., *Saccharomyces* strain Y1609) at a temperature of 36° C. and at a low pH with an organic acid. The inventors have surprisingly found that the yeast strains described herein result in a statistically significantly lower glycerol production at a low pH with an organic acid compared to Y1609 under the same fermentation conditions. The inventors have also surprisingly found that the derivatives described herein result in a statistically significantly lower glycerol production at a low pH with an organic acid compared to Y1609 under the same conditions (e.g., Y1919 in FIGS. 2-5).

In some embodiments, the yeast strains and the derivatives thereof as described herein produce at least about 1%, 2%, 3%, 4%, 5%, 6%, 7%, 8%, 9%, 10%, 11%, 12%, 13%, 14%, 15%, 16%, 17%, 18%, 19%, 20%, 21%, or 22% less glycerol after 50 hours of fermentation relative to typical yeast strains used for fermentation (e.g., *Saccharomyces* strain Y1609) at a temperature from 20° C. to 40° C., preferably from 32° C. to 36° C., and at a low pH with an organic acid. In some embodiments, the yeast strains and the derivatives thereof as described herein produce at most about 10%, 11%, 12%, 13%, 14%, 15%, 16%, 17%, 18%, 19%, 20%, 21%, 22%, 23%, 24%, 25%, 26%, 27%, 28%, 29%, or 30% less glycerol after 50 hours of fermentation relative to typical yeast strains used for fermentation (e.g., *Saccharomyces* strain Y1609) at a temperature from 20° C. to 40° C., preferably from 32° C. to 36° C., and at a low pH with an organic acid. In some embodiments, the yeast strains and the derivatives thereof as described herein produce about 1%-30% (i.e. from about 1% to about 30%), 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%, 9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% less glycerol after 50 hours of fermentation relative to typical yeast strains used for fermentation (e.g., *Saccharomyces* strain Y1609) at a temperature from 20° C. to 40° C., preferably from 32° C. to 36° C., and at a low pH with an organic acid.

In some embodiments, the yeast strains and the derivatives thereof as described herein have a statistically significantly higher fermentation rate than typical yeast strains used for fermentation (e.g., *Saccharomyces* strain Y1609) at a temperature from 20° C. to 40° C., preferably from 32° C. to 36° C., and at a low pH with an organic acid. In a particular embodiment, the yeast strains and the derivatives thereof as described herein have a statistically significantly higher fermentation rate than typical yeast strains used for fermentation (e.g., *Saccharomyces* strain Y1609) at a temperature of 32° C. and at a low pH with an organic acid. In another particular embodiment, the yeast strains and the derivatives thereof as described herein have a statistically significantly higher fermentation rate than typical yeast strains used for fermentation (e.g., *Saccharomyces* strain Y1609) at a temperature of 36° C. and at a low pH with an organic acid. The inventors have surprisingly found that the yeast strains described herein result in a statistically significantly higher fermentation rate at a low pH with an organic acid compared to Y1609 under the same fermentation conditions. The inventors have surprisingly found that the derivatives described herein result in a statistically significantly higher fermentation rate at a low pH with an organic acid compared to Y1609 under the same conditions (e.g., Y1919 in FIGS. 2-5).

In some embodiments, the yeast strains and the derivatives thereof as described herein have a fermentation rate at least about 1%, 2%, 3%, 4%, 5%, 6%, 7%, 8%, 9%, 10%, 11%, 12%, 13%, 14%, 15%, 16%, 17%, 18%, 19%, or 20% higher than typical yeast strains used for fermentation (e.g., *Saccharomyces* strain Y1609) after 24 hours of fermentation at a temperature from 20° C. to 40° C., preferably from 32° C. to 36° C., and at a low pH with an organic acid. In some embodiments, the yeast strains and the derivatives thereof as described herein have a fermentation rate at most about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% higher than typical yeast strains used for fermentation (e.g., *Saccharomyces* strain Y1609) after 24 hours of fermentation at a temperature from 20° C. to 40° C., preferably from 32° C. to 36° C., and at a low pH with an organic acid. In some embodiments, the yeast strains and the derivatives thereof as described herein have a fermentation rate about 1%-50% (i.e. from about 1% to about 50%), 2%-50%, 3%-50%, 4%-50%, 5%-50%, 6%-50%, 7%-50%, 8%-50%, 9%-50%, 10%-50%, 11%-50%, 12%-50%, 13%-50%, 14%-50%, 15%-50%, 16%-50%, 17%-50%, 18%-50%, 19%-50%, 20%-50%, 21%-50%, 22%-50%, 23%-50%, 24%-50%, 25%-50%, 26%-50%, 27%-50%, 28%-50%, 2%-49%, 3%-49%, 4%-49%, 5%-49%, 6%-49%, 7%-49%, 8%-49%, 9%-49%, 10%-49%, 11%-49%, 12%-49%, 13%-49%, 14%-49%, 15%-49%, 16%-49%, 17%-49%, 18%-49%, 19%-49%, 20%-49%, 21%-49%, 22%-49%, 23%-49%, 24%-49%, 25%-49%, 26%-49%, 27%-49%, 28%-49%, 2%-48%, 3%-48%, 4%-48%, 5%-48%, 6%-48%, 7%-48%, 8%-48%, 9%-48%, 10%-48%, 11%-48%, 12%-48%, 13%-48%, 14%-48%, 15%-48%, 16%-48%, 17%-48%, 18%-48%, 19%-48%, 20%-48%, 21%-48%, 22%-48%, 23%-48%, 24%-48%, 25%-48%, 26%-48%, 27%-48%, 28%-48%, 2%-47%, 3%-47%, 4%-47%, 5%-47%, 6%-47%, 7%-47%, 8%-47%, 9%-47%, 10%-47%, 11%-47%, 12%-47%, 13%-47%, 14%-47%, 15%-47%, 16%-47%, 17%-47%, 18%-47%, 19%-47%, 20%-47%, 21%-47%, 22%-47%, 23%-47%, 24%-47%, 25%-47%, 26%-47%, 27%-47%, 28%-47%, 2%-46%, 3%-46%, 4%-46%, 5%-46%, 6%-46%, 7%-46%, 8%-46%, 9%-46%, 10%-46%, 11%-46%, 12%-46%, 13%-46%, 14%-46%, 15%-46%, 16%-46%, 17%-46%, 18%-46%, 19%-46%, 20%-46%, 21%-46%, 22%-46%, 23%-46%, 24%-46%, 25%-46%, 26%-46%, 27%-46%, 28%-46%, 2%-45%, 3%-45%, 4%-45%, 5%-45%, 6%-45%, 7%-45%, 8%-45%, 9%-45%, 10%-45%, 11%-45%, 12%-45%, 13%-45%, 14%-45%, 15%-45%, 16%-45%, 17%-45%, 18%-45%, 19%-45%, 20%-45%, 21%-45%, 22%-45%, 23%-45%, 24%-45%, 25%-45%, 26%-45%, 27%-45%, 28%-45%, 2%-44%, 3%-44%, 4%-44%, 5%-44%, 6%-44%, 7%-44%, 8%-44%, 9%-44%, 10%-44%, 11%-44%, 12%-44%, 13%-44%, 14%-44%, 15%-44%, 16%-44%, 17%-44%, 18%-44%, 19%-44%, 20%-44%, 21%-44%, 22%-44%, 23%-44%, 24%-44%, 25%-44%, 26%-44%, 27%-44%, 28%-44%, 2%-43%, 3%-43%, 4%-43%, 5%-43%, 6%-43%, 7%-43%, 8%-43%, 9%-43%, 10%-43%, 11%-43%, 12%-43%, 13%-43%, 14%-43%, 15%-43%, 16%-43%, 17%-43%, 18%-43%, 19%-43%, 20%-43%, 21%-43%, 22%-43%, 23%-43%, 24%-43%, 25%-43%, 26%-43%, 27%-43%, 28%-43%, 2%-42%, 3%-42%, 4%-42%, 5%-42%, 6%-42%, 7%-42%, 8%-42%, 9%-42%, 10%-42%, 11%-42%, 12%-42%, 13%-42%, 14%-42%, 15%-42%, 16%-42%, 17%-42%, 18%-42%, 19%-42%, 20%-42%, 21%-42%, 22%-42%, 23%-42%, 24%-42%, 25%-42%, 26%-42%, 27%-42%, 28%-42%, 2%-41%, 3%-41%, 4%-41%, 5%-41%, 6%-41%, 7%-41%, 8%-41%, 9%-41%, 10%-41%, 11%-41%, 12%-41%, 13%-41%, 14%-41%, 15%-41%, 16%-41%, 17%-41%, 18%-41%, 19%-41%, 20%-41%, 21%-41%, 22%-41%, 23%-41%, 24%-41%, 25%-41%, 26%-41%, 27%-41%, 28%-41%, 2%-40%, 3%-40%, 4%-40%, 5%-40%, 6%-40%, 7%-40%, 8%-40%, 9%-40%, 10%-40%, 11%-40%, 12%-40%, 13%-40%, 14%-40%, 15%-40%, 16%-40%, 17%-40%, 18%-40%, 19%-40%, 20%-40%, 21%-40%, 22%-40%, 23%-40%, 24%-40%, 25%-40%, 26%-40%, 27%-40%, 28%-40%, 2%-39%, 3%-39%, 4%-39%, 5%-39%, 6%-39%, 7%-39%, 8%-39%, 9%-39%, 10%-39%, 11%-39%, 12%-39%, 13%-39%, 14%-39%, 15%-39%, 16%-39%, 17%-39%, 18%-39%, 19%-39%, 20%-39%, 21%-39%, 22%-39%, 23%-39%, 24%-39%, 25%-39%, 26%-39%, 27%-39%, 28%-39%, 2%-38%, 3%-38%, 4%-38%, 5%-38%, 6%-38%, 7%-38%, 8%-38%, 9%-38%, 10%-38%, 11%-38%, 12%-38%, 13%-38%, 14%-38%, 15%-38%, 16%-38%, 17%-38%, 18%-38%, 19%-38%, 20%-38%, 21%-38%, 22%-38%, 23%-38%, 24%-38%, 25%-38%, 26%-38%, 27%-38%, 28%-38%, 2%-37%, 3%-37%, 4%-37%, 5%-37%, 6%-37%, 7%-37%, 8%-37%, 9%-37%, 10%-37%, 11%-37%, 12%-37%, 13%-37%, 14%-37%, 15%-37%, 16%-37%, 17%-37%, 18%-37%, 19%-37%, 20%-37%, 21%-37%, 22%-37%, 23%-37%, 24%-37%, 25%-37%, 26%-37%, 27%-37%, 28%-37%, 2%-36%, 3%-36%, 4%-36%, 5%-36%, 6%-36%, 7%-36%, 8%-36%, 9%-36%, 10%-36%, 11%-36%, 12%-36%, 13%-36%, 14%-36%, 15%-36%, 16%-36%, 17%-36%, 18%-36%, 19%-36%, 20%-36%, 21%-36%, 22%-36%, 23%-36%, 24%-36%, 25%-36%, 26%-36%, 27%-36%, 28%-36%, 2%-35%, 3%-35%, 4%-35%, 5%-35%, 6%-35%, 7%-35%, 8%-35%, 9%-35%, 10%-35%, 11%-35%, 12%-35%, 13%-35%, 14%-35%, 15%-35%, 16%-35%, 17%-35%, 18%-35%, 19%-35%, 20%-35%, 21%-35%, 22%-35%, 23%-35%, 24%-35%, 25%-35%, 26%-35%, 27%-35%, 28%-35%, 2%-34%, 3%-34%, 4%-34%, 5%-34%, 6%-34%, 7%-34%, 8%-34%, 9%-34%, 10%-34%, 11%-34%, 12%-34%, 13%-34%, 14%-34%, 15%-34%, 16%-34%, 17%-34%, 18%-34%, 19%-34%, 20%-34%, 21%-34%, 22%-34%, 23%-34%, 24%-34%, 25%-34%, 26%-34%, 27%-34%, 28%-34%, 2%-33%, 3%-33%, 4%-33%, 5%-33%, 6%-33%, 7%-33%, 8%-33%, 9%-33%, 10%-33%, 11%-33%, 12%-33%, 13%-33%, 14%-33%, 15%-33%, 16%-33%, 17%-33%, 18%-33%, 19%-33%, 20%-33%, 21%-33%, 22%-33%, 23%-33%, 24%-33%, 25%-33%, 26%-33%, 27%-33%, 28%-33%, 2%-32%, 3%-32%, 4%-32%, 5%-32%, 6%-32%, 7%-32%, 8%-32%, 9%-32%, 10%-32%, 11%-32%, 12%-32%, 13%-32%, 14%-32%, 15%-32%, 16%-32%, 17%-32%, 18%-32%, 19%-32%, 20%-32%, 21%-32%, 22%-32%, 23%-32%, 24%-32%, 25%-32%, 26%-32%, 27%-32%, 28%-32%, 2%-31%, 3%-31%, 4%-31%, 5%-31%, 6%-31%, 7%-31%, 8%-31%, 9%-31%, 10%-31%, 11%-31%, 12%-31%, 13%-31%, 14%-31%, 15%-31%, 16%-31%, 17%-31%, 18%-31%, 19%-31%, 20%-31%, 21%-31%, 22%-31%, 23%-31%, 24%-31%, 25%-31%, 26%-31%, 27%-31%, 28%-31%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%, 9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% higher than typical yeast strains used for fermentation (e.g., *Saccharomyces* strain Y1609) after 24 hours of fermentation at a temperature from 20° C. to 40° C., preferably from 32° C. to 36° C., and at a low pH with an organic acid.

In some embodiments, the yeast strains and the derivatives thereof as described herein have one or more of the defining characteristics described herein. In some embodiments, the yeast strains and the derivatives thereof as described herein have one or more of the defining characteristics described herein at a temperature from 20° C. to 40° C., preferably from 32° C. to 36° C., and at a low pH with an organic acid. In some embodiments, the yeast strains and the derivatives thereof as described herein have one or more of the defining characteristics described herein at a temperature from 20° C. to 40° C., preferably from 32° C. to 36° C., and at a normal pH without an organic acid. For example, in some embodiments, the yeast strains and the derivatives thereof as described herein have a statistically significantly higher ethanol yield, a statistically significantly lower glycerol yield, a statistically significantly higher fermentation rate, a statistically significantly higher temperature tolerance, and a statistically significantly higher organic acid tolerance than typical yeast strains used for fermentation (e.g., *Saccharomyces* strain Y1609); in some embodiments, the yeast strains and the derivatives thereof as described herein have a statistically significantly higher fermentation rate, produce lower levels of glycerol, and have a statistically significantly higher ethanol yield than typical yeast strains used for fermentation (e.g., *Saccharomyces* strain Y1609); in some embodiments, the yeast strains and the derivatives thereof as described herein have a statistically significantly higher fermentation rate and produce statistically significantly lower levels of glycerol than typical yeast strains used for fermentation (e.g., *Saccharomyces* strain Y1609).

The yeast strains and the derivatives thereof as described herein may be in any viable form, including crumbled, dry (including active dry and instant), compressed, cream form, etc. In a particular embodiment, the *Saccharomyces cerevisiae* yeast strain or derivative thereof is dry yeast, such as active dry yeast. In another particular embodiment, the *Saccharomyces cerevisiae* yeast strain or derivative thereof is a compressed yeast. In another embodiment, the *Saccharomyces cerevisiae* yeast strain or derivative thereof is a cream yeast.

a. Yeast Strains

One embodiment described herein are *Saccharomyces* yeast strains designated: Y1912 (deposited under NRRL Patent Deposit Designation No. Y-68003); Y1913 (deposited under NRRL Patent Deposit Designation No. Y-68004); Y1914 (deposited under NRRL Patent Deposit Designation No. Y-68005); Y1919 (deposited under NRRL Patent Deposit Designation No. Y-68006); Y1923 (deposited under NRRL Patent Deposit Designation No. Y-68007); Y1927 (deposited under NRRL Patent Deposit Designation No. Y-68008); Y1929 (deposited under NRRL Patent Deposit Designation No. Y-68009). These yeast strains are referred to herein as "the yeast strains", "the *Saccharomyces* yeast strains", or by their designations (i.e. "Y1912" or "H041"; "Y1913" or "H136"; "Y1914" or "H138"; "Y1919" or "H172"; "Y1923" or "H237"; "Y1927" or "MM2E2A3"; "Y1929" or "MM2E3A1"). The yeast strains (i.e. Y1912, Y1913, Y1914, Y1919, Y1923, Y1927, and Y1929) were produced from one or more different *Saccharomyces* yeast strains by one or more of the methods as shown in FIG. 1. In one aspect, the yeast strains described herein comprise one or more defining characteristics including a higher ethanol production, lower glycerol production, higher temperature tolerance, higher organic acid tolerance, and higher fermentation rates than other yeast strains and typical yeast strains used for fermentation, in particular in comparison to the yeast strain Y1609, the yeast strain used in the product Fali. Representative samples of the yeast strains have been deposited under the above-identified accession numbers at the Agricultural Research Service Patent Culture Collection (NRRL), Northern Regional Research Center, 1815 University Street, Peoria, IL, USA.

b. Yeast Strain Derivatives

Another embodiment described herein is a derivative of a *Saccharomyces* yeast strain selected from the *Saccharomyces* yeast strains designated: Y1912 (deposited under NRRL Patent Deposit Designation No. Y-68003); Y1913 (deposited under NRRL Patent Deposit Designation No. Y-68004); Y1914 (deposited under NRRL Patent Deposit Designation No. Y-68005); Y1919 (deposited under NRRL Patent Deposit Designation No. Y-68006); Y1923 (deposited under NRRL Patent Deposit Designation No. Y-68007); Y1927 (deposited under NRRL Patent Deposit Designation No. Y-68008); Y1929 (deposited under NRRL Patent Deposit Designation No. Y-68009). In one aspect, the derivatives comprise one or more defining characteristics including a higher ethanol production, lower glycerol production, higher temperature tolerance, higher organic acid tolerance, and higher fermentation rates than other yeast strains and typical yeast strains used for fermentation, in particular in comparison to the yeast strain Y1609, the yeast strain used in the product Fali. In another aspect, the derivative can be a parental strain and be used to generate other derivatives. For example, Y1912 is a derivative of two strains, but is also a parental strain (e.g., Y1912 was mated with a second strain to make the Y1913 strain).

c. Mutant Yeast and Derivatives

Another embodiment described herein is a mutant of a *Saccharomyces* yeast strain selected from the *Saccharomyces* yeast strains designated: Y1912 (deposited under NRRL Patent Deposit Designation No. Y-68003); Y1913 (deposited under NRRL Patent Deposit Designation No. Y-68004); Y1914 (deposited under NRRL Patent Deposit Designation No. Y-68005); Y1919 (deposited under NRRL Patent Deposit Designation No. Y-68006); Y1923 (deposited under NRRL Patent Deposit Designation No. Y-68007); Y1927 (deposited under NRRL Patent Deposit Designation No. Y-68008); Y1929 (deposited under NRRL Patent Deposit Designation No. Y-68009) or derivative thereof. In an embodiment, the *Saccharomyces* yeast strains designated Y1912, Y1913, Y1914, Y1919, Y1923, Y1927, and Y1929 may be derived from one or more different *Saccharomyces* yeast strains by the process shown in FIG. 1D, so that one or more of Y1912, Y1913, Y1914, Y1919, Y1923, Y1927, or Y1929 may be a mutant yeast strain. In one aspect, the mutant yeast strains and mutant derivatives comprise one or more defining characteristics including a higher ethanol production, lower glycerol production, higher temperature tolerance, higher organic acid tolerance, and higher fermentation rates than other yeast strains and typical yeast strains used for fermentation, in particular in comparison to the yeast strain Y1609, the yeast strain used in the product Fali. In another aspect, the mutant yeast strains and mutant derivatives can be a parental strain and be used to generate other derivatives. An example of mutagenesis is provided in FIG. 1D. In an embodiment, the mutant yeast strains and mutant derivatives as described herein were derived from the method shown in FIG. 1D.

The mutant yeast strains and mutant derivatives may be made by contacting any of the yeast strains described herein with a mutagen. The mutagen may be any mutagen known in the art. For example, the mutagen may be ethyl methanesulfonate (EMS), ultraviolet light (UV), X-rays, methylmethane sulphonate (MMS), nitrous acid, nitrosoguanidine (NNG), acridine mustard, 2-methoxy-6-chloro-9[3-(ethyl-2-chloroethyl)aminopropylamino]acridine•2 (ICR-170), nitrogen mustard, etc.

d. Evolved Yeast and Derivatives

Another embodiment described herein is an evolved yeast strain or derivative of a *Saccharomyces* yeast strain selected from the *Saccharomyces* yeast strains designated: Y1912 (deposited under NRRL Patent Deposit Designation No. Y-68003); Y1913 (deposited under NRRL Patent Deposit Designation No. Y-68004); Y1914 (deposited under NRRL Patent Deposit Designation No. Y-68005); Y1919 (deposited under NRRL Patent Deposit Designation No. Y-68006); Y1923 (deposited under NRRL Patent Deposit Designation No. Y-68007); Y1927 (deposited under NRRL Patent Deposit Designation No. Y-68008); Y1929 (deposited under NRRL Patent Deposit Designation No. Y-68009). In an embodiment, the *Saccharomyces* yeast strains designated Y1912, Y1913, Y1914, Y1919, Y1923, Y1927, and Y1929 may be derived from one or more different *Saccharomyces* yeast strains by the process shown in FIG. 1C, so that one or more of Y1912, Y1913, Y1914, Y1919, Y1923, Y1927, or Y1929 may be an evolved yeast strain. In one aspect, the evolved yeast strains and evolved derivatives comprise one or more defining characteristics including a higher ethanol production, lower glycerol production, higher temperature tolerance, higher organic acid tolerance, and higher fermentation rates than other yeast strains and typical yeast strains used for fermentation, in particular in comparison to the yeast strain Y1609, the yeast strain used in the product Fali. In another aspect, the evolved yeast strains and evolved derivatives can be a parental strain and be used to generate other derivatives. An example of evolution is provided in FIG. 1C. In an embodiment, the evolved yeast strains and evolved derivatives as described herein were derived from the method shown in FIG. 1C.

The evolved yeast strains and evolved derivatives may be made by applying selection pressure to any of the yeast strains described herein. The selection pressure can be negative (decreases the occurrence of a trait) or positive (increases the proportion of a trait). The selection pressure may be constant or may be intermittent. The selection pressure may be applied by altering the presence of resources (e.g., starches and sugars) and/or altering environmental conditions (e.g., temperature, the presence of organic acids, pH, and length of fermentation).

e. Recombinant Yeast and Derivatives

An additional embodiment described herein is recombinant yeast strains and recombination derivatives. The recombinant yeast strains and derivatives may be derived from the *Saccharomyces cerevisiae* yeast strains or derivatives thereof described herein. The recombinant yeast strain may comprise a modification to suppress expression of a gene, enhance expression of a gene, introduce a gene, delete a gene, or modify the sequence of a gene. An aspect described herein is a method of making a recombinant of the yeast strain or derivative thereof. The method may comprise introducing a nucleic acid into the *Saccharomyces* yeast described herein using recombinant DNA technology. Methods for the introduction of nucleic acids into *Saccharomyces* yeast cells, and in particular strains of *Saccharomyces*, are known in the art and are described in, for example, Ausubel et al. (1997), *Current Protocols in Molecular Biology,* 2:13.7.1-13.7.7 and Yang and Blenner, (2020), *Curr Opin Biotechnol.,* 66:255-266, both incorporated by reference herein. The method may comprise changing the nucleic acid sequence of the *Saccharomyces* yeast or derivatives described herein using gene editing or similar technology.

3. COMPOSITIONS

Further provided herein are compositions comprising the above-described yeast strains or the derivatives thereof. In an embodiment, a composition may comprise at least one of the yeast strains described herein, the derivatives described herein, or a combination thereof, and a naturally occurring and/or a non-naturally occurring component. For example, the composition may comprise one or more components selected from surfactants, emulsifiers, gums, swelling agents, antioxidants, starches, metabolites, and other processing aids. In an embodiment, a composition may comprise a dry yeast of any of the yeast strains and/or the derivatives thereof, starches, and emulsifiers. In another embodiment, a composition may comprise a cream yeast of any of the yeast strains and/or the derivatives thereof, glycerol, and xanthan gum. In an embodiment an enriched culture of any of the yeast strains described herein is provided wherein enriched is 90%-99% pure. In another embodiment, a pure culture of any of the yeast strains described herein is provided wherein pure is 100% pure and thus no additional yeasts present.

The composition may comprise a *Saccharomyces* yeast as described herein, and any suitable surfactant. In an embodiment the surfactant(s) is/are an anionic surfactant, cationic surfactant, and/or nonionic surfactant.

The composition may comprise a *Saccharomyces* yeast as described herein, and any suitable emulsifier. In an embodiment the emulsifier is a fatty-acid ester of sorbitan. In an embodiment the emulsifier is selected from the group of sorbitan monostearate (SMS), citric acid esters of mono-diglycerides, polyglycerolester, and fatty acid esters of propylene glycol.

The composition may comprise a *Saccharomyces* yeast as described herein, and Olindronal SMS, Olindronal SK, or Olindronal SPL including a composition concerned in European Patent No. 1,724,336. These products are commercially available from Bussetti, Austria, for active dry yeast.

The composition may comprise a *Saccharomyces* yeast as described herein, and any suitable gum. In an embodiment the gum is acacia gum, in particular for cream, compressed and dry yeast.

The composition may comprise a *Saccharomyces* yeast as described herein, and any suitable swelling agent. In an embodiment the swelling agent is methyl cellulose or carboxymethyl cellulose.

The composition may comprise a *Saccharomyces* yeast as described herein, and any suitable antioxidant. In an embodiment the antioxidant is butylated hydroxyanisol (BHA) and/or butylated hydroxytoluene (BHT), or ascorbic acid (vitamin C), in particular for active dry yeast.

The composition may comprise a *Saccharomyces* yeast as described herein, and any suitable starch. In an embodiment the starch is potato starch, corn starch, or pea starch.

The composition may comprise a *Saccharomyces* yeast as described herein, and any suitable yeast protectant. In an embodiment the protectant is glycerol.

a. Composition Characteristics

In one aspect, the composition comprises one or more defining characteristics including a higher ethanol production, lower glycerol production, higher temperature tolerance, higher organic acid tolerance, and higher fermentation rates than other yeast products and typical yeast products used for fermentation, in particular in comparison to the yeast product Fali. In addition, the compositions described herein can be readily distinguished from other yeast products used in the ethanol industry that do not have the ethanol producing capabilities and defining characteristics of the compositions described herein.

In some embodiments, the compositions as described herein have a higher ethanol yield than typical yeast products used for fermentation (e.g., Fali, Ethanol Red®, Thermosacc®, Angel Super Alcohol®). In some embodiments, the compositions as described herein have a higher ethanol yield than typical yeast products used for fermentation (e.g., Fali, Ethanol Red®, Thermosacc®, Angel Super Alcohol®) at a temperature from 20° C. to 40° C., preferably from 32° C. to 36° C. In a particular embodiment, the compositions as described herein have a higher ethanol yield than typical yeast products used for fermentation (e.g., Fali, Ethanol Red®, Thermosacc®, Angel Super Alcohol®) at a temperature of 32° C. In another particular embodiment, the compositions as described herein have a higher ethanol yield than typical yeast products used for fermentation (e.g., Fali, Ethanol Red®, Thermosacc®, Angel Super Alcohol®) at a temperature of 36° C.

In some embodiments, the compositions as described herein produce at least about 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast products used for fermentation (e.g., Fali, Ethanol Red®, Thermosacc®, Angel Super Alcohol®). In some embodiments, the compositions as described herein produce at most about 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast products used for fermentation (e.g., Fali, Ethanol Red®, Thermosacc®, Angel Super Alcohol®). In some embodiments, the compositions as described herein produce about 0.1%-21% (i.e. from about 0.1% to about 21%), 0.2%-21%, 0.3%-21%, 0.4%-21%, 0.5%-21%, 0.6%-21%, 0.7%-21%, 0.8%-21%, 0.9%-21%, 1%-21%, 2%-21%, 3%-21%, 4%-21%, 5%-21%, 6%-21%, 7%-21%, 8%-21%, 9%-21%, 10%-21%, 0.2%-20%, 0.3%-20%, 0.4%-20%, 0.5%-20%, 0.6%-20%, 0.7%-20%, 0.8%-20%, 0.9%-20%, 1%-20%, 2%-20%, 3%-20%, 4%-20%, 5%-20%, 6%-20%, 7%-20%, 8%-20%, 9%-20%, 10%-20%, 0.2%-19%, 0.3%-19%, 0.4%-19%, 0.5%-19%, 0.6%-19%, 0.7%-19%, 0.8%-19%, 0.9%-19%, 1%-19%, 2%-19%, 3%-19%, 4%-19%, 5%-19%, 6%-19%, 7%-19%, 8%-19%, 9%-19%, 10%-19%, 0.2%-18%, 0.3%-18%, 0.4%-18%, 0.5%-18%, 0.6%-18%, 0.7%-18%, 0.8%-18%, 0.9%-18%, 1%-18%, 2%-18%, 3%-18%, 4%-18%, 5%-18%, 6%-18%, 7%-18%, 8%-18%, 9%-18%, 10%-18%, 0.2%-17%, 0.3%-17%, 0.4%-17%, 0.5%-17%, 0.6%-17%, 0.7%-17%, 0.8%-17%, 0.9%-17%, 1%-17%, 2%-17%, 3%-17%, 4%-17%, 5%-17%, 6%-17%, 7%-17%, 8%-17%, 9%-17%, 10%-17%, 0.2%-16%, 0.3%-16%, 0.4%-16%, 0.5%-16%, 0.6%-16%, 0.7%-16%, 0.8%-16%, 0.9%-16%, 1%-16%, 2%-16%, 3%-16%, 4%-16%, 5%-16%, 6%-16%, 7%-16%, 8%-16%, 9%-16%, 10%-16%, 0.2%-15%, 0.3%-15%, 0.4%-15%, 0.5%-15%, 0.6%-15%, 0.7%-15%, 0.8%-15%, 0.9%-15%, 1%-15%, 2%-15%, 3%-15%, 4%-15%, 5%-15%, 6%-15%, 7%-15%, 8%-15%, 9%-15%, 10%-15%, 0.1%-14%, 0.2%-14%, 0.3%-14%, 0.4%-14%, 0.5%-14%, 0.6%-14%, 0.7%-14%, 0.8%-14%, 0.9%-14%, 1%-14%, 2%-14%, 3%-14%, 4%-14%, 5%-14%, 6%-14%, 7%-14%, 8%-14%, 9%-14%, 10%-14%, 0.1%-13%, 0.2%-13%, 0.3%-13%, 0.4%-13%, 0.5%-13%, 0.6%-13%, 0.7%-13%, 0.8%-13%, 0.9%-13%, 1%-13%, 2%-13%, 3%-13%, 4%-13%, 5%-13%, 6%-13%, 7%-13%, 8%-13%, 9%-13%, 10%-13%, 0.1%-12%, 0.2%-12%, 0.3%-12%, 0.4%-12%, 0.5%-12%, 0.6%-12%, 0.7%-12%, 0.8%-12%, 0.9%-12%, 1%-12%, 2%-12%, 3%-12%, 4%-12%, 5%-12%, 6%-12%, 7%-12%, 8%-12%, 9%-12%, 10%-12%, 0.1%-11%, 0.2%-11%, 0.3%-11%, 0.4%-11%, 0.5%-11%, 0.6%-11%, 0.7%-11%, 0.8%-11%, 0.9%-11%, 1%-11%, 2%-11%, 3%-11%, 4%-11%, 5%-11%, 6%-11%, 7%-11%, 8%-11%, 9%-11%, 10%-11%, 0.1%-0.2%, 0.1%-0.3%, 0.1%-0.4%, 0.1%-0.5%, 0.1%-0.6%, 0.1%-0.7%, 0.1%-0.8%, 0.1%-0.9%, 0.1%-1%, 0.1%-2%, 0.1%-3%, 0.1%-4%, 0.1%-5%, 0.1%-6%, 0.1%-7%, 0.1%-8%, or 0.1%-9% more ethanol after 50 hours of fermentation relative to typical yeast products used for fermentation (e.g., Fali, Ethanol Red®, Thermosacc®, Angel Super Alcohol®).

In some embodiments, the compositions as described herein have a lower glycerol yield than typical yeast products used for fermentation (e.g., Fali, Ethanol Red®, Thermosacc®, Angel Super Alcohol®). In some embodiments, the compositions as described herein have a lower glycerol yield than typical yeast products used for fermentation (e.g., Fali, Ethanol Red®, Thermosacc®, Angel Super Alcohol®) at a temperature from 20° C. to 40° C., preferably from 32° C. to 36° C. In a particular embodiment, the compositions as described herein have a lower glycerol yield than typical yeast products used for fermentation (e.g., Fali, Ethanol Red®, Thermosacc®, Angel Super Alcohol®) at a temperature of 32° C. In another particular embodiment, the compositions as described herein have a lower glycerol yield than typical yeast products used for fermentation (e.g., Fali, Ethanol Red®, Thermosacc®, Angel Super Alcohol®) at a temperature of 36° C.

In some embodiments, the compositions as described herein produce at least about 1%, 2%, 3%, 4%, 5%, 6%, 7%, 8%, 9%, 10%, 11%, 12%, 13%, 14%, 15%, 16%, 17%, 18%, 19%, 20%, 21%, or 22% less glycerol after 50 hours of fermentation relative to typical yeast products used for fermentation (e.g., Fali, Ethanol Red®, Thermosacc®, Angel Super Alcohol®). In some embodiments, the compositions as described herein produce at most about 10%, 11%, 12%, 13%, 14%, 15%, 16%, 17%, 18%, 19%, 20%, 21%, 22%, 23%, 24%, 25%, 26%, 27%, 28%, 29%, or 30% less glycerol after 50 hours of fermentation relative to typical yeast products used for fermentation (e.g., Fali, Ethanol Red®, Thermosacc®, Angel Super Alcohol®). In some embodiments, the yeast strains and the derivatives thereof as described herein produce about 1%-30% (i.e. from about 1% to about 30%), 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-

20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%, 9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% less glycerol after 50 hours of fermentation relative to typical yeast products used for fermentation (e.g., Fali, Ethanol Red®, Thermosacc®, Angel Super Alcohol®).

In some embodiments, the compositions as described herein have a higher fermentation rate than typical yeast products used for fermentation (e.g., Fali, Ethanol Red®, Thermosacc®, Angel Super Alcohol®). In some embodiments, the compositions as described herein have a higher fermentation rate than typical yeast products used for fermentation (e.g., Fali, Ethanol Red®, Thermosacc®, Angel Super Alcohol®) at a temperature from 20° C. to 40° C., preferably from 32° C. to 36° C. In a particular embodiment, the compositions as described herein have a higher fermentation rate than typical yeast products used for fermentation (e.g., Fali, Ethanol Red®, Thermosacc®, Angel Super Alcohol®) at a temperature of 32° C. In another particular embodiment, the compositions as described herein have a higher fermentation rate than typical yeast products used for fermentation (e.g., Fali, Ethanol Red®, Thermosacc®, Angel Super Alcohol®) at a temperature of 36° C.

In some embodiments, the compositions as described herein have a fermentation rate at least about 1%, 2%, 3%, 4%, 5%, 6%, 7%, 8%, 9%, 10%, 11%, 12%, 13%, 14%, 15%, 16%, 17%, 18%, 19%, or 20% higher than typical yeast products used for fermentation (e.g., Fali, Ethanol Red®, Thermosacc®, Angel Super Alcohol®) after 24 hours of fermentation. In some embodiments, the compositions as described herein have a fermentation rate at most about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% higher than typical yeast products used for fermentation (e.g., Fali, Ethanol Red®, Thermosacc®, Angel Super Alcohol®) after 24 hours of fermentation. In some embodiments, the compositions as described herein have a fermentation rate about 1%-50% (i.e. from about 1% to about 50%), 2%-50%, 3%-50%, 4%-50%, 5%-50%, 6%-50%, 7%-50%, 8%-50%, 9%-50%, 10%-50%, 11%-50%, 12%-50%, 13%-50%, 14%-50%, 15%-50%, 16%-50%, 17%-50%, 18%-50%, 19%-50%, 20%-50%, 21%-50%, 22%-50%, 23%-50%, 24%-50%, 25%-50%, 26%-50%, 27%-50%, 28%-50%, 2%-49%, 3%-49%, 4%-49%, 5%-49%, 6%-49%, 7%-49%, 8%-49%, 9%-49%, 10%-49%, 11%-49%, 12%-49%, 13%-49%, 14%-49%, 15%-49%, 16%-49%, 17%-49%, 18%-49%, 19%-49%, 20%-49%, 21%-49%, 22%-49%, 23%-49%, 24%-49%, 25%-49%, 26%-49%, 27%-49%, 28%-49%, 2%-48%, 3%-48%, 4%-48%, 5%-48%, 6%-48%, 7%-48%, 8%-48%, 9%-48%, 10%-48%, 11%-48%, 12%-48%, 13%-48%, 14%-48%, 15%-48%, 16%-48%, 17%-48%, 18%-48%, 19%-48%, 20%-48%, 21%-48%, 22%-48%, 23%-48%, 24%-48%, 25%-48%, 26%-48%, 27%-48%, 28%-48%, 2%-47%, 3%-47%, 4%-47%, 5%-47%, 6%-47%, 7%-47%, 8%-47%, 9%-47%, 10%-47%, 11%-47%, 12%-47%, 13%-47%, 14%-47%, 15%-47%, 16%-47%, 17%-47%, 18%-47%, 19%-47%, 20%-47%, 21%-47%, 22%-47%, 23%-47%, 24%-47%, 25%-47%, 26%-47%, 27%-47%, 28%-47%, 2%-46%, 3%-46%, 4%-46%, 5%-46%, 6%-46%, 7%-46%, 8%-46%, 9%-46%, 10%-46%, 11%-46%, 12%-46%, 13%-46%, 14%-46%, 15%-46%, 16%-46%, 17%-46%, 18%-46%, 19%-46%, 20%-46%, 21%-46%, 22%-46%, 23%-46%, 24%-46%, 25%-46%, 26%-46%, 27%-46%, 28%-46%, 2%-45%, 3%-45%, 4%-45%, 5%-45%, 6%-45%, 7%-45%, 8%-45%, 9%-45%, 10%-45%, 11%-45%, 12%-45%, 13%-45%, 14%-45%, 15%-45%, 16%-45%, 17%-45%, 18%-45%, 19%-45%, 20%-45%, 21%-45%, 22%-45%, 23%-45%, 24%-45%, 25%-45%, 26%-45%, 27%-45%, 28%-45%, 2%-44%, 3%-44%, 4%-44%, 5%-44%, 6%-44%, 7%-44%, 8%-44%, 9%-44%, 10%-44%, 11%-44%, 12%-44%, 13%-44%, 14%-44%, 15%-44%, 16%-44%, 17%-44%, 18%-44%, 19%-44%, 20%-44%, 21%-44%, 22%-44%, 23%-44%, 24%-44%, 25%-44%, 26%-44%, 27%-44%, 28%-44%, 2%-43%, 3%-43%, 4%-43%, 5%-43%, 6%-43%, 7%-43%, 8%-43%, 9%-43%, 10%-43%, 11%-43%, 12%-43%, 13%-43%, 14%-43%, 15%-43%, 16%-43%, 17%-43%, 18%-43%, 19%-43%, 20%-43%, 21%-43%, 22%-43%, 23%-43%, 24%-43%, 25%-43%, 26%-43%, 27%-43%, 28%-43%, 2%-42%, 3%-42%, 4%-42%, 5%-42%, 6%-42%, 7%-42%, 8%-42%, 9%-42%, 10%-42%, 11%-42%, 12%-42%, 13%-42%, 14%-42%, 15%-42%, 16%-42%, 17%-42%, 18%-42%, 19%-42%, 20%-42%, 21%-42%, 22%-42%, 23%-42%, 24%-42%, 25%-42%, 26%-42%, 27%-42%, 28%-42%, 2%-41%, 3%-41%, 4%-41%, 5%-41%, 6%-41%, 7%-41%, 8%-41%, 9%-41%, 10%-41%, 11%-41%, 12%-41%, 13%-41%, 14%-41%, 15%-41%, 16%-41%, 17%-41%, 18%-41%, 19%-41%, 20%-41%, 21%-41%, 22%-41%, 23%-41%, 24%-41%, 25%-41%, 26%-41%, 27%-41%, 28%-41%, 2%-40%, 3%-40%, 4%-40%, 5%-40%, 6%-40%, 7%-40%, 8%-40%, 9%-40%, 10%-40%, 11%-40%, 12%-40%, 13%-40%, 14%-40%, 15%-40%, 16%-40%, 17%-40%, 18%-40%, 19%-40%, 20%-40%, 21%-40%, 22%-40%, 23%-40%, 24%-40%, 25%-40%, 26%-40%, 27%-40%, 28%-40%, 2%-39%, 3%-39%, 4%-39%, 5%-39%, 6%-39%, 7%-39%, 8%-39%, 9%-39%, 10%-39%, 11%-39%, 12%-39%, 13%-39%, 14%-39%, 15%-39%, 16%-39%, 17%-39%, 18%-39%, 19%-39%, 20%-39%, 21%-39%, 22%-39%, 23%-39%, 24%-39%, 25%-39%, 26%-39%, 27%-39%, 28%-39%, 2%-38%, 3%-38%, 4%-38%, 5%-38%, 6%-38%, 7%-38%, 8%-38%, 9%-38%, 10%-38%, 11%-38%, 12%-38%, 13%-38%, 14%-38%, 15%-38%, 16%-38%, 17%-38%, 18%-38%, 19%-38%, 20%-38%, 21%-38%, 22%-38%, 23%-38%, 24%-38%, 25%-38%, 26%-38%, 27%-38%, 28%-38%, 2%-37%, 3%-37%, 4%-37%, 5%-37%, 6%-37%, 7%-37%, 8%-37%, 9%-37%, 10%-37%, 11%-37%, 12%-37%, 13%-37%, 14%-37%, 15%-37%, 16%-37%, 17%-37%, 18%-37%, 19%-37%, 20%-37%, 21%-37%, 22%-37%, 23%-37%, 24%-37%, 25%-37%, 26%-37%, 27%-37%, 28%-37%, 2%-36%, 3%-36%, 4%-36%, 5%-36%, 6%-36%, 7%-36%, 8%-36%, 9%-36%, 10%-36%, 11%-36%, 12%-36%, 13%-36%, 14%-36%, 15%-36%, 16%-36%, 17%-36%, 18%-36%, 19%-36%, 20%-36%, 21%-36%, 22%-36%, 23%-36%, 24%-36%, 25%-36%, 26%-36%, 27%-36%, 28%-36%, 2%-35%, 3%-35%, 4%-35%, 5%-35%, 6%-35%, 7%-35%, 8%-35%, 9%-35%, 10%-35%, 11%-35%, 12%-35%, 13%-35%, 14%-35%, 15%-35%, 16%-35%, 17%-35%, 18%-35%, 19%-35%, 20%-35%, 21%-35%, 22%-35%, 23%-35%, 24%-35%, 25%-35%, 26%-35%, 27%-35%, 28%-35%, 2%-34%, 3%-34%, 4%-34%, 5%-34%, 6%-34%, 7%-34%, 8%-34%, 9%-34%, 10%-34%, 11%-34%, 12%-34%, 13%-34%, 14%-34%, 15%-34%, 16%-34%, 17%-34%, 18%-34%, 19%-34%, 20%-34%, 21%-34%, 22%-34%, 23%-34%, 24%-34%, 25%-34%, 26%-34%, 27%-34%, 28%-34%, 2%-33%, 3%-33%, 4%-33%, 5%-33%, 6%-33%, 7%-33%, 8%-33%, 9%-33%, 10%-33%, 11%-33%, 12%-33%, 13%-33%, 14%-33%, 15%-33%, 16%-33%, 17%-33%, 18%-33%, 19%-33%, 20%-33%, 21%-33%, 22%-33%, 23%-33%, 24%-33%, 25%-33%, 26%-33%, 27%-33%, 28%-33%, 2%-32%, 3%-32%, 4%-32%, 5%-32%, 6%-32%, 7%-32%, 8%-32%, 9%-32%, 10%-32%, 11%-32%, 12%-32%, 13%-32%, 14%-32%, 15%-32%, 16%-32%, 17%-32%, 18%-32%, 19%-32%, 20%-32%, 21%-32%, 22%-32%, 23%-32%, 24%-32%, 25%-32%, 26%-32%, 27%-32%, 28%-32%, 2%-31%, 3%-31%, 4%-31%, 5%-31%, 6%-31%, 7%-31%, 8%-31%, 9%-31%, 10%-31%, 11%-31%, 12%-31%, 13%-31%, 14%-31%, 15%-31%, 16%-31%, 17%-31%, 18%-31%, 19%-31%, 20%-31%, 21%-31%, 22%-31%, 23%-31%, 24%-31%, 25%-31%, 26%-31%, 27%-31%, 28%-31%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%, 9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% higher than typical yeast products used for fermentation (e.g., Fali, Ethanol Red®, Thermosacc®, Angel Super Alcohol®) after 24 hours of fermentation.

In some embodiments, the compositions as described herein have a higher temperature tolerance than typical yeast products used for fermentation (e.g., Fali, Ethanol Red®, Thermosacc®, Angel Super Alcohol®). Temperature tolerance may be exhibited by the increased ethanol production, the decreased glycerol production, and/or the increased fermentation rate. In a particular embodiment, the compositions as described herein can tolerate a temperature of about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., and/or about 40° C.

In some embodiments, the compositions as described herein have a higher organic acid tolerance at low pH than typical yeast products used for fermentation (e.g., Fali, Ethanol Red®, Thermosacc®, Angel Super Alcohol®). In some embodiments, the compositions as described herein have a higher organic acid tolerance than typical yeast products used for fermentation (e.g., Fali, Ethanol Red®, Thermosacc®, Angel Super Alcohol®) at a temperature from 20° C. to 40° C., preferably from 32° C. to 36° C. In a particular embodiment, the compositions as described herein have a higher organic acid tolerance than typical yeast products used for fermentation (e.g., Fali, Ethanol Red®, Thermosacc®, Angel Super Alcohol®) at a temperature of 32° C. In another particular embodiment, the compositions as described herein have a higher organic acid tolerance than typical yeast products used for fermentation (e.g., Fali, Ethanol Red®, Thermosacc®, Angel Super Alcohol®) at a temperature of 36° C.

In some embodiments, the compositions as described herein have a higher ethanol yield than typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid. In a particular embodiment, the compositions as described herein have a higher ethanol yield than typical yeast products used for fermentation (e.g., Fali, Ethanol Red®, Thermosacc®, Angel Super Alcohol®) at a temperature of 32° C. and at a low pH with an organic acid. In another particular embodiment, the compositions as described herein have a higher ethanol yield than typical yeast products used for fermentation (e.g., Fali, Ethanol Red®, Thermosacc®, Angel Super Alcohol®) at a temperature of 36° C. and at a low pH with an organic acid.

In some embodiments, the compositions as described herein produce at least about 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid. In some embodiments, the compositions as described herein produce at most about 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, or 21.0% more ethanol after 50 hours of fermentation relative to typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid. In some embodiments, the compositions as described herein produce about 0.1%-21% (i.e. from about 0.1% to about 21%), 0.2%-21%, 0.3%-21%, 0.4%-21%, 0.5%-21%, 0.6%-21%, 0.7%-21%, 0.8%-21%, 0.9%-21%, 1%-21%, 2%-21%, 3%-21%, 4%-21%, 5%-21%, 6%-21%, 7%-21%, 8%-21%, 9%-21%, 10%-21%, 0.2%-20%, 0.3%-20%, 0.4%-20%, 0.5%-20%, 0.6%-20%, 0.7%-20%, 0.8%-20%, 0.9%-20%, 1%-20%, 2%-20%, 3%-20%, 4%-20%, 5%-20%, 6%-20%, 7%-20%, 8%-20%, 9%-20%, 10%-20%, 0.2%-19%, 0.3%-19%, 0.4%-19%, 0.5%-19%, 0.6%-19%, 0.7%-19%, 0.8%-19%, 0.9%-19%, 1%-19%, 2%-19%, 3%-19%, 4%-19%, 5%-19%, 6%-19%, 7%-19%, 8%-19%, 9%-19%, 10%-19%, 0.2%-18%, 0.3%-18%, 0.4%-18%, 0.5%-18%, 0.6%-18%, 0.7%-18%, 0.8%-18%, 0.9%-18%, 1%-18%, 2%-18%, 3%-18%, 4%-18%, 5%-18%, 6%-18%, 7%-18%, 8%-18%, 9%-18%, 10%-18%, 0.2%-17%, 0.3%-17%, 0.4%-17%, 0.5%-17%, 0.6%-17%, 0.7%-17%, 0.8%-17%, 0.9%-17%, 1%-17%, 2%-17%, 3%-17%, 4%-17%, 5%-17%, 6%-17%, 7%-17%, 8%-17%, 9%-17%, 10%-17%, 0.2%-16%, 0.3%-16%, 0.4%-16%, 0.5%-16%, 0.6%-16%, 0.7%-16%, 0.8%-16%, 0.9%-16%, 1%-16%, 2%-16%, 3%-16%, 4%-16%, 5%-16%, 6%-16%, 7%-16%, 8%-16%, 9%-16%, 10%-16%, 0.2%-15%, 0.3%-15%, 0.4%-15%, 0.5%-15%, 0.6%-15%, 0.7%-15%, 0.8%-15%, 0.9%-15%, 1%-15%, 2%-15%, 3%-15%, 4%-15%, 5%-15%, 6%-15%, 7%-15%, 8%-15%, 9%-15%, 10%-15%, 0.1%-14%, 0.2%-14%, 0.3%-14%, 0.4%-14%, 0.5%-14%, 0.6%-14%, 0.7%-14%, 0.8%-14%, 0.9%-14%, 1%-14%, 2%-14%, 3%-14%, 4%-14%, 5%-14%, 6%-14%, 7%-14%, 8%-14%, 9%-14%, 10%-14%, 0.1%-13%, 0.2%-13%, 0.3%-13%, 0.4%-13%, 0.5%-13%, 0.6%-13%, 0.7%-13%, 0.8%-13%, 0.9%-13%, 1%-13%, 2%-13%, 3%-13%, 4%-13%, 5%-13%, 6%-13%, 7%-13%, 8%-13%, 9%-13%, 10%-13%, 0.1%-12%, 0.2%-12%, 0.3%-12%, 0.4%-12%, 0.5%-12%, 0.6%-12%, 0.7%-12%, 0.8%-12%, 0.9%-12%, 1%-12%, 2%-12%, 3%-12%, 4%-12%, 5%-12%, 6%-12%, 7%-12%, 8%-12%, 9%-12%, 10%-12%, 0.1%-11%, 0.2%-11%, 0.3%-11%, 0.4%-11%, 0.5%-11%, 0.6%-11%, 0.7%-11%, 0.8%-11%, 0.9%-11%, 1%-11%, 2%-11%, 3%-11%, 4%-11%, 5%-11%, 6%-11%, 7%-11%, 8%-11%, 9%-11%, 10%-11%, 0.1%-0.2%, 0.1%-0.3%, 0.1%-0.4%, 0.1%-0.5%, 0.1%-0.6%, 0.1%-0.7%, 0.1%-0.8%, 0.1%-0.9%, 0.1%-1%, 0.1%-2%, 0.1%-3%, 0.1%-4%, 0.1%-5%, 0.1%-6%, 0.1%-7%, 0.1%-8%, or 0.1%-9% more ethanol after 50 hours of fermentation relative to typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid.

In some embodiments, the compositions as described herein have a lower glycerol yield than typical yeast products used for fermentation (e.g., Fali, Ethanol Red®, Thermosacc®, Angel Super Alcohol®) at a temperature from 20° ° C. to 40° C., preferably from 32° C. to 36° C., and at a low pH with an organic acid. In a particular embodiment, the compositions as described herein have a lower glycerol yield than typical yeast products used for fermentation (e.g., Fali, Ethanol Red®, Thermosacc®, Angel Super Alcohol®) at a temperature of 32° C. and at a low pH with an organic acid. In another particular embodiment, the compositions as described herein have a lower glycerol yield than typical yeast products used for fermentation (e.g., Fali, Ethanol Red®, Thermosacc®, Angel Super Alcohol®) at a temperature of 36° C. and at a low pH with an organic acid.

In some embodiments, the compositions as described herein produce at least about 1%, 2%, 3%, 4%, 5%, 6%, 7%, 8%, 9%, 10%, 11%, 12%, 13%, 14%, 15%, 16%, 17%, 18%, 19%, 20%, 21%, or 22% less glycerol after 50 hours of fermentation relative to typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid. In some embodiments, the compositions as described herein produce at most about 10%, 11%, 12%, 13%, 14%, 15%, 16%, 17%, 18%, 19%, 20%, 21%, 22%, 23%, 24%, 25%, 26%, 27%, 28%, 29%, or 30% less glycerol after 50 hours of fermentation relative to typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid. In some embodiments, the compositions as described herein produce about 1%-30% (i.e. from about 1% to about 30%), 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%, 9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% less glycerol after 50 hours of fermentation relative to typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid.

In some embodiments, the compositions as described herein have a higher fermentation rate than typical yeast products used for fermentation (e.g., Fali, Ethanol Red®, Thermosacc®, Angel Super Alcohol®) at a temperature from 20° C. to 40° C., preferably from 32° C. to 36° C., and at a low pH with an organic acid. In a particular embodiment, the compositions as described herein have a higher fermentation rate than typical yeast products used for fermentation (e.g., Fali, Ethanol Red®, Thermosacc®, Angel Super Alcohol®) at a temperature of 32° C. and at a low pH with an organic acid. In another particular embodiment, the compositions as described herein have a higher fermentation rate than typical yeast products used for fermentation (e.g., Fali, Ethanol Red®, Thermosacc®, Angel Super Alcohol®) at a temperature of 36° C. and at a low pH with an organic acid.

In some embodiments, the compositions as described herein have a fermentation rate at least about 1%, 2%, 3%, 4%, 5%, 6%, 7%, 8%, 9%, 10%, 11%, 12%, 13%, 14%, 15%, 16%, 17%, 18%, 19%, or 20% higher than typical yeast products used for fermentation (e.g., Fali, Ethanol Red®, Thermosacc®, Angel Super Alcohol®) after 24 hours of fermentation at a temperature from 20° C. to 40° C., preferably from 32° C. to 36° C., and at a low pH with an organic acid. In some embodiments, the compositions as described herein have a fermentation rate at most about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% higher than typical yeast products used for fermentation (e.g., Fali, Ethanol Red®, Thermosacc®, Angel Super Alcohol®) after 24 hours of fermentation at a temperature from 20° C. to 40° C., preferably from 32° C. to 36° C., and at a low pH with an organic acid. In some embodiments, the compositions as described herein have a fermentation rate about 1%-50% (i.e. from about 1% to about 50%), 2%-50%, 3%-50%, 4%-50%, 5%-50%, 6%-50%, 7%-50%, 8%-50%, 9%-50%, 10%-50%, 11%-50%, 12%-50%, 13%-50%, 14%-50%, 15%-50%, 16%-50%, 17%-50%, 18%-50%, 19%-50%, 20%-50%, 21%-50%, 22%-50%, 23%-50%, 24%-50%, 25%-50%, 26%-50%, 27%-50%, 28%-50%, 2%-49%, 3%-49%, 4%-49%, 5%-49%, 6%-49%, 7%-49%, 8%-49%, 9%-49%, 10%-49%, 11%-49%, 12%-49%, 13%-49%, 14%-49%, 15%-49%, 16%-49%, 17%-49%, 18%-49%, 19%-49%, 20%-49%, 21%-49%, 22%-49%, 23%-49%, 24%-49%, 25%-49%, 26%-49%, 27%-49%, 28%-49%, 2%-48%, 3%-48%, 4%-48%, 5%-48%, 6%-48%, 7%-48%, 8%-48%, 9%-48%, 10%-48%, 11%-48%, 12%-48%, 13%-48%, 14%-48%, 15%-48%, 16%-48%, 17%-48%, 18%-48%, 19%-48%, 20%-48%, 21%-48%, 22%-48%, 23%-48%, 24%-48%, 25%-48%, 26%-48%, 27%-48%, 28%-48%, 2%-47%, 3%-47%, 4%-47%, 5%-47%, 6%-47%, 7%-47%, 8%-47%, 9%-47%, 10%-47%, 11%-47%, 12%-47%, 13%-47%, 14%-47%, 15%-47%, 16%-47%, 17%-47%, 18%-47%, 19%-47%, 20%-47%, 21%-47%, 22%-47%, 23%-47%, 24%-47%, 25%-47%, 26%-47%, 27%-47%, 28%-47%, 2%-46%, 3%-46%, 4%-46%, 5%-46%, 6%-46%, 7%-46%, 8%-46%, 9%-46%, 10%-46%, 11%-46%, 12%-46%, 13%-46%, 14%-46%, 15%-46%, 16%-46%, 17%-46%, 18%-46%, 19%-46%, 20%-46%, 21%-46%, 22%-46%, 23%-46%, 24%-46%, 25%-46%, 26%-46%, 27%-46%, 28%-46%, 2%-45%, 3%-45%, 4%-45%, 5%-45%, 6%-45%, 7%-45%, 8%-45%, 9%-45%, 10%-45%, 11%-45%, 12%-45%, 13%-45%, 14%-45%, 15%-45%, 16%-45%, 17%-45%, 18%-45%, 19%-45%, 20%-45%, 21%-45%, 22%-45%, 23%-45%, 24%-45%, 25%-45%, 26%-45%, 27%-45%, 28%-45%, 2%-44%, 3%-44%, 4%-44%, 5%-44%, 6%-44%, 7%-44%, 8%-44%, 9%-44%, 10%-44%, 11%-44%, 12%-44%, 13%-44%, 14%-44%, 15%-44%, 16%-44%, 17%-44%, 18%-44%, 19%-44%, 20%-44%, 21%-44%, 22%-44%, 23%-44%, 24%-44%, 25%-44%, 26%-44%, 27%-44%, 28%-44%, 2%-43%, 3%-43%, 4%-43%, 5%-43%, 6%-43%, 7%-43%, 8%-43%, 9%-43%, 10%-43%, 11%-43%, 12%-43%, 13%-43%, 14%-43%, 15%-43%, 16%-43%, 17%-43%, 18%-43%, 19%-43%, 20%-43%, 21%-43%, 22%-43%, 23%-43%, 24%-43%, 25%-43%, 26%-43%, 27%-43%, 28%-43%, 2%-42%, 3%-42%, 4%-42%, 5%-42%, 6%-42%, 7%-42%, 8%-42%, 9%-42%, 10%-42%, 11%-42%, 12%-42%, 13%-42%, 14%-42%, 15%-42%, 16%-42%, 17%-42%, 18%-42%, 19%-42%, 20%-42%, 21%-42%, 22%-42%, 23%-42%, 24%-42%, 25%-42%, 26%-42%, 27%-42%, 28%-42%, 2%-41%, 3%-41%, 4%-41%, 5%-41%, 6%-41%, 7%-41%, 8%-41%, 9%-41%, 10%-41%, 11%-41%, 12%-41%, 13%-41%, 14%-41%, 15%-41%, 16%-41%, 17%-41%, 18%-41%, 19%-41%, 20%-41%, 21%-41%, 22%-41%, 23%-41%, 24%-41%, 25%-41%, 26%-41%, 27%-41%, 28%-41%, 2%-40%, 3%-40%, 4%-40%, 5%-40%, 6%-40%, 7%-40%, 8%-40%, 9%-40%, 10%-40%, 11%-40%, 12%-40%, 13%-40%, 14%-40%, 15%-40%, 16%-40%, 17%-40%, 18%-40%, 19%-40%, 20%-40%, 21%-40%, 22%-40%, 23%-40%, 24%-40%, 25%-40%, 26%-40%, 27%-40%, 28%-40%, 2%-39%, 3%-39%, 4%-39%, 5%-39%, 6%-39%, 7%-39%, 8%-39%, 9%-39%, 10%-39%, 11%-39%, 12%-39%, 13%-39%, 14%-39%, 15%-39%, 16%-39%, 17%-39%, 18%-39%, 19%-39%, 20%-39%, 21%-39%, 22%-39%, 23%-39%, 24%-39%, 25%-39%, 26%-39%, 27%-39%, 28%-39%, 2%-38%, 3%-38%, 4%-38%, 5%-38%, 6%-38%, 7%-38%, 8%-38%, 9%-38%, 10%-38%, 11%-38%, 12%-38%, 13%-38%, 14%-38%, 15%-38%, 16%-38%, 17%-38%, 18%-38%, 19%-38%, 20%-38%, 21%-38%, 22%-38%, 23%-38%, 24%-38%, 25%-38%, 26%-38%, 27%-38%, 28%-38%, 2%-37%, 3%-37%, 4%-37%, 5%-37%, 6%-37%, 7%-37%, 8%-37%, 9%-37%, 10%-37%, 11%-37%, 12%-37%, 13%-37%, 14%-37%, 15%-37%, 16%-37%, 17%-37%, 18%-37%, 19%-37%, 20%-37%, 21%-37%, 22%-37%, 23%-37%, 24%-37%, 25%-37%, 26%-37%, 27%-37%, 28%-37%, 2%-36%, 3%-36%, 4%-36%, 5%-36%, 6%-36%, 7%-36%, 8%-36%, 9%-36%, 10%-36%, 11%-36%, 12%-36%, 13%-36%, 14%-36%, 15%-36%, 16%-36%, 17%-36%, 18%-36%, 19%-36%, 20%-36%, 21%-36%, 22%-36%, 23%-36%, 24%-36%, 25%-36%, 26%-36%, 27%-36%, 28%-36%, 2%-35%, 3%-35%, 4%-35%, 5%-35%, 6%-35%, 7%-35%, 8%-35%, 9%-35%, 10%-35%, 11%-35%, 12%-35%, 13%-35%, 14%-35%, 15%-35%, 16%-35%, 17%-35%, 18%-35%, 19%-35%, 20%-35%, 21%-35%, 22%-35%, 23%-35%, 24%-35%, 25%-35%, 26%-35%, 27%-35%, 28%-35%, 2%-34%, 3%-34%, 4%-34%, 5%-34%, 6%-34%, 7%-34%, 8%-34%, 9%-34%, 10%-34%, 11%-34%, 12%-34%, 13%-34%, 14%-34%, 15%-34%, 16%-34%, 17%-34%, 18%-34%, 19%-34%, 20%-34%, 21%-34%, 22%-34%, 23%-34%, 24%-34%, 25%-34%, 26%-34%, 27%-34%, 28%-34%, 2%-33%, 3%-33%, 4%-33%, 5%-33%, 6%-33%, 7%-33%, 8%-33%, 9%-33%, 10%-33%, 11%-33%, 12%-33%, 13%-33%, 14%-33%, 15%-33%, 16%-33%, 17%-33%, 18%-33%, 19%-33%, 20%-33%, 21%-33%, 22%-33%, 23%-33%, 24%-33%, 25%-33%, 26%-33%, 27%-33%, 28%-33%, 2%-32%, 3%-32%, 4%-32%, 5%-32%, 6%-32%, 7%-32%, 8%-32%, 9%-32%, 10%-32%, 11%-32%, 12%-32%, 13%-32%, 14%-32%, 15%-32%, 16%-32%, 17%-32%, 18%-32%, 19%-32%, 20%-32%, 21%-32%, 22%-32%, 23%-32%, 24%-32%, 25%-32%, 26%-32%, 27%-32%, 28%-32%, 2%-31%, 3%-31%, 4%-31%, 5%-31%, 6%-31%, 7%-31%, 8%-31%, 9%-31%, 10%-31%, 11%-31%, 12%-31%, 13%-31%, 14%-31%, 15%-31%, 16%-31%, 17%-31%, 18%-31%, 19%-31%, 20%-31%, 21%-31%, 22%-31%, 23%-31%, 24%-31%, 25%-31%, 26%-31%, 27%-31%, 28%-31%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, 29%-30%, 1%-29%, 2%-29%, 3%-29%, 4%-29%, 5%-29%, 6%-29%, 7%-29%, 8%-29%, 9%-29%, 10%-29%, 11%-29%, 12%-29%, 13%-29%, 14%-29%, 15%-29%, 16%-29%, 17%-29%, 18%-29%, 19%-29%, 20%-29%, 21%-29%, 22%-29%, 23%-29%, 24%-29%, 25%-29%, 26%-29%, 27%-29%, 28%-29%, 1%-28%, 2%-28%, 3%-28%, 4%-28%, 5%-28%, 6%-28%, 7%-28%, 8%-28%, 9%-28%, 10%-28%, 11%-28%, 12%-28%, 13%-28%, 14%-28%, 15%-28%, 16%-28%, 17%-28%, 18%-28%, 19%-28%, 20%-28%, 21%-28%, 22%-28%, 23%-28%, 24%-28%, 25%-28%, 26%-28%, 27%-28%, 1%-27%, 2%-27%, 3%-27%, 4%-27%, 5%-27%, 6%-27%, 7%-27%, 8%-27%, 9%-27%, 10%-27%, 11%-27%, 12%-27%, 13%-27%, 14%-27%, 15%-27%, 16%-27%, 17%-27%, 18%-27%, 19%-27%, 20%-27%, 21%-27%, 22%-27%, 23%-27%, 24%-27%, 25%-27%, 26%-27%, 1%-26%, 2%-26%, 3%-26%, 4%-26%, 5%-26%, 6%-26%, 7%-26%, 8%-26%, 9%-26%, 10%-26%, 11%-26%, 12%-26%, 13%-26%, 14%-26%, 15%-26%, 16%-26%, 17%-26%, 18%-26%, 19%-26%, 20%-26%, 21%-26%, 22%-26%, 23%-26%, 24%-26%, 25%-26%, 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, 1%-24%, 2%-24%, 3%-24%, 4%-24%, 5%-24%, 6%-24%, 7%-24%, 8%-24%, 9%-24%, 10%-24%, 11%-24%, 12%-24%, 13%-24%, 14%-24%, 15%-24%, 16%-24%, 17%-24%, 18%-24%, 19%-24%, 20%-24%, 21%-24%, 22%-24%, 23%-24%, 1%-23%, 2%-23%, 3%-23%, 4%-23%, 5%-23%, 6%-23%, 7%-23%, 8%-23%, 9%-23%, 10%-23%, 11%-23%, 12%-23%, 13%-23%, 14%-23%, 15%-23%, 16%-23%, 17%-23%, 18%-23%, 19%-23%, 20%-23%, 21%-23%, 22%-23%, 1%-22%, 2%-22%, 3%-22%, 4%-22%, 5%-22%, 6%-22%, 7%-22%, 8%-22%, 9%-22%, 10%-22%, 11%-22%, 12%-22%, 13%-22%, 14%-22%, 15%-22%, 16%-22%, 17%-22%, 18%-22%, 19%-22%, 20%-22%, 21%-22%, 1%-21%, 2%-21%, 3%-21%, 4%-21%, 5%-21%, 6%-21%, 7%-21%, 8%-21%, 9%-21%, 10%-21%, 11%-21%, 12%-21%, 13%-21%, 14%-21%, 15%-21%, 16%-21%, 17%-21%, 18%-21%, 19%-21%, 20%-21%, 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-

18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, 1%-14%, 2%-14%, 3%-14%, 4%-14%, 5%-14%, 6%-14%, 7%-14%, 8%-14%, 9%-14%, 10%-14%, 11%-14%, 12%-14%, 13%-14%, 1%-13%, 2%-13%, 3%-13%, 4%-13%, 5%-13%, 6%-13%, 7%-13%, 8%-13%, 9%-13%, 10%-13%, 11%-13%, 12%-13%, 1%-12%, 2%-12%, 3%-12%, 4%-12%, 5%-12%, 6%-12%, 7%-12%, 8%-12%, 9%-12%, 10%-12%, 11%-12%, 1%-11%, 2%-11%, 3%-11%, 4%-11%, 5%-11%, 6%-11%, 7%-11%, 8%-11%, 9%-11%, 10%-11%, 1%-10%, 2%-10%, 3%-10%, 4%-10%, 5%-10%, 6%-10%, 7%-10%, 8%-10%, 9%-10%, 1%-9%, 2%-9%, 3%-9%, 4%-9%, 5%-9%, 6%-9%, 7%-9%, 8%-9%, 1%-8%, 2%-8%, 3%-8%, 4%-8%, 5%-8%, 6%-8%, 7%-8%, 1%-7%, 2%-7%, 3%-7%, 4%-7%, 5%-7%, 6%-7%, 1%-6%, 2%-6%, 3%-6%, 4%-6%, 5%-6%, 1%-5%, 2%-5%, 3%-5%, 4%-5%, 1%-4%, 2%-4%, 3%-4%, 1%-3%, 2%-3%, or 1%-2% higher than typical yeast products used for fermentation (e.g., Fali, Ethanol Red®, Thermosacc®, Angel Super Alcohol®) after 24 hours of fermentation at a temperature from 20° C. to 40° C., preferably from 32° C. to 36° C., and at a low pH with an organic acid.

In some embodiments, the compositions as described herein have one or more of the defining characteristics described herein. In some embodiments, the compositions as described herein have one or more of the defining characteristics described herein at a temperature from 20° C. to 40° C., preferably from 32° C. to 36° C., and at a low pH with an organic acid. In some embodiments, the compositions as described herein have one or more of the defining characteristics described herein at a temperature from 20° C. to 40° C., preferably from 32° C. to 36° C., and at a normal pH without an organic acid. For example, in some embodiments, the compositions as described herein have a higher ethanol yield, a lower glycerol yield, a higher fermentation rate, a higher temperature tolerance, and a higher organic acid tolerance than typical yeast products used for fermentation (e.g., Fali, Ethanol Red®, Thermosacc®, Angel Super Alcohol®); in some embodiments, the compositions as described herein have a higher fermentation rate, produce lower levels of glycerol, and have a higher ethanol yield than typical yeast products used for fermentation (e.g., Fali, Ethanol Red®, Thermosacc®, Angel Super Alcohol®); in some embodiments, the compositions as described herein have a higher fermentation rate and produce lower levels of glycerol than typical yeast products used for fermentation (e.g., Fali, Ethanol Red®, Thermosacc®, Angel Super Alcohol®).

4. ETHANOL PRODUCTION

Described herein are processes for producing ethanol from a substrate by contacting the substrate with a fermenting organism or a composition comprising a fermenting organism. The fermenting organism is selected from the yeast strains described herein and the derivatives thereof. *Saccharomyces cerevisiae* Y1912, Y1913, Y1914, Y1919, Y1923, Y1927, Y1929, or a fermenting organism having properties that are about the same as those of the yeast strains described herein or a derivative of the yeast strains described herein having the defining characteristics may be used in a process described herein. Also described herein is a fermented product comprising any of the yeasts described herein. Further described herein is a fermented product obtained by the methods described herein. The fermented product can include, but is not limited to, fuel ethanol, industrial ethanol, potable ethanol, bioethanol, fermented foods such as alcoholic beverages, cultured milk and yogurt, wine, beer, cider, tempeh, miso, kimchi, sauerkraut, and fermented sausage.

Fermentation is carried out in a fermentation medium. The fermentation medium includes a fermentation substrate, that is, the carbohydrate source that is metabolized by the fermenting organism, such as a biomass. The fermentation medium may comprise nutrients for the fermenting organism(s). Nutrients are widely used in the art of fermentation and include nitrogen sources, vitamins, minerals, or combinations thereof.

In one embodiment, the strain or derivative, or composition as described herein is incubated with a substrate comprising fermentable sugars from a biomass such as a plant biomass from forests and/or from agricultural or food-processing products and/or coproducts that constitute a considerable source of carbon for the production of molecules of interest. The strain or derivative is incubated with the substrate under conditions that allow fermentation of the fermentable sugars. The fermentable sugars may be glucose, galactose, maltose, fructose, sucrose, mannose, or a combination thereof. Typically, the fermentable sugars are glucose and sucrose. The source of the fermentable sugar in the substrate may be any source which contains fermentable sugar. The fermentable sugar in the substrate may be, for example, from any one or more of the following sources: hydrolyzed starch, hydrolyzed cellulose, molasses (from sugar cane or sugar beet), sugar cane juice, agave, sugar beet juice, grape juice, fruit juice, glucose, hydrolyzed maltodextrins, raw sugar juice, galactose, sucrose, any other forms of fermentable sugars, or combinations thereof. Starch may be obtained from any starch rich crops. Examples of starch rich crops include, but are not limited to, corn, wheat, barley, cassava, sorghum, sweet potato, millet, rice, or any other starch rich crops. In preparing the substrate, the crop is typically crushed and mixed with water and hydrolytic enzyme(s) under conditions which result in hydrolysis of the starch and release of fermentable sugars such as glucose. Typical enzymes for hydrolysis of the starch include α-amylase, amyloglucosidase, pullulanase, β-amylase, glucoamylase, or mixtures thereof.

Generally, fermenting organisms such as yeast, including *Saccharomyces cerevisiae* yeast, require an adequate source of nitrogen for propagation and fermentation. Many sources of nitrogen can be used and such sources of nitrogen are well known in the art. The nitrogen source may be organic, such as urea or corn mash, or inorganic, such as ammonia or ammonium hydroxide or ammonium salts.

In a particular embodiment, the biomass may comprise or originate from sugar cane, sugar beet, sweet sorghum, agave, corn, wheat, rice, barley, rye, sorghum, triticale, potato, sweet potato, cassava, or a combination thereof. In a particular embodiment, the substrate is provided in the form of corn mash or a Synthetic Corn Medium (SCM). Methods for preparation of corn mash are known in the art and are described in, for example, Thomas et al., (2001) *Journal of Applied Microbiology,* 90, 819-828. Methods for preparation of substrates similar in function to SCM are known in the art and are described in, for example, U.S. Pat. No. 10,106,823, which is incorporated herein by reference in its entirety.

Methods for the preparation of starch-based substrates are also described in, for example, PCT Publication No. 2006/113683 or U.S. Patent Publication No. 2007/0014905.

The sugar content of the fermentation medium may be adjusted so that it is as high as possible while at the same time ensuring that the sugar is converted to ethanol as rapidly and as completely as possible. It is preferred that the yeast convert all of the sugars of the medium to ethanol, and that the overall yield of conversion of the consumed sugars to ethanol is as high as possible and, consequently, the fewest coproducts such as glycerol are generated during the fermentation.

The fermentation is carried out at a temperature which permits fermentation of the fermentable sugars. In general, the higher the temperature at which the fermentation can be carried out, the more economic the industrial process. Typically, the temperature at which the fermentation is carried out is from 25-42° C. (i.e. from 25° C. to 42° C.). Suitable temperature ranges include 25-41° C., 26-40° C., 27-40° C., 28-40° C., 29-40° C., 30-40° C., 25-39° C., 26-39° ° C., 27-39° C., 28-39° C., 29-39° C., 30-39° C., 31-39° ° C., 32-39° C., 33-39° C., 25-38° C., 26-38° C., 27-38° C., 28-38° C., 29-38° C., 30-38° C., 31-38° C., 32-38° C., 33-38° C., 25-27° C., 26-37° C., 27-37° C., 28-37° C., 29-37° C., 30-37° C., 31-37° C., 32-37° C., 33-37° C., 25-36° ° C., 26-36° C., 27-36° C., 28-36° C., 29-36° C., 30-36° C., 31-36° C., 32-36° C., 33-36° C., 25-35° C., 26-35° C., 27-35° C., 28-35° C., 29-35° C., 30-35° C., 31-35° C., 32-35° C., or 33-35° C.

Methods for fermentation and distillation are known in the art and are described in, for example, WO 2006/113683 or US 2007/0014905. In particular, ethanol production as described herein may be carried out using simultaneous saccharification and fermentation ("SSF"), batch fermentation, or continuous fermentation.

a. Simultaneous Saccharification and Fermentation ("SSF")

SSF is widely used in industrial scale fermentation product production processes, especially ethanol production processes. When doing SSF the saccharification step and the fermentation step are carried out simultaneously. There is no holding stage for the saccharification, meaning that a fermenting organism, such as yeast, and enzyme(s), may be added together. However, it is also contemplated to add the fermenting organism and enzyme(s) separately (i.e. separate hydrolysis and fermentation (SHF)). SSF may be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours, and preferably around 50 hours. In an embodiment the pH is from about 3.0-6.0, preferably from about 4.0-5.0.

Subsequent to fermentation, e.g., SSF, the ethanol may be separated from the spent fermentation medium or beer. The beer may be rectified or distilled to recover/extract the desired fermentation products (i.e. ethanol and higher alcohols). Alternatively, the desired fermentation product (i.e. ethanol) may be extracted from the fermentation medium by micro or membrane filtration techniques known in the art. The fermentation product (i.e. ethanol) may also be recovered by stripping or other method well known in the art.

In some embodiments, the ethanol is not recovered/extracted from the fermentation medium or beer, such as for the production of alcoholic beverages.

b. Batch Fermentation

Batch fermentation is where fermentation is done in separate batches. A batch fermentation is a process where the fermentation medium is provided in the fermenter from the start, where the fermenter is inoculated with an intended microorganism (i.e. yeast, yeast product) and the fermentation process is running until a predetermined condition has been reached, typically depletion of the substrate in the fermentation medium and the cessation of ethanol production caused by the depletion. Once the process is complete, the products are removed from the fermenter and the fermenter is sterilized before the next fermentation takes place. Then the contents are an end product (e.g., wine) or can be rectified/distilled (e.g., fuel ethanol and whisky).

A fed-batch process may also be used. A fed-batch process is a fermentation where a part of the fermentation medium is provided from the start of the fermentation process where the inoculum is added, and at a certain time point after the start of the fermentation additional substrate, feed is fed to the fermenter at a rate that may be predetermined or determined by the conditions in the fermenter; until the maximal volume has been reached. The feed may or may not have the same composition as the initial fermentation medium. Then the contents are an end product (e.g., wine) or can be rectified/distilled (e.g., fuel ethanol and whisky).

c. Continuous Fermentation

Continuous fermentation allows for fermentation to be done over long periods of time without fermenting in separate batches. A continuous fermentation process is a process where new growth medium is continuously fed to the fermenter and ferment is simultaneously removed from the fermenter at the same rate so the volume in the fermenter is constant. Then the contents are an end product (e.g., wine) or can be rectified/distilled (e.g., fuel ethanol and whisky).

5. ETHANOL

The ethanol produced by the yeast and the derivatives thereof as described herein may be fuel ethanol, industrial ethanol, and/or potable ethanol. Fuel ethanol, industrial ethanol, and potable alcohol can be produced from starch-containing biomass, including starch found in cereal grains (e.g., corn, wheat, rice, sorghum/milo, barley, etc.) and from starch in tubers and root vegetables (e.g., potato, cassava, etc.); and from vegetative portions of plants containing the sugars sucrose, glucose, and fructose (e.g., sugar cane, sweet sorghum, sugar beets, agave, etc.); and from the fruits and berries of plants containing sucrose, glucose, and fructose (e.g., grapes, oranges, peaches, cherries, etc.).

Fuel ethanol and industrial ethanol can also be produced from plant biomass containing cellulose and hemicellulose, such as cereal grain crop residues (e.g., wheat and rice straw, corn stover, corn cobs, etc.), from corn fiber, from so-called energy crops such as switchgrass and poplar, from woody material waste including residues from saw mills (e.g., saw dust and wood chips), from residues from pulp and paper manufacture, and from waste paper and cardboard.

a. Fuel Ethanol

Fuel ethanol is manufactured for use in internal combustion engines and may manufactured as anhydrous or hydrous fuel ethanol. Anhydrous fuel ethanol can be mixed with gasoline to form an ethanol/gasoline mixture or with diesel to form an ethanol/diesel mixture. Hydrous fuel ethanol can be used directly as a fuel in internal combustion engines.

b. Industrial Ethanol

Industrial ethanol is manufactured for use in a variety of applications including as a solvent in pharmaceuticals, cosmetics, detergents, household cleaners and disinfectants, and coatings and inks; and as a chemical intermediate in manufacture of ethyl acetate, ethyl acrylate, polyethylene, acetic acid, and other organic molecules of industrial importance.

c. Potable Ethanol

Potable ethanol is manufactured for human consumption and includes the ethanol found in wine, beer, cider, sake, mead, kombucha, and distilled spirits including whisky, bourbon, cachaça, Chinese white liquor, baijiu, and others.

6. YEAST STRAIN PRODUCTION a. Directed Mating

Figures 1C, 1D:
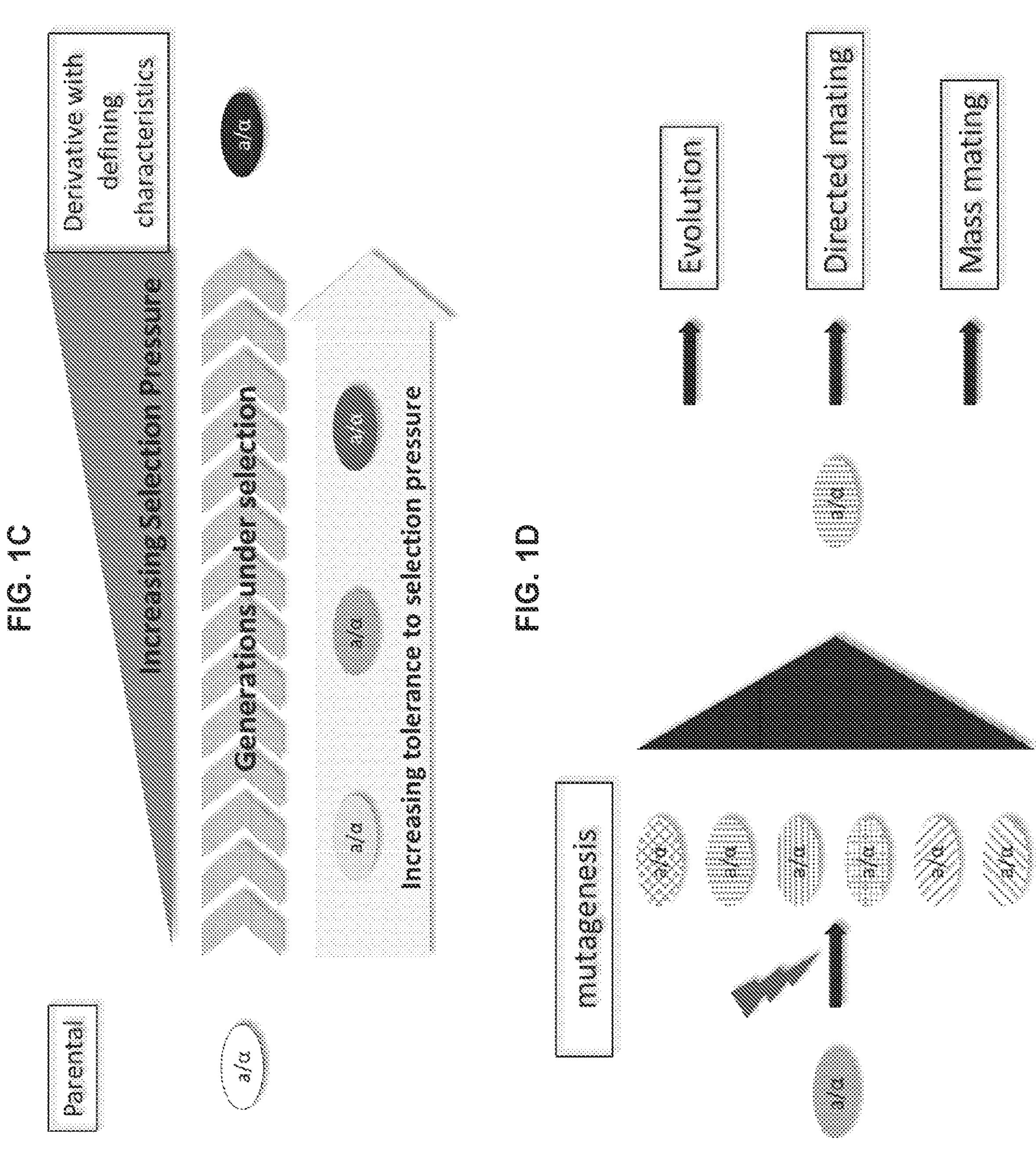
FIG. 1C shows directed evolution of yeast strains.
FIG. 1D shows mutagenesis of yeast strains.

Provided herein are methods of producing the derivative of a *Saccharomyces* yeast strain as described herein. The methods may include providing a first yeast strain that is selected from *Saccharomyces* strains Y1912, Y1913, Y1914, Y1919, Y1923, Y1927, and Y1929 and a second yeast strain that is any yeast strain, such as a yeast strain in the *Saccharomyces* sensu stricto clade, such as a *Saccharomyces cerevisiae* strain. The second strain may also be any of the yeast strains described herein. The methods may further include inducing sporulation of the first yeast strain and the second yeast strain. The methods may also include screening and selecting spores from the first yeast strain and spores from the second yeast strain. In addition, the method may include hybridizing a selected spore of the first yeast strain with a selected spore of the second yeast strain, and screening or selecting for a derivative strain. The method may include screening or selecting for spores which exhibit one or more defining characteristics of the *Saccharomyces* strains as described herein. The method may further include screening or selecting a hybrid which exhibits one or more defining characteristics of the *Saccharomyces* strains as described herein. An example of directed mating is provided in FIG. 1A. Therefore, the parents (i.e. donors of the "a" and "alpha" haploids) that generate a hybrid are known. In an embodiment, the yeast strains and derivatives thereof as described herein are made from a process as shown in FIG. 1. In an embodiment, the *Saccharomyces* yeast strains designated Y1912, Y1913, Y1914, Y1919, Y1923, Y1927, and Y1929 are derived from one or more different *Saccharomyces* yeast strains by a process shown in FIG. 1, for example by the process shown in FIG. 1A, so that one or more of Y1912, Y1913, Y1914, Y1919, Y1923, Y1927, or Y1929 is a product of directed mating. Methods of directed mating are known in the art and are described in U.S. Pat. Nos. 10,308,963 and 10,106,823, which are incorporated herein by reference.

b. Mass Mating

Provided herein are methods of producing the derivative of a *Saccharomyces* yeast strain as described herein. The methods may include providing a first yeast strain that is selected from *Saccharomyces* strains Y1912, Y1913, Y1914, Y1919, Y1923, Y1927, and Y1929 and one or more additional yeast strains that are any yeast strain, such as a yeast strain in the *Saccharomyces* sensu stricto clade, such as a *Saccharomyces cerevisiae* strain. The one or more additional yeast strains may also be any of the yeast strains described herein. The methods may further include inducing sporulation of the first yeast strain and the one or more additional yeast strains. The methods may also include mixing all of the spores to allow for hybridization of the spores and screening or selecting for a derivative strain. The method may include screening or selecting a hybrid which exhibits one or more defining characteristics of the *Saccharomyces* strains as described herein. An example of mass mating is provided in FIG. 1B. Therefore, the parents (i.e. donors of the "a" and "alpha" haploids) that generate a hybrid are unknown. In an embodiment, the yeast strains and derivatives thereof as described herein are derived from a process as shown in FIG. 1. In an embodiment, the *Saccharomyces* yeast strains designated Y1912, Y1913, Y1914, Y1919, Y1923, Y1927, and Y1929 are derived from one or more different *Saccharomyces* yeast strains by a process shown in FIG. 1, for example by the process shown in FIG. 1B, so that one or more of Y1912, Y1913, Y1914, Y1919, Y1923, Y1927, or Y1929 is a product of mass mating.

7. EXAMPLES

The foregoing may be better understood by reference to the following examples, which are presented for purposes of illustration and are not intended to limit the scope of the invention. The present disclosure has multiple aspects and embodiments, illustrated by the appended non-limiting examples.

Example 1

Materials and Methods

A Synthetic Corn Medium (SCM) was used in the following Examples. SCM simulates corn mashes that are generally used in industrial bioethanol production. SCM is designed to reflect the chemical composition of Yellow Dent Corn #2 in terms of sugar and nutrient availability. SCM reflects a high gravity model corn system at 32% solids with approximately 72% starch, which should yield 13-14% w/v final ethanol. The synthetic nature of the medium allows for strict replication of the test conditions for every experiment.

This medium is used to monitor the performance of the yeast during a Simultaneous Saccharification and Fermentation (SSF) process, in which the starch in the medium is broken down to glucose through the use of the enzyme glucoamylase (Saccharification) and the glucose is used by the yeast to produce ethanol (Fermentation) at the same time (Simultaneous).

Preparation of SCM. 1 L of SCM complete medium was made by adding 500 g water to a 2 L beaker. The amounts of the ingredients in TABLE 1 were added to the beaker, using less than 100 ml water in total. The solution was stirred at 300 rpm and heated gradually to 75° C. Once the solution was 75° C., it was removed from the heat and allowed to cool to ambient temperature while mixing. During mixing, 100.0 mL 10×SCM vitamin mix (TABLE 2) and 10.0 mL 100×SCM mineral mix (TABLE 3) were added to the solution. Then, 25.0 mL SCM amino acid slurry (TABLE 4), 1.2 g urea (550 ppm nitrogen equivalent), 0.400 mL virginiamycin stock solution (1.0 ppm), and 0.1 g penicillin G powder (100 ppm) were added to the solution while stirring. The solution was transferred to a 1 L volumetric flask and made to 1 L with water. The pH of the solution was adjusted to 5.0-5.2 with 28% sulfuric acid or 28% ammonium/potassium hydroxide. The solution was mixed by inversion and further stirring at 300-450 rpm. A representative sample of the solution was collected for measurement of specific gravity and for HPLC analysis.

TABLE 1

Ingredients for 1 L SCM complete medium.

| Ingredient | Specifications | g per L of SCM |
| --- | --- | --- |
| Maltodextrin M100 | 100.0% purity, 6% moisture | 295.10 |
| Potassium phosphate dibasic | 98.0% purity, 1.0% moisture | 1.16 |

TABLE 1-continued

Ingredients for 1 L SCM complete medium.

| Ingredient | Specifications | g per L of SCM |
|---|---|---|
| Potassium phosphate monobasic | 99.0% purity, 0.2% moisture | 10.22 |
| Magnesium sulfate heptahydrate | 99.0% purity, 51.1% moisture | 5.54 |
| Sodium chloride | 99.0% purity | 0.30 |
| Calcium chloride dihydrate | 99.0% purity, 24.5% moisture | 0.43 |

TABLE 2

Ingredients for 1 L 10× SCM vitamin mix.

| Ingredient | Specifications | mg per L of SCM vitamin mix |
|---|---|---|
| Riboflavin | 98.0% purity | 5.5 |
| Pyridoxine HCl | 98.0% purity | 25.4 |
| Folic acid | 97.0% purity, 9.0% moisture | 1.3 |
| Calcium pantothenate | 98.0% purity, 5.0% moisture | 59.6 |
| Thiamine HCl | 99.0% purity, 7.0% moisture | 20.3 |
| Nicotinic acid | 98.0% purity | 110.5 |
| Myo-inositol | 99.0% purity | 7956.4 |
| 4-aminobenzoic acid | 99.0% purity | 2.2 |

TABLE 3

Ingredients for 100 mL 100× SCM mineral mix.

| Ingredient | Specifications | mg per 100 mL of SCM mineral mix |
|---|---|---|
| Iron (III) chloride hexahydrate | 97.0% purity, 40% moisture | 578.7 |
| Zinc sulfate heptahydrate | 99.0% purity, 43.8% moisture | 240.5 |
| Manganese (II) sulfate monohydrate | 99.0% purity, 10.7% moisture | 60.1 |
| Copper (II) sulfate pentahydrate | 99.0% purity, 36% moisture | 62.0 |

TABLE 4

Ingredients for 200 mL SCM amino acid slurry.

| Ingredient | Specifications | mg per 200 mL of SCM amino acid slurry |
|---|---|---|
| L-Alanine | 99.5% purity, 0.1% moisture | 761.0 |
| L-Arginine | 99.5% purity, 0.1% moisture | 116.9 |
| L-Aspartic acid | 99.5% purity, 0.1% moisture | 663.3 |
| L-Cystine | 98.5% purity, 0.1% moisture | 122.1 |
| L-Glutamic acid | 99.5% purity, 0.1% moisture | 1725.9 |
| L-Glycine | 99.0% purity, 0.1% moisture | 409.6 |
| L-Histidine | 99.5% purity, 0.5% moisture | 94.5 |
| L-Isoleucine | 99.5% purity, 0.1% moisture | 380.0 |
| L-Leucine | 99.5% purity, 0.1% moisture | 1336.3 |
| L-Lysine (monohydrochloride) | 99.5% purity, 0.5% moisture | 170.4 |
| L-Methionine | 99.5% purity, 0.1% moisture | 185.6 |
| L-Phenylalanine | 98.0% purity | 526.7 |
| L-Proline | 99.5% purity, 0.1% moisture | 819.4 |
| L-Serine | 99.5% purity, 0.1% moisture | 556.0 |
| L-Threonine | 99.5% purity, 0.1% moisture | 390.1 |
| L-Tryptophan | 99.5% purity, 0.1% moisture | 44.2 |
| L-Tyrosine | 99.0% purity, 0.2% moisture | 330.9 |
| L-Valine | 99.5% purity, 0.1% moisture | 487.9 |

100.00±0.10 mL of SCM was added to each test sample vessel for each yeast strain. At least three replicates per test sample were tested. All test sample vessels with the SCM were incubated at 32° C. at 150 rpm for 1 to 2 hours to equilibrate to temperature. The specific gravity of each sample vessel was measured with a density meter. A sample from the sample vessels were taken for HPLC analysis. The sample vessel was swirled to ensure that all cells were in suspension and 1.9 mL of the sample vessel media was placed into a 2 mL microcentrifuge tube. The samples were centrifuged at 3,000 rpm for 10 minutes. The supernatant was decanted into a syringe with a pre-fitted 0.2 μm filter and the filtrate was collected into a glass HPLC vial. The HPLC vials with samples may be stored at +4° C. for up to 1 month before HPLC analysis or analyzed immediately.

Isolation of the *Saccharomyces cerevisiae* strains. The yeast strains were isolated from an agar plate, methods of isolation are known in the art.

Yeast culture. 2.5 mL of the yeast culture (i.e. yeast in common yeast growth medium; e.g., glucose-yeast-peptone medium (GYP)) was inoculated into the sample vessels with SCM to reach a final cell concentration of $1.0\times10^6$ cells/mL.

Yeast slant or colony on a plate. A full 10 μL loop of cells were inoculated in 50 mL of sterile 2% GYP. The culture was incubated overnight at 32° C. or 36° C. and 150 rpm to give a cell concentration of $1\times10^8$ cells/mL. 2.5 mL of the culture was inoculated into the sample vessels with SCM to reach a final cell concentration of $2.5\times10^6$ cells/mL. Immediately after all yeast samples were added, 10× diluted glucoamylase was added to the sample vessels. In the case of Spirizyme Fuel HS 140 μL was added, while for Spirizyme Ultra, 224 μL was added. If an alternative glucoamylase is used, the enzyme dose must be adjusted as appropriate for 100 mL on a 32% dry corn solids basis. Typically, the dose is expressed in % w/w units so the SCM solution density will need to be taken into consideration.

The sample vessels were closed with an airlock cap. The pressurized airlock was filled with 9 mL sterile water. The best way to do this is to place the tip of the pipette into the airlock opening and dispense as close to the bubble as possible. The sample vessels were incubated at 32° C. or 36° C., 150 rpm and 80% humidity for 50 hours. The weights of the sample vessels were measured before incubation and at the following timepoints after the start of incubation: 18, 24, 44 and 50 hours. After 50 hours of incubation, the sample vessels were removed from the incubator and sampled using HPLC analysis as described above. The specific gravity of the sample vessels was measured with a density meter. Then, pH of the remaining sample in the sample vessel was measured. Following the pH measurement, yeast cell concentration and viability were measured using methylene blue on a hemocytometer.

Statistical analysis. An analysis of variance (ANOVA) was performed for the final mass loss, ethanol, glycerol and glucose values, and the 95% confidence intervals (95% Cl) for each analyte was calculated. The use of a program such as SAS JMP is preferred.

Example 2

Strain Description

The *Saccharomyces* yeast strains as described herein, and representative samples of the strains having been deposited under NRRL Patent Deposit Designation No. Y-68003 (Y1912), NRRL Patent Deposit Designation No. Y-68004 (Y1913), NRRL Patent Deposit Designation No. Y-68005 (Y1914), NRRL Patent Deposit Designation No. Y-68006 (Y1919), NRRL Patent Deposit Designation No. Y-68007 (Y1923), NRRL Patent Deposit Designation No. Y-68008

(Y1927), and NRRL Patent Deposit Designation No. Y-68009 (Y1929) were observed to possess the following characteristics, based on 4 replicates conducted at 32° C. or 36° C., at a normal pH without organic acids or at a low pH with organic acids. Y1609 is shown for comparison and was analyzed under similar conditions.

Notable and advantageous features of the yeast strains as described herein comprise increased metabolic ethanol increase, decreased metabolic glycerol, and increased initial fermentation rate as compared to a control. The advantageous fermentation characteristics of the yeast strains as described herein are provided in the following examples.

Example 3

Ethanol Production, Glycerol Production, and Fermentation Rate

Figure 2A:
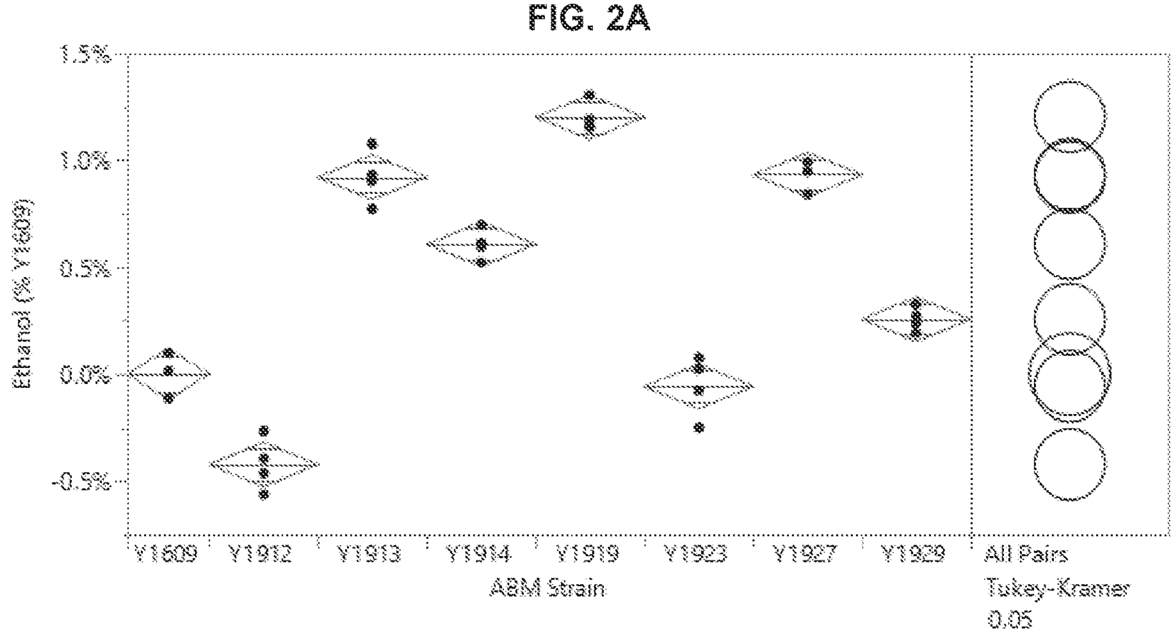
FIG. 2 shows the percent differences relative to a control (Y1609) under a normal fermentation temperature (32° C.) in a proprietary synthetic corn starch medium (SCM) at pH 5.2 without exogenous addition of organic acids at the end of a 50-hour fermentation. Percent differences relative to control in ethanol at end of fermentation (FIG. 2A), glycerol at end of fermentation (FIG. 2B), and initial fermentation rate of fermentation (FIG. 2C) are shown.
Figure 2B:
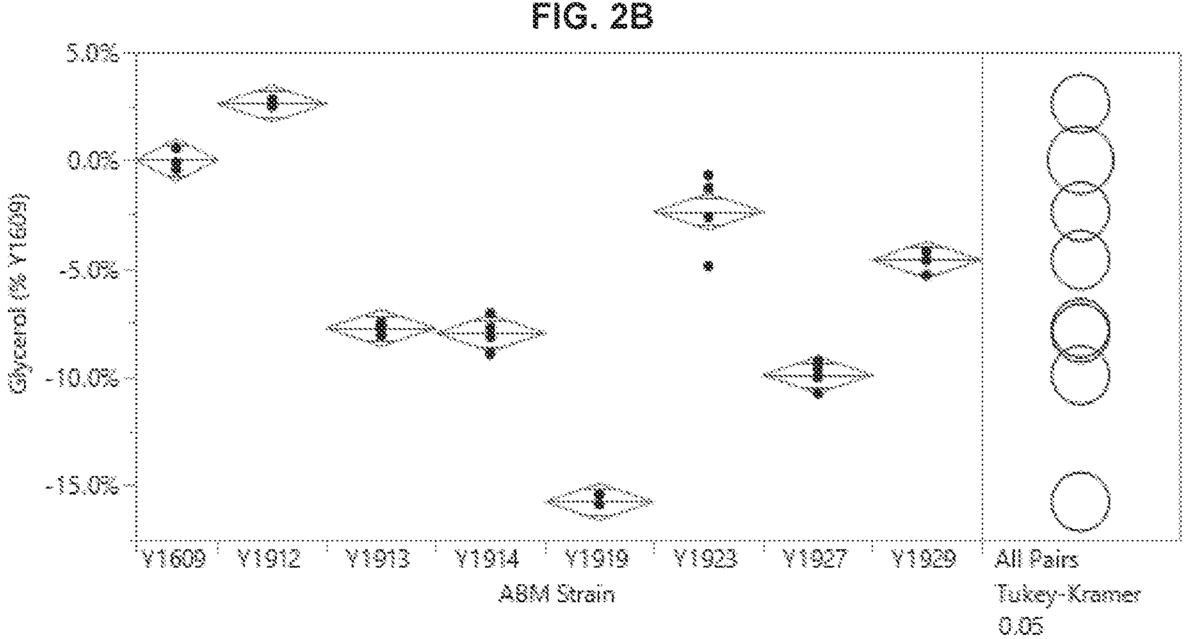
Figure 2C:
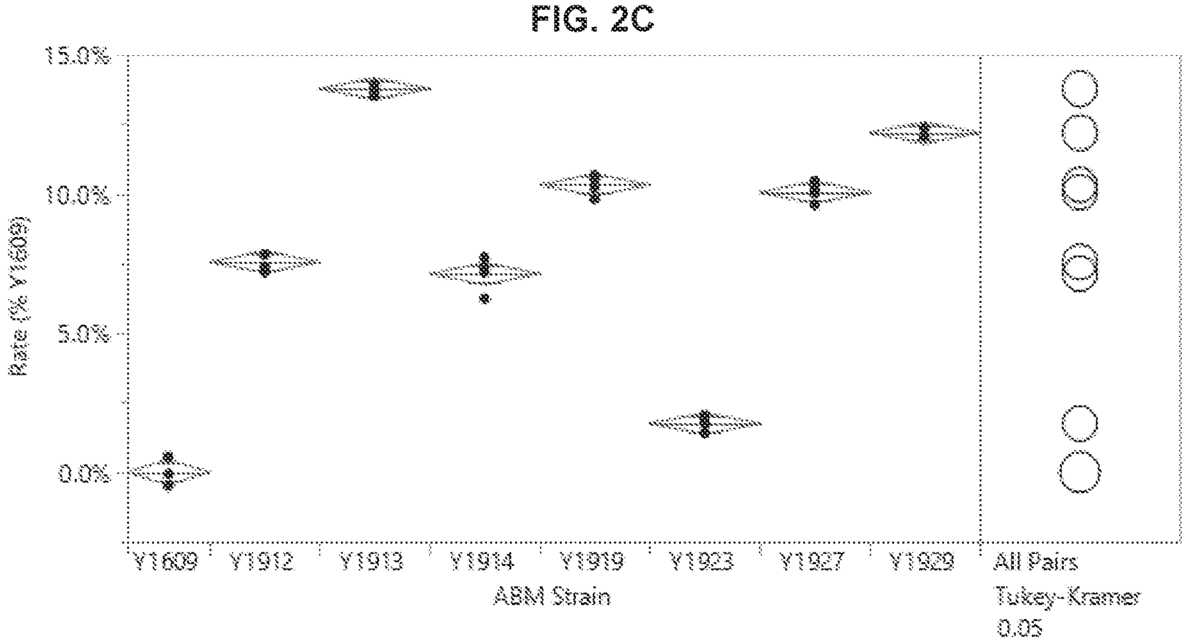

The yeast strains as described herein, were evaluated for ethanol production, glycerol production, and fermentation rate at 32° C. and pH 5.2 in synthetic corn starch medium (SCM) (TABLE 5 and FIG. 2). The control (Y1609) is shown for comparison.

TABLE 5

Defining characteristics relative to control under fermentation temperature of 32° C. and pH 5.2.

| | Ethanol (% w/v) | | Ethanol (% Y1609) | | Glycerol (% w/v) | | Glycerol (% Y1609) | | Acetic acid (% w/v) | | Lactic acid (% w/v) | | Rate (% Y1609) | |
|---|---|---|---|---|---|---|---|---|---|---|---|---|---|---|
| strain | Mean | Std Dev | Mean | Std Dev | Mean | Std Dev | Mean | Std Dev | Mean | Std Dev | Mean | Std Dev | Mean | Std Dev |
| Y1609 | 13.2 | 0.01 | 0% | 0.10% | 1.19 | 0.01 | 0.00% | 0.50% | 0.13 | 0 | 0.08 | 0 | 0% | 0.50% |
| Y1912 | 13.1 | 0.02 | 0% | 0.10% | 1.22 | 0 | 2.60% | 0.10% | 0.1 | 0 | 0.08 | 0 | 7.60% | 0.30% |
| Y1913 | 13.3 | 0.02 | 0.90% | 0.10% | 1.1 | 0 | −8% | 0.20% | 0.13 | 0 | 0.08 | 0 | 14% | 0.20% |
| Y1914 | 13.3 | 0.01 | 0.60% | 0.10% | 1.1 | 0.01 | −8% | 0.80% | 0.1 | 0.02 | 0.08 | 0 | 7% | 0.60% |
| Y1919 | 13.3 | 0.01 | 1.20% | 0.10% | 1.01 | 0 | −16% | 0.20% | 0.12 | 0.01 | 0.08 | 0 | 10% | 0.40% |
| Y1923 | 13.2 | 0.02 | 0.00% | 0.10% | 1.17 | 0.02 | −2% | 1.90% | 0.11 | 0.01 | 0.09 | 0 | 2% | 0.30% |
| Y1927 | 13.3 | 0.01 | 0.90% | 0.10% | 1.08 | 0.01 | −10% | 0.70% | 0.12 | 0.01 | 0.08 | 0 | 10% | 0.30% |
| Y1929 | 13.2 | 0.01 | 0.30% | 0.10% | 1.14 | 0.01 | −5% | 0.50% | 0.12 | 0.01 | 0.08 | 0 | 12% | 0.20% |

Figure 3A:
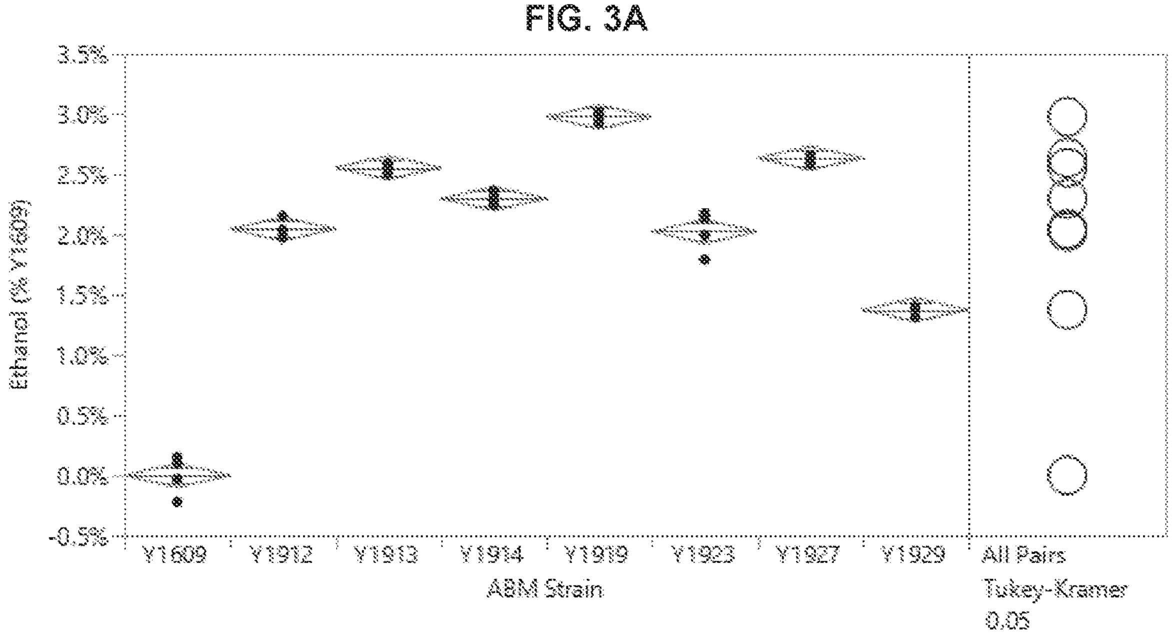
FIG. 3 shows the percent differences relative to a control under a normal fermentation temperature (32° C.) in a proprietary synthetic corn starch medium (SCM) at pH 4.0 with exogenous addition of 1% w/v lactic acid and 0.05% w/v acetic acid at the end of a 50-hour fermentation. Percent differences relative to control in ethanol at end of fermentation (FIG. 3A), glycerol at end of fermentation (FIG. 3B), and initial fermentation rate of fermentation (FIG. 3C) are shown.
Figure 3B:
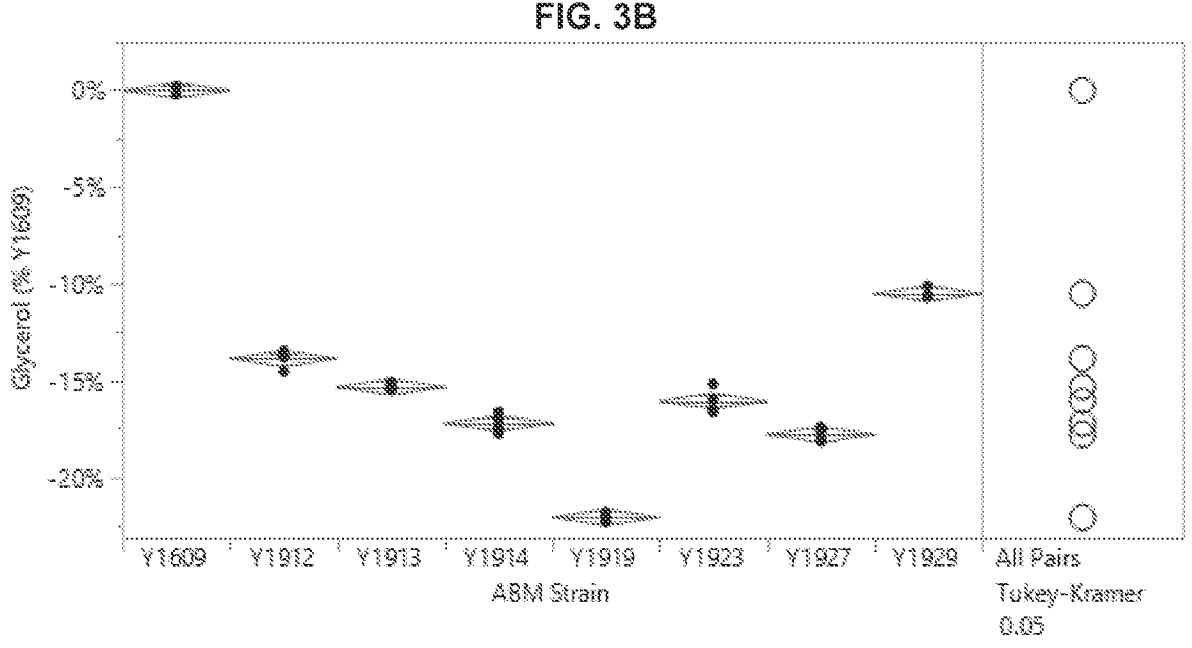
Figure 3C:
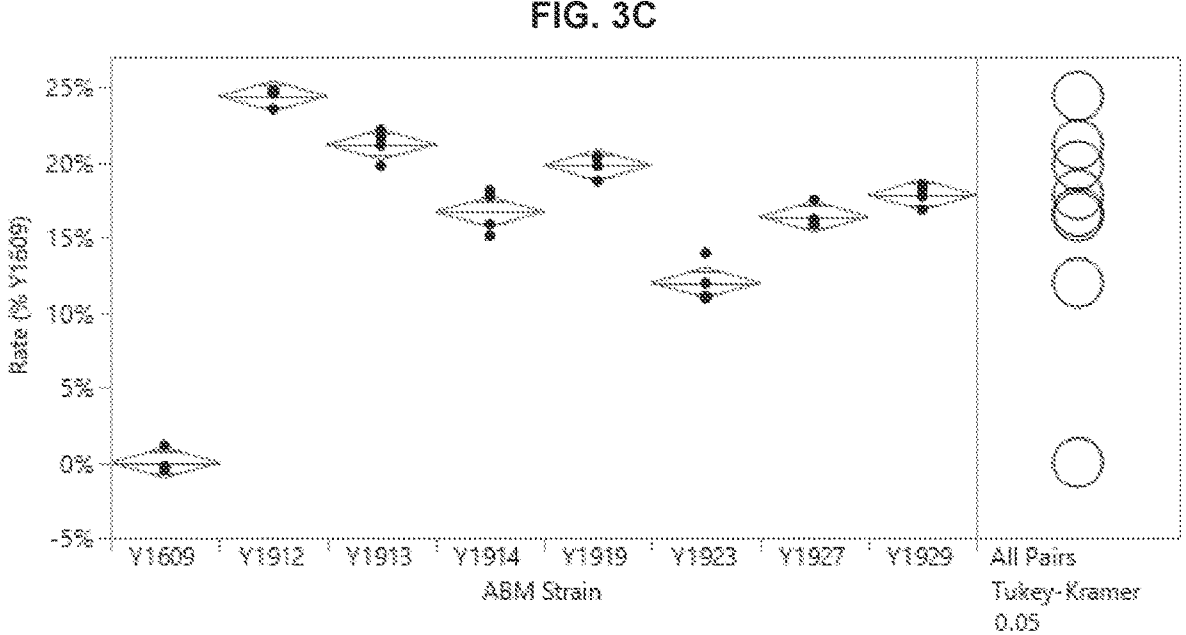

The parent yeast strains as described herein were evaluated for ethanol production, glycerol production, and fermentation rate at 32° C. and pH 4.0 in SCM with exogenous addition of 1% w/v lactic acid and 0.05% w/v acetic acid (TABLE 6 and FIG. 3). The control (Y1609) is shown for comparison.

TABLE 6

Defining characteristics relative to control under fermentation temperature of 32° C. and pH 4.0 with addition of organic acids.

| | Ethanol (% w/v) | | Ethanol (% Y1609) | | Glycerol (% w/v) | | Glycerol (% Y1609) | | Acetic acid (% w/v) | | Lactic acid (% w/v) | | Rate (% Y1609) | |
|---|---|---|---|---|---|---|---|---|---|---|---|---|---|---|
| strain | Mean | Std Dev | Mean | Std Dev | Mean | Std Dev | Mean | Std Dev | Mean | Std Dev | Mean | Std Dev | Mean | Std Dev |
| Y1609 | 13.2 | 0.02 | 0.00% | 0.20% | 1.23 | 0 | 0.00% | 0.20% | 0.13 | 0 | 1.08 | 0 | 0% | 0.80% |
| Y1912 | 13.5 | 0.01 | 2.00% | 0.10% | 1.06 | 0.01 | −14% | 0.50% | 0.12 | 0 | 1.09 | 0 | 24% | 0.60% |
| Y1913 | 13.6 | 0.01 | 2.60% | 0.00% | 1.04 | 0 | −15% | 0.20% | 0.12 | 0.01 | 1.08 | 0 | 21% | 1.00% |
| Y1914 | 13.5 | 0.01 | 2.30% | 0.10% | 1.02 | 0.01 | −17% | 0.50% | 0.11 | 0 | 1.09 | 0 | 17% | 1.50% |
| Y1919 | 13.6 | 0 | 3.00% | 0.00% | 0.96 | 0 | −22% | 0.20% | 0.12 | 0 | 1.08 | 0 | 20% | 0.70% |
| Y1923 | 13.5 | 0.02 | 2.00% | 0.20% | 1.03 | 0.01 | −16% | 0.70% | 0.1 | 0 | 1.09 | 0 | 12% | 1.40% |
| Y1927 | 13.6 | 0.01 | 2.60% | 0.00% | 1.01 | 0 | −18% | 0.30% | 0.12 | 0 | 1.08 | 0 | 16% | 0.80% |
| Y1929 | 13.4 | 0.01 | 1.40% | 0.00% | 1.1 | 0 | −11% | 0.30% | 0.12 | 0.01 | 1.09 | 0 | 18% | 0.70% |

Figure 4A:
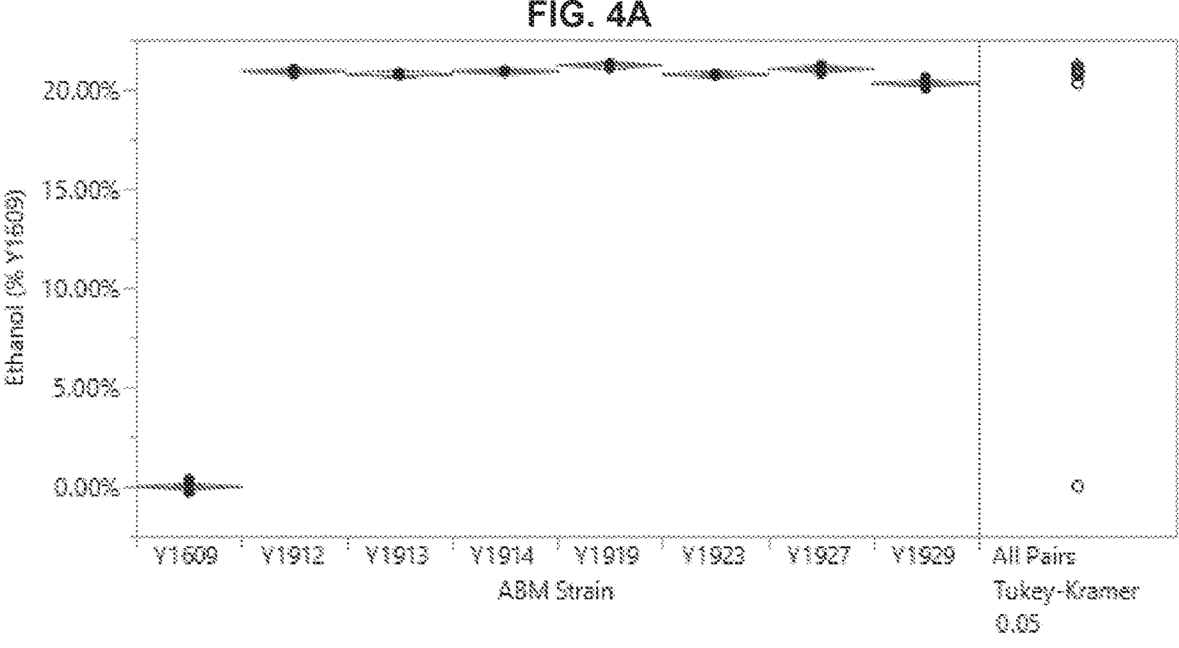
FIG. 4 shows the percent differences relative to a control (Y1609) under a high fermentation temperature (36° C.) in a proprietary synthetic corn starch medium (SCM) at pH 5.2 without exogenous addition of organic acids at the end of a 50-hour fermentation. Percent differences relative to control in ethanol at end of fermentation (FIG. 4A), glycerol at end of fermentation (FIG. 4B), and initial fermentation rate of fermentation (FIG. 4C) are shown.
Figure 4B:
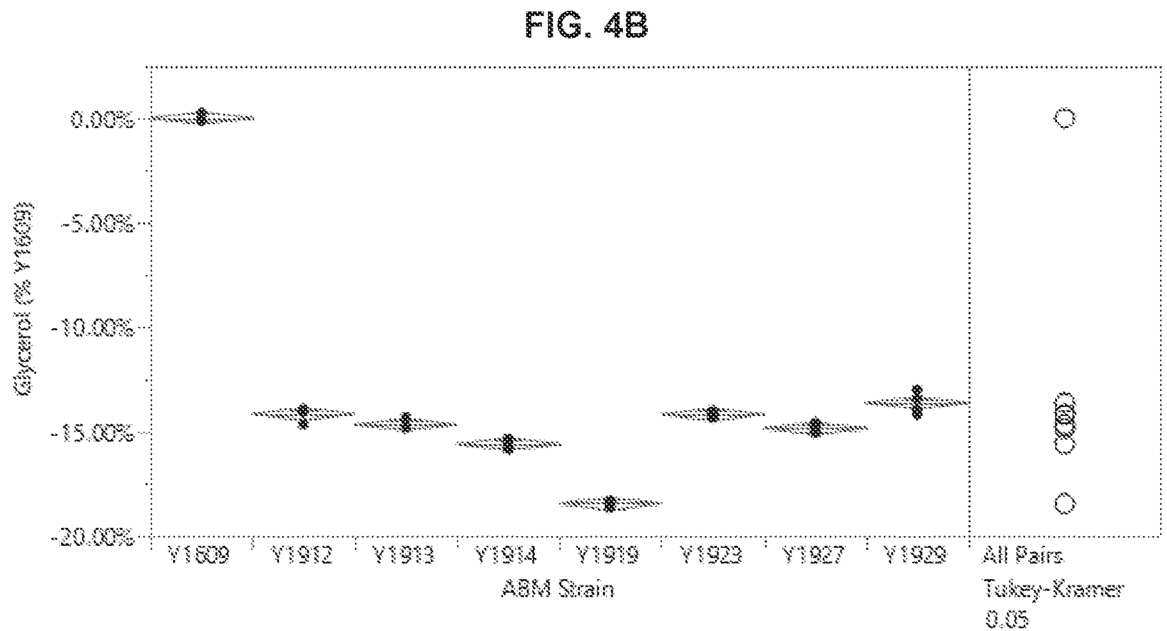
Figure 4C:
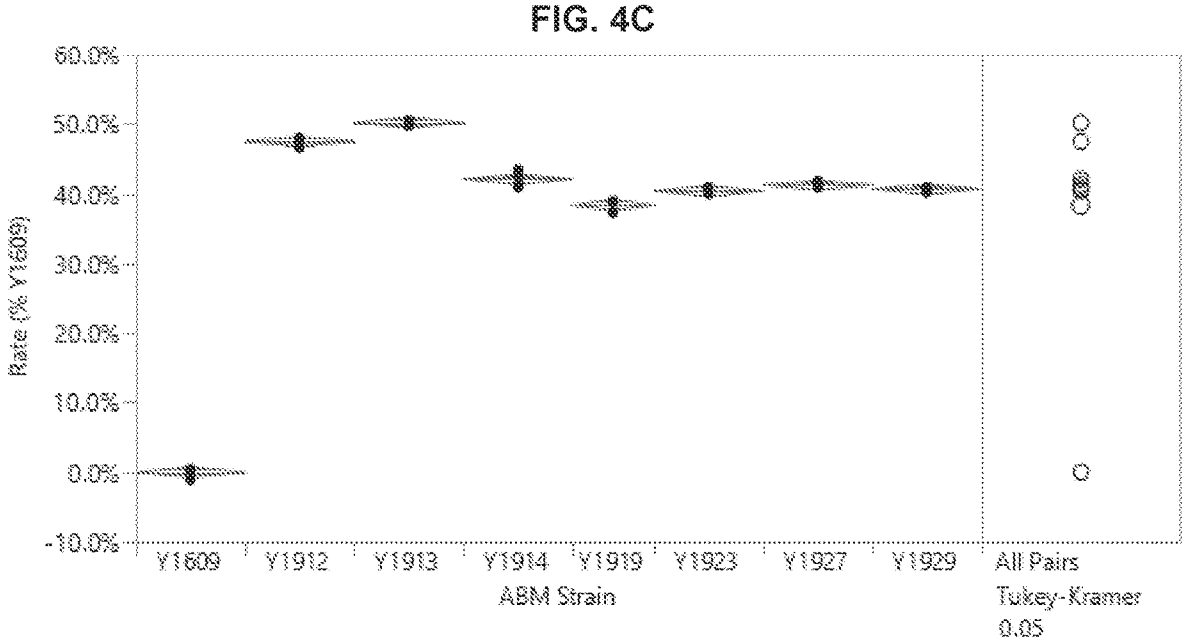

The parent yeast strains as described herein were evaluated for ethanol production, glycerol production, and fermentation rate at 36° C. and pH 5.2 in SCM without organic acids (TABLE 7 and FIG. 4). The control (Y1609) is shown for comparison.

TABLE 7

Defining characteristics relative to control under fermentation temperature of 36° C. and pH 5.2.

| | Ethanol (% w/v) | | Ethanol (% Y1609) | | Glycerol (% w/v) | | Glycerol (% Y1609) | | Acetic acid (% w/v) | | Lactic acid (% w/v) | | Rate (% Y1609) | |
|---|---|---|---|---|---|---|---|---|---|---|---|---|---|---|
| strain | Mean | Std Dev | Mean | Std Dev | Mean | Std Dev | Mean | Std Dev | Mean | Std Dev | Mean | Std Dev | Mean | Std Dev |
| Y1609 | 11.2 | 0.04 | 0% | 0.30% | 1.18 | 0 | 0.00% | 0.20% | 0.16 | 0 | 0.03 | 0 | 0.00% | 0.70% |
| Y1912 | 13.5 | 0.01 | 21% | 0.10% | 1.02 | 0 | −14% | 0.30% | 0.13 | 0.01 | 0.07 | 0 | 47% | 0.70% |

TABLE 7-continued

Defining characteristics relative to control under fermentation temperature of 36° C. and pH 5.2.

| | Ethanol (% w/v) | | Ethanol (% Y1609) | | Glycerol (% w/v) | | Glycerol (% Y1609) | | Acetic acid (% w/v) | | Lactic acid (% w/v) | | Rate (% Y1609) | |
|---|---|---|---|---|---|---|---|---|---|---|---|---|---|---|
| strain | Mean | Std Dev | Mean | Std Dev | Mean | Std Dev | Mean | Std Dev | Mean | Std Dev | Mean | Std Dev | Mean | Std Dev |
| Y1913 | 13.5 | 0.01 | 21% | 0.00% | 1.01 | 0 | −15% | 0.20% | 0.14 | 0 | 0.06 | 0 | 50% | 0.30% |
| Y1914 | 13.5 | 0 | 21% | 0.00% | 1 | 0 | −16% | 0.20% | 0.13 | 0 | 0.06 | 0 | 42% | 1.10% |
| Y1919 | 13.5 | 0.02 | 21% | 0.10% | 0.97 | 0 | −18% | 0.10% | 0.12 | 0 | 0.06 | 0 | 38% | 0.90% |
| Y1923 | 13.5 | 0.01 | 21% | 0.10% | 1.02 | 0 | −14% | 0.10% | 0.12 | 0.01 | 0.07 | 0 | 40% | 0.50% |
| Y1927 | 13.5 | 0.02 | 21% | 0.20% | 1.01 | 0 | −15% | 0.20% | 0.12 | 0.01 | 0.06 | 0 | 41% | 0.40% |
| Y1929 | 13.4 | 0.03 | 20% | 0.20% | 1.02 | 0.01 | −14% | 0.50% | 0.13 | 0.01 | 0.06 | 0 | 41% | 0.40% |

Figure 5A:
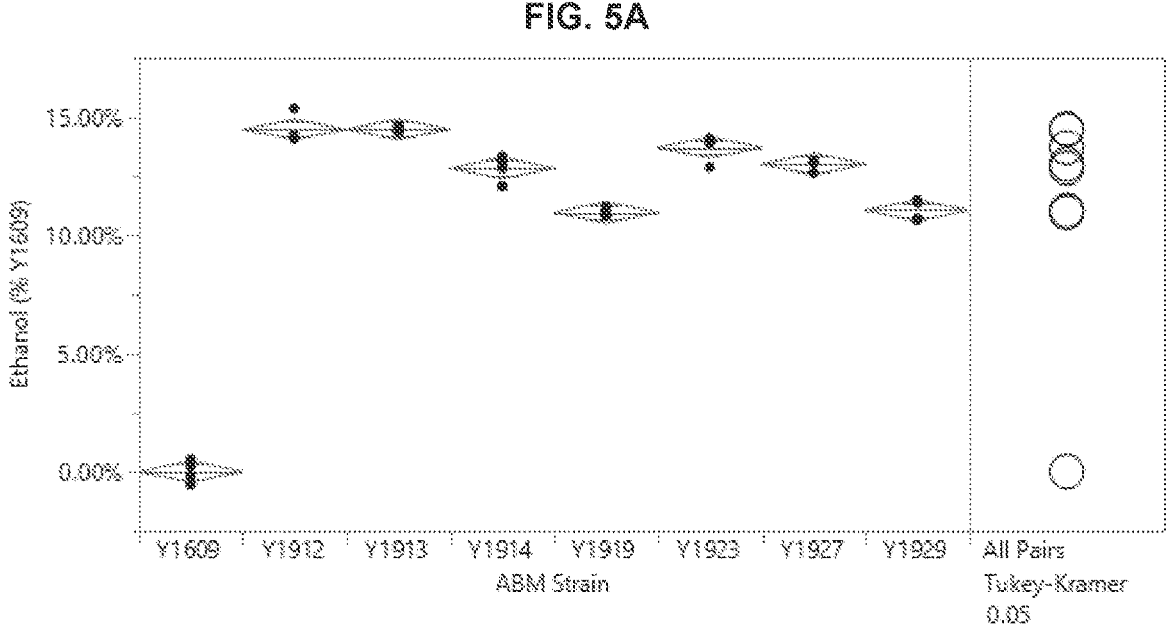
FIG. 5 shows the percent differences relative to a control (Y1609) under a high fermentation temperature (36° C.) in a proprietary synthetic corn starch medium (SCM) at pH 4.0 with exogenous addition of 1% w/v lactic acid and 0.05% w/v acetic acid at the end of a 50-hour fermentation. Percent differences relative to control in ethanol at end of fermentation (FIG. 5A), glycerol at end of fermentation (FIG. 5B), and initial fermentation rate of fermentation (FIG. 5C) are shown.
Figure 5B:
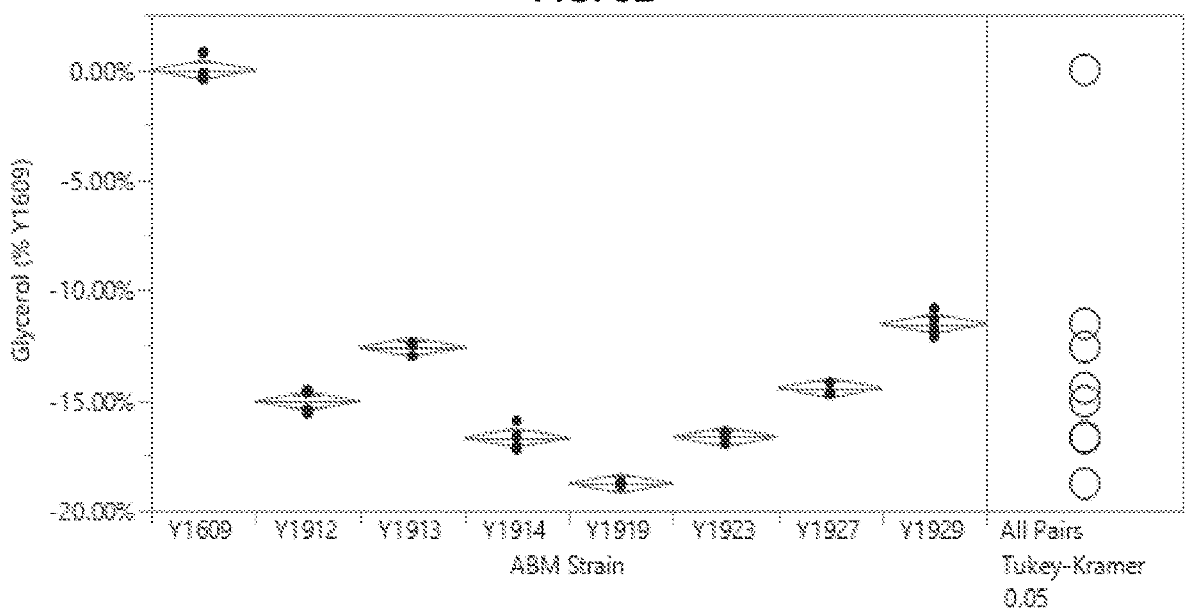
Figure 5C:
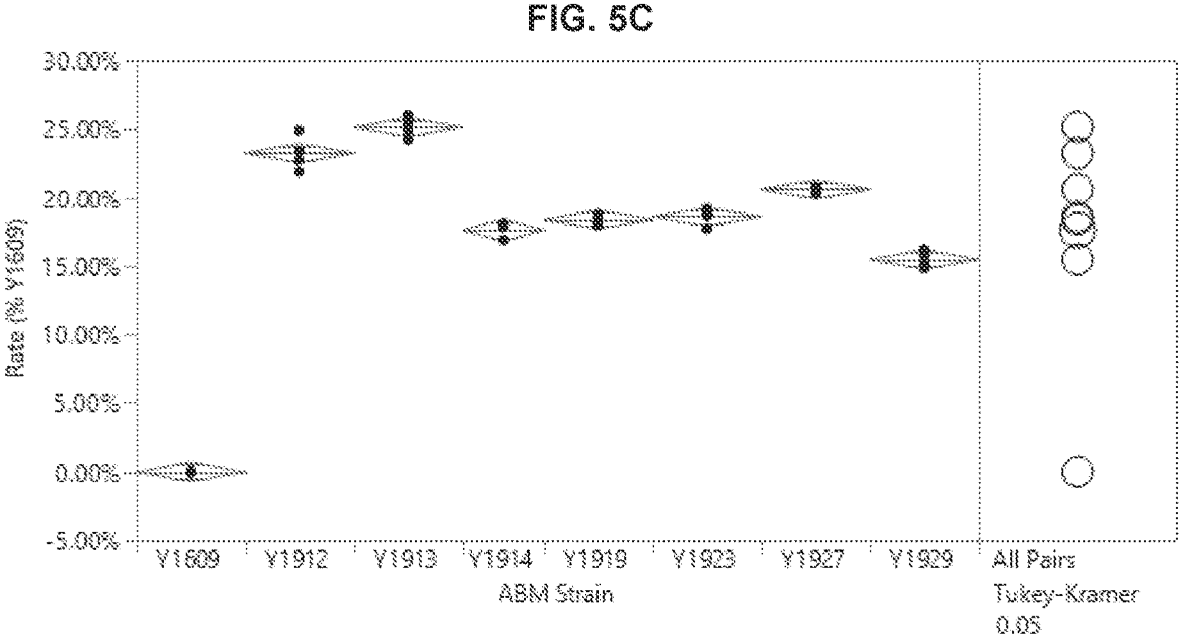

The parent yeast strains as described herein were evaluated for ethanol production, glycerol production, and fermentation rate at 36° C. and pH 4.0 in SCM with exogenous addition of 1% w/v lactic acid and 0.05% w/v acetic acid (TABLE 8 and FIG. 5). The control (Y1609) is shown for comparison.

TABLE 8

Defining characteristics relative to control under fermentation temperature of 36° C. and pH 4.0 with addition of organic acids.

| | Ethanol (% w/v) | | Ethanol (% Y1609) | | Glycerol (% w/v) | | Glycerol (% Y1609) | | Acetic acid (% w/v) | | Lactic acid (% w/v) | | Rate (% Y1609) | |
|---|---|---|---|---|---|---|---|---|---|---|---|---|---|---|
| strain | Mean | Std Dev | Mean | Std Dev | Mean | Std Dev | Mean | Std Dev | Mean | Std Dev | Mean | Std Dev | Mean | Std Dev |
| Y1609 | 11.5 | 0.05 | 0% | 0.50% | 1.16 | 0.01 | 0% | 0.50% | 0.14 | 0.01 | 1.05 | 0 | 0.00% | 0.10% |
| Y1912 | 13.1 | 0.07 | 14% | 0.60% | 0.99 | 0.01 | −15% | 0.50% | 0.13 | 0.01 | 1.07 | 0 | 23% | 1.30% |
| Y1913 | 13.1 | 0.01 | 14% | 0.10% | 1.01 | 0 | −13% | 0.30% | 0.13 | 0 | 1.06 | 0 | 25% | 0.80% |
| Y1914 | 12.9 | 0.06 | 13% | 0.60% | 0.97 | 0.01 | −17% | 0.60% | 0.12 | 0.01 | 1.07 | 0 | 18% | 0.60% |
| Y1919 | 12.7 | 0.02 | 11% | 0.20% | 0.94 | 0 | −19% | 0.10% | 0.12 | 0 | 1.06 | 0 | 18% | 0.30% |
| Y1923 | 13 | 0.06 | 14% | 0.60% | 0.97 | 0 | −17% | 0.20% | 0.12 | 0 | 1.07 | 0 | 19% | 0.60% |
| Y1927 | 12.9 | 0.03 | 13% | 0.20% | 0.99 | 0 | −14% | 0.30% | 0.13 | 0.01 | 1.07 | 0 | 21% | 0.30% |
| Y1929 | 12.7 | 0.05 | 11% | 0.40% | 1.03 | 0.01 | −12% | 0.60% | 0.13 | 0 | 1.07 | 0 | 15% | 0.60% |

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A *Saccharomyces* yeast strain selected from: (a) *Saccharomyces* strain Y1912, a representative sample of the strain having been deposited under NRRL Patent Deposit Designation No. Y-68003; (b) *Saccharomyces* strain Y1913, a representative sample of the strain having been deposited under NRRL Patent Deposit Designation No. Y-68004; (c) *Saccharomyces* strain Y1914, a representative sample of the strain having been deposited under NRRL Patent Deposit Designation No. Y-68005; (d) *Saccharomyces* strain Y1919, a representative sample of the strain having been deposited under NRRL Patent Deposit Designation No. Y-68006; (e) *Saccharomyces* strain Y1923, a representative sample of the strain having been deposited under NRRL Patent Deposit Designation No. Y-68007; (f) *Saccharomyces* strain Y1927, a representative sample of the strain having been deposited under NRRL Patent Deposit Designation No. Y-68008; and, (g) *Saccharomyces* strain Y1929, a representative sample of the strain having been deposited under NRRL Patent Deposit Designation No. Y-68009.

Clause 2. A derivative of a *Saccharomyces* yeast strain selected from: (a) *Saccharomyces* strain Y1912, a representative sample of the strain having been deposited under NRRL Patent Deposit Designation No. Y-68003; (b) *Saccharomyces* strain Y1913, a representative sample of the strain having been deposited under NRRL Patent Deposit Designation No. Y-68004; (c) *Saccharomyces* strain Y1914, a representative sample of the strain having been deposited under NRRL Patent Deposit Designation No. Y-68005; (d) *Saccharomyces* strain Y1919, a representative sample of the strain having been deposited under NRRL Patent Deposit Designation No. Y-68006; (e) *Saccharomyces* strain Y1923, a representative sample of the strain having been deposited under NRRL Patent Deposit Designation No. Y-68007; (f) *Saccharomyces* strain Y1927, a representative sample of the strain having been deposited under NRRL Patent Deposit Designation No. Y-68008; and, (g) *Saccharomyces* strain Y1929, a representative sample of the strain having been deposited under NRRL Patent Deposit Designation No. Y-68009.

Clause 3. The yeast strain of clause 1 or the derivative of clause 2, wherein the yeast strain or the derivative comprise one or more defining characteristics selected from: (a) a higher ethanol yield than *Saccharomyces* strain Y1609 under same fermentation conditions; (b) an increased temperature tolerance compared to *Saccharomyces* strain Y1609 at a temperature from 32° C. to 36° C.; (c) a lower glycerol yield than *Saccharomyces* strain Y1609 under same fermentation conditions; (d) an increased organic acid tolerance compared to *Saccharomyces* strain Y1609 at a pH from about 4.0 to about 5.2 in the presence of organic acids; and (e) an increased fermentation rate compared to *Saccharomyces* strain Y1609 under the same fermentation conditions.

Clause 4. The yeast strain or the derivative of any one of the preceding clauses, wherein the yeast strain or the derivative produces at least about 0.5% more ethanol after 50 hours of fermentation relative to *Saccharomyces cerevisiae* strain Y1609.

Clause 5. The yeast strain or the derivative of any one of the preceding clauses, wherein the yeast strain or the derivative produces at least about 2% less glycerol after 50 hours of fermentation relative to *Saccharomyces cerevisiae* strain Y1609.

Clause 6. The yeast strain or the derivative of any one of the preceding clauses, wherein the yeast strain or the derivative has a fermentation rate that is at least about 2% higher than *Saccharomyces cerevisiae* strain Y1609 after 24 hours of fermentation.

Clause 7. The yeast strain or derivative of any one of clauses 3-6, wherein the temperature is 32° C.

Clause 8. The yeast strain or the derivative of clause 3, wherein the yeast strain or the derivative produces at least about 5% more ethanol after 50 hours of fermentation relative to *Saccharomyces cerevisiae* strain Y1609.

Clause 9. The yeast strain or the derivative of clause 3, wherein the yeast strain or the derivative produces at least about 3% less glycerol after 50 hours of fermentation relative to *Saccharomyces cerevisiae* strain Y1609.

Clause 10. The yeast strain or the derivative of clause 3, wherein the yeast strain or the derivative has a fermentation rate that is at least about 10% higher than *Saccharomyces cerevisiae* strain Y1609 after 24 hours of fermentation.

Clause 11. The yeast strain or derivative of any one of clauses 3 or 8-11, wherein the temperature is 36° C.

Clause 12. The yeast strain or derivative of any one of clauses 3-11, wherein the organic acids comprise lactic acid, acetic acid, succinic acid, citric acid, malic acid, fumaric acid, or a combination thereof.

Clause 13. A method of producing the derivative of a *Saccharomyces* yeast strain of clause 2 comprising: (a) providing: (i) a first yeast strain, wherein the first yeast strain is selected from *Saccharomyces* strains Y1912, Y1913, Y1914, Y1919, Y1923, Y1927, Y1929, and derivatives thereof; and (ii) a second yeast strain, wherein the second yeast strain is in the *Saccharomyces* sensu stricto clade; (b) inducing sporulation of the first yeast strain and the second yeast strain; (c) screening and selecting spores from the first yeast strain and spores from the second yeast strain; (d) hybridizing the selected spores of the first yeast strain with the selected spores of the second yeast strain; and (e) screening or selecting for a derivative strain.

Clause 14. The method of clause 13, wherein step (c) comprises screening or selecting spores which exhibit one or more defining characteristics of *Saccharomyces* strains Y1912, Y1913, Y1914, Y1919, Y1923, Y1927, Y1929, or a derivative thereof.

Clause 15. The method of clause 13, wherein step (e) comprises screening or selecting a hybrid which exhibits one or more defining characteristics of *Saccharomyces* strains Y1912, Y1913, Y1914, Y1919, Y1923, Y1927, Y1929, or a derivative thereof.

Clause 16. A method of producing the derivative of a *Saccharomyces* yeast strain of clause 2 comprising: (a) providing: (i) a first yeast strain, wherein the first yeast strain is selected from *Saccharomyces* strains Y1912, Y1913, Y1914, Y1919, Y1923, Y1927, Y1929, and derivatives thereof; and (ii) one or more additional yeast strains that are in the *Saccharomyces* sensu stricto clade; (b) inducing sporulation of the first yeast strain and the one or more additional yeast strains to produce spores; (c) mixing all of the spores of step (b) to allow for hybridization of the spores; and (d) screening or selecting for a derivative strain.

Clause 17. The method of clause 16, wherein step (d) comprises screening or selecting a hybrid which exhibits one or more defining characteristics of *Saccharomyces* strains Y1912, Y1913, Y1914, Y1919, Y1923, Y1927, or Y1929.

Clause 18. A mutant yeast of a yeast strain of clause 1 or a derivative of clause 2.

Clause 19. A method of producing the mutant yeast of clause 18, wherein the mutant yeast is mutated by contacting the yeast strain with a mutagen.

Clause 20. The method of clause 19, wherein the mutagen is ethyl methanesulfonate (EMS), ultraviolet light (UV), X-rays, methylmethane sulphonate (MMS), nitrous acid, nitrosoguanidine (NNG), acridine mustard, 2-methoxy-6-chloro-9[3-(ethyl-2-chloroethyl)aminopropylamino]acridine•2 (ICR-170), or nitrogen mustard.

Clause 21. A method of producing the mutant yeast of clause 18, wherein the mutant yeast is mutated by contacting the derivative with a mutagen.

Clause 22. The method of clause 21, wherein the mutagen is ethyl methanesulfonate (EMS), ultraviolet light (UV), X-rays, methylmethane sulphonate (MMS), nitrous acid, nitrosoguanidine (NNG), acridine mustard, 2-methoxy-6-chloro-9[3-(ethyl-2-chloroethyl)aminopropylamino]acridine•2 (ICR-170), or nitrogen mustard.

Clause 23. An evolved yeast of a yeast strain of clause 1 or a derivative of clause 2.

Clause 24. A method of producing the evolved yeast of clause 23, wherein evolution is induced by applying selection pressure to the yeast strain.

Clause 25. A method of producing the evolved yeast of clause 23, wherein evolution is induced by applying selection pressure to the derivative.

Clause 26. A genetically modified yeast of a yeast strain of clause 1 or a derivative of clause 2.

Clause 27. The genetically modified yeast of clause 26, wherein a nucleic acid sequence of the genetically modified yeast is changed using gene editing.

Clause 28. A recombinant yeast of a yeast strain of clause 1 or a derivative of clause 2.

Clause 29. The recombinant yeast of clause 28, wherein the recombinant yeast comprises a modification to suppress expression of a gene, enhance expression of a gene, introduce a gene, or delete a gene.

Clause 30. A process for producing ethanol from a substrate by contacting the substrate with a fermenting organism, wherein the fermenting organism is selected from: (a) *Saccharomyces* strain Y1912, a representative sample of the strain having been deposited under NRRL Patent Deposit Designation No. Y-68003, or a derivative thereof; (b) *Saccharomyces* strain Y1913, a representative sample of the strain having been deposited under NRRL Patent Deposit Designation No. Y-68004, or a derivative thereof; (c) *Saccharomyces* strain Y1914, a representative sample of the strain having been deposited under NRRL Patent Deposit Designation No. Y-68005, or a derivative thereof; (d) *Saccharomyces* strain Y1919, a representative sample of the strain having been deposited under NRRL Patent Deposit Designation No. Y-68006, or a derivative thereof; (e) *Saccharomyces* strain Y1923, a representative sample of the strain having been deposited under NRRL Patent Deposit Designation No. Y-68007, or a derivative thereof; (f) *Saccharomyces* strain Y1927, a representative sample of the strain having been deposited under NRRL Patent Deposit Designation No. Y-68008, or a derivative thereof; and, (g) *Saccharomyces* strain Y1929, a representative sample of the strain having been deposited under NRRL Patent Deposit Designation No. Y-68009, or a derivative thereof.

Clause 31. The process of clause 30, wherein the substrate comprises or originates from sugar cane, sugar beet, sweet sorghum, agave, corn, wheat, rice, barley, rye, sorghum, triticale, potato, sweet potato, cassava, or a combination thereof.

Clause 32. The process of clause 30, wherein the yeast strain comprises one or more defining characteristics selected from: (a) a higher ethanol yield than *Saccharomyces* strain Y1609 under same fermentation conditions; (b) an increased temperature tolerance compared to *Saccharomyces* strain Y1609 at a temperature from 32° C. to 36° C.; (c) a lower glycerol yield than *Saccharomyces* strain Y1609 under same fermentation conditions; (d) an increased organic acid tolerance compared to *Saccharomyces* strain Y1609 at a pH from about 4.0 to about 5.2 in the presence of organic acids; and (e) an increased fermentation rate compared to *Saccharomyces* strain Y1609 under the same fermentation conditions.

Clause 33. The process of clause 30, wherein the ethanol is used for fuel ethanol, industrial ethanol, potable ethanol, or a combination thereof.

Clause 34. The process of clause 30, wherein the ethanol is produced using a starch.

Clause 35. The process of clause 34, wherein simultaneous saccharification and fermentation (SSF) or continuous fermentation is used to produce the ethanol.

Clause 36. The process of clause 30, wherein the ethanol is produced using a sugar.

Clause 37. The process of clause 36, wherein batch fermentation or continuous fermentation is used to produce the ethanol.

Clause 38. The process of clause 30, wherein the ethanol is produced using a lignocellulosic sugar.

Clause 39. The process of clause 38, wherein simultaneous saccharification and fermentation (SSF) or Separate Hydrolysis and Fermentation (SHF) is used to produce the ethanol.

Clause 40. A composition comprising the yeast strain of clause 1 or the derivative of clause 2 and one or more components selected from surfactants, emulsifiers, gums, swelling agents, protectants, and antioxidants.

Clause 41. The composition of clause 40, wherein the composition comprises one or more defining characteristics selected from: (a) a higher ethanol yield than Fali under same fermentation conditions; (b) an increased temperature tolerance compared to Fali at a temperature from 32° C. to 36° C.; (c) a lower glycerol yield than Fali under same fermentation conditions; (d) an increased organic acid tolerance compared to Fali at a pH from about 4.0 to about 5.2 in the presence of organic acids; and (e) an increased fermentation rate compared to Fali under the same fermentation conditions.

Clause 42. A process for producing ethanol from a biomass by contacting the biomass with the composition of clause 40.

Clause 43. The process of clause 42, wherein the ethanol is used for fuel ethanol, industrial ethanol, potable ethanol, or a combination thereof.

Clause 44. The process of clause 42, wherein the ethanol is produced using a starch.

Clause 45. The process of clause 44, wherein simultaneous saccharification and fermentation (SSF) or continuous fermentation is used to produce the ethanol.

Clause 46. The process of clause 42, wherein the ethanol is produced using a sugar.

Clause 47. The process of clause 46, wherein batch fermentation or continuous fermentation is used to produce the ethanol.

Clause 48. The process of clause 42, wherein the ethanol is produced using a lignocellulosic sugar.

Clause 49. The process of clause 48, wherein simultaneous saccharification and fermentation (SSF) or Separate Hydrolysis and Fermentation (SHF) is used to produce the ethanol.

Clause 50. A method of producing a fermentation product from a substrate by contacting the substrate with a fermenting organism, wherein the fermenting organism is selected from: (a) *Saccharomyces* strain Y1912, a representative sample of the strain having been deposited under NRRL Patent Deposit Designation No. Y-68003, or a derivative thereof; (b) *Saccharomyces* strain Y1913, a representative sample of the strain having been deposited under NRRL Patent Deposit Designation No. Y-68004, or a derivative thereof; (c) *Saccharomyces* strain Y1914, a representative sample of the strain having been deposited under NRRL Patent Deposit Designation No. Y-68005, or a derivative thereof; (d) *Saccharomyces* strain Y1919, a representative sample of the strain having been deposited under NRRL Patent Deposit Designation No. Y-68006, or a derivative thereof; (e) *Saccharomyces* strain Y1923, a representative sample of the strain having been deposited under NRRL Patent Deposit Designation No. Y-68007, or a derivative thereof; (f) *Saccharomyces* strain Y1927, a representative sample of the strain having been deposited under NRRL Patent Deposit Designation No. Y-68008, or a derivative thereof; and, (g) *Saccharomyces* strain Y1929, a representative sample of the strain having been deposited under NRRL Patent Deposit Designation No. Y-68009, or a derivative thereof.

Clause 51. The method of clause 50, wherein the substrate comprises or originates from sugar cane, sugar beet, sweet sorghum, agave, corn, wheat, rice, barley, rye, sorghum, triticale, potato, sweet potato, cassava, or a combination thereof.

Clause 52. The method of clause 50, wherein the fermentation product is ethanol.

Clause 53. The method of clause 52, wherein the ethanol is used for fuel ethanol, industrial ethanol, potable ethanol, or a combination thereof.

Clause 54. The method of clause 50, wherein batch fermentation, continuous fermentation, simultaneous saccharification and fermentation (SSF), or Separate Hydrolysis and Fermentation (SHF) is used to produce the fermentation product.

8. BIOLOGICAL DEPOSITS

Representative samples of the *Saccharomyces* yeast strains as described herein were deposited with the Agricultural Research Service Patent Culture Collection Northern Regional Research Center (NRRL), 1815 University Street, Peoria, IL, USA on Dec. 10, 2020 and were assigned NRRL Patent Deposit Designation No. Y-68003 (Y1912), NRRL Patent Deposit Designation No. Y-68004 (Y1913), NRRL Patent Deposit Designation No. Y-68005 (Y1914), NRRL Patent Deposit Designation No. Y-68006 (Y1919), NRRL Patent Deposit Designation No. Y-68007 (Y1923), NRRL Patent Deposit Designation No. Y-68008 (Y1927), and NRRL Patent Deposit Designation No. Y-68009 (Y1929) on Dec. 23, 2020. The deposit will be maintained at the NRRL depository under the terms of the Budapest Treaty on the International Recognition of the Deposit of Microorganisms for the Purposes of Patent Procedure for a term of at least thirty years and at least five years after the most recent request for the furnishing of a sample of the deposit was received by the depository. Applicants have satisfied all the requirements of 37 C.F.R. §§ 1.801-1.809, including providing an indication of the viability of the sample. Additional deposits will be made at the NRRL as needed to ensure availability, subject to the conditions described herein. Applicants impose no restrictions on the availability of the deposited material from the NRRL after the issuance of a patent from this application. Applicants have no authority to wave any restrictions imposed by law on the transfer of biological material or its transportation in worldwide commerce. Applicants do not waive any of their rights granted under any patents issuing from this application in any country.

What is claimed is:

1. A *Saccharomyces* yeast strain wherein:

(i) the yeast strain is selected from the group consisting of:

(a) *Saccharomyces* strain Y1912, a representative sample of the strain having been deposited under NRRL Patent Deposit Designation No. Y-68003;

(b) *Saccharomyces* strain Y1913, a representative sample of the strain having been deposited under NRRL Patent Deposit Designation No. Y-68004;

(c) *Saccharomyces* strain Y1914, a representative sample of the strain having been deposited under NRRL Patent Deposit Designation No. Y-68005;

(d) *Saccharomyces* strain Y1919, a representative sample of the strain having been deposited under NRRL Patent Deposit Designation No. Y-68006;

(e) *Saccharomyces* strain Y1923, a representative sample of the strain having been deposited under NRRL Patent Deposit Designation No. Y-68007;

(f) *Saccharomyces* strain Y1927, a representative sample of the strain having been deposited under NRRL Patent Deposit Designation No. Y-68008; and, (g) *Saccharomyces* strain Y1929, a representative sample of the strain having been deposited under NRRL Patent Deposit Designation No. Y-68009; and (ii) the yeast strain comprise one or more defining characteristics selected from the group consisting of:

(a) a higher ethanol yield than *Saccharomyces* strain Y1609 under same fermentation conditions;

(b) an increased temperature tolerance compared to *Saccharomyces* strain Y1609 at a temperature from 32° C. to 36° C.;

(c) a lower glycerol yield than *Saccharomyces* strain Y1609 under same fermentation conditions;

(d) an increased organic acid tolerance compared to *Saccharomyces* strain Y1609 at a pH from about 4.0 to about 5.2 in the presence of organic acids; and (e) an increased fermentation rate compared to *Saccharomyces* strain Y1609 under the same fermentation conditions.

2. The yeast strain of claim 1, wherein the yeast strain:

produces at least about 0.5% more ethanol after 50 hours of fermentation relative to *Saccharomyces cerevisiae* strain Y1609;

produces at least about 2% less glycerol after 50 hours of fermentation relative to *Saccharomyces cerevisiae* strain Y1609;

has a fermentation rate that is at least about 2% higher than *Saccharomyces cerevisiae* strain Y1609 after 24 hours of fermentation; or a combination thereof.

3. The yeast strain of claim 1, wherein the organic acids comprise lactic acid, acetic acid, succinic acid, citric acid, malic acid, fumaric acid, or a combination thereof.

4. A process for producing ethanol from fermentable a substrate by contacting the fermentable substrate with a fermenting organism, wherein:

(i) the fermenting organism is selected from the group consisting of:

(a) *Saccharomyces* strain Y1912, a representative sample of the strain having been deposited under NRRL Patent Deposit Designation No. Y-68003;

(b) *Saccharomyces* strain Y1913, a representative sample of the strain having been deposited under NRRL Patent Deposit Designation No. Y-68004;

(c) *Saccharomyces* strain Y1914, a representative sample of the strain having been deposited under NRRL Patent Deposit Designation No. Y-68005;

(d) *Saccharomyces* strain Y1919, a representative sample of the strain having been deposited under NRRL Patent Deposit Designation No. Y-68006;

(e) *Saccharomyces* strain Y1923, a representative sample of the strain having been deposited under NRRL Patent Deposit Designation No. Y-68007;

(f) *Saccharomyces* strain Y1927, a representative sample of the strain having been deposited under NRRL Patent Deposit Designation No. Y-68008; and, (g) *Saccharomyces* strain Y1929, a representative sample of the strain having been deposited under NRRL Patent Deposit Designation No. Y-68009; and (ii) the fermenting organism comprises one or more defining characteristics selected from the group consisting of:

(a) a higher ethanol yield than *Saccharomyces* strain Y1609 under same fermentation conditions;

(b) an increased temperature tolerance compared to *Saccharomyces* strain Y1609 at a temperature from 32° C. to 36° C.;

(c) a lower glycerol yield than *Saccharomyces* strain Y1609 under same fermentation conditions;

(d) an increased organic acid tolerance compared to *Saccharomyces* strain Y1609 at a pH from about 4.0 to about 5.2 in the presence of organic acids; and (e) an increased fermentation rate compared to *Saccharomyces* strain Y1609 under the same fermentation conditions.

5. The process of claim 4, wherein the fermentable substrate comprises or originates from sugar cane, sugar beet, sweet sorghum, agave, corn, wheat, rice, barley, rye, sorghum, triticale, potato, sweet potato, cassava, or a combination thereof.

6. The process of claim 4, wherein the ethanol is used for fuel ethanol, industrial ethanol, potable ethanol, or a combination thereof.

7. The process of claim 4, wherein the fermentable substrate for producing the ethanol is a starch or a sugar.

8. The process of claim 7, wherein simultaneous saccharification and fermentation (SSF), batch fermentation, separate hydrolysis and fermentation (SHF), or continuous fermentation is used to produce the ethanol.

9. A composition comprising the yeast strain of claim 1 and one or more components selected from surfactants, emulsifiers, gums, swelling agents, protectants, and antioxidants, wherein the composition comprises one or more defining characteristics selected from the group consisting of:

(a) a higher ethanol yield than *Saccharomyces* strain Y1609 under same fermentation conditions;

(b) an increased temperature tolerance compared to *Saccharomyces* strain Y1609 at a temperature from 32° C. to 36° C.;

(c) a lower glycerol yield than *Saccharomyces* strain Y1609 under same fermentation conditions;

(d) an increased organic acid tolerance compared to *Saccharomyces* strain Y1609 at a pH from about 4.0 to about 5.2 in the presence of organic acids; and (e) an increased fermentation rate compared to *Saccharomyces* strain Y1609 under the same fermentation conditions.

10. A process for producing ethanol from a biomass by contacting the biomass with the composition of claim 9.

11. The process of claim 10, wherein the ethanol is used for fuel ethanol, industrial ethanol, potable ethanol, or a combination thereof.

12. The process of claim 10, wherein the ethanol is produced using a starch or a sugar.

13. The process of claim 12, wherein simultaneous saccharification and fermentation (SSF), batch fermentation, separate hydrolysis and fermentation (SHF), or continuous fermentation is used to produce the ethanol.

14. A method of producing a fermentation product from a fermentable substrate by contacting the fermentable substrate with a fermenting organism, wherein the fermenting organism is selected from the group consisting of:

(a) *Saccharomyces* strain Y1912, a representative sample of the strain having been deposited under NRRL Patent Deposit Designation No. Y-68003;

(b) *Saccharomyces* strain Y1913, a representative sample of the strain having been deposited under NRRL Patent Deposit Designation No. Y-68004;

(c) *Saccharomyces* strain Y1914, a representative sample of the strain having been deposited under NRRL Patent Deposit Designation No. Y-68005;

(d) *Saccharomyces* strain Y1919, a representative sample of the strain having been deposited under NRRL Patent Deposit Designation No. Y-68006;

(e) *Saccharomyces* strain Y1923, a representative sample of the strain having been deposited under NRRL Patent Deposit Designation No. Y-68007;

(f) *Saccharomyces* strain Y1927, a representative sample of the strain having been deposited under NRRL Patent Deposit Designation No. Y-68008; and, (g) *Saccharomyces* strain Y1929, a representative sample of the strain having been deposited under NRRL Patent Deposit Designation No. Y-68009.

15. The method of claim 14, wherein the fermentable substrate comprises or originates from sugar cane, sugar beet, sweet sorghum, agave, corn, wheat, rice, barley, rye, sorghum, triticale, potato, sweet potato, cassava, or a combination thereof.

16. The method of claim 14, wherein the fermentation product is ethanol, and the ethanol is used for fuel ethanol, industrial ethanol, potable ethanol, or a combination thereof.

17. The method of claim 14, wherein batch fermentation, continuous fermentation, simultaneous saccharification and fermentation (SSF), or separate hydrolysis and fermentation (SHF) is used to produce the fermentation product.

* * * * *